United States Patent [19]
Cordell et al.

[11] Patent Number: 5,977,074
[45] Date of Patent: Nov. 2, 1999

[54] INHIBITORS OF β-AMYLOID PROTEIN PRODUCTION

[75] Inventors: Barbara Cordell, Palo Alto, Calif.; Daniel Schirlin, Lampertheim, France; Norton P. Peet, Cincinnati, Ohio; Jeffrey N. Higaki, Mountain View, Calif.; Viviane Van Dorsselaer, Strasbourg, France; Michael R. Angelastro, Cincinnati, Ohio

[73] Assignee: Merrell Pharmaceuticals, Inc., Bridgewater, N.J.

[21] Appl. No.: 08/624,407

[22] PCT Filed: Sep. 20, 1994

[86] PCT No.: PCT/US94/10679

§ 371 Date: Mar. 28, 1996

§ 102(e) Date: Mar. 28, 1996

[87] PCT Pub. No.: WO95/09838

PCT Pub. Date: Apr. 13, 1995

[30] Foreign Application Priority Data

Oct. 1, 1993 [EP] European Pat. Off. ............ 93 402 398

[51] Int. Cl.$^6$ .............................. A61K 38/05; C07K 1/00
[52] U.S. Cl. ........................... 514/19; 514/357; 546/145; 546/170; 546/335; 546/337; 560/27; 564/157; 564/158; 564/165; 549/44; 544/162; 544/168
[58] Field of Search .................... 514/19, 357; 546/145, 546/170, 335, 337; 560/27; 564/157, 158, 165; 549/44; 544/162, 168

[56] References Cited

U.S. PATENT DOCUMENTS 4,820,691  4/1989  Patel .

FOREIGN PATENT DOCUMENTS

| | | |
|---|---|---|
| 0195212 | 9/1986 | European Pat. Off. . |
| 0363284 | 4/1990 | European Pat. Off. . |
| 0402646 | 12/1990 | European Pat. Off. . |
| 0410411 | 1/1991 | European Pat. Off. . |
| 0520336 | 12/1992 | European Pat. Off. . |
| 0529568 | 3/1993 | European Pat. Off. . |
| 0580161 | 1/1994 | European Pat. Off. . |
| 8400365 | 2/1984 | WIPO . |
| 9211850 | 7/1992 | WIPO . |
| 9212123 | 7/1992 | WIPO . |
| 9214696 | 9/1992 | WIPO . |
| 9413319 | 6/1994 | WIPO . |

OTHER PUBLICATIONS

D. Matteson et al., J. Am. Chem. Soc, 103, pp. 5241–5242 (1981).

D. Matteson et al., J. Am. Chem. Soc. 102, pp. 7590–7591 (1980).

M. Angelastro et al., J. Am. Chem. Soc. vol. 33, No. 1, pp. 11–13 (1990).

R. Nixon et al., Ann. NY Acad. Sco., 568, pp. 198–208 (1993).

D. Schirlin et al., Bioor. & Med. Chem. Letters, vol. 3, No. 2, pp. 253–258 (1993).

Schirlin et al., Bioorganic & Med. Chem. Lett. vol. 3, No. 2 pp. 253–258 (1993).

*Primary Examiner*—Bennett Celsa
*Attorney, Agent, or Firm*—Balaram Gupta

[57] ABSTRACT

This invention relates to compounds and pharmaceutical compositions, and methods for inhibiting or preventing the amyloid protein deposits in the brain which are associated with Alzheimer's disease and aged Down's syndrome patients. More particularly, it relates to the treatment of Alzheimer's disease.

16 Claims, No Drawings

SEQUENCE LISTING

```
<160> NUMBER OF SEQ ID NOS: 5

<210> SEQ ID NO 1
<211> LENGTH: 4
<212> TYPE: PRT
<213> ORGANISM: unidentified
<220> FEATURE:
<221> NAME/KEY: UNSURE
<222> LOCATION: (1)..(4)

<400> SEQUENCE: 1

Xaa Xaa Xaa Xaa
  1

<210> SEQ ID NO 2
<211> LENGTH: 4
<212> TYPE: PRT
<213> ORGANISM: unidentified
<220> FEATURE:
<221> NAME/KEY: UNSURE
<222> LOCATION: (1)..(4)
```

```
<400> SEQUENCE: 2

Xaa Xaa Xaa Xaa
 1

<210> SEQ ID NO 3
<211> LENGTH: 4
<212> TYPE: PRT
<213> ORGANISM: unidentified
<220> FEATURE:
<221> NAME/KEY: UNSURE
<222> LOCATION: (1)..(4)

<400> SEQUENCE: 3

Xaa Xaa Xaa Xaa
 1

<210> SEQ ID NO 4
<211> LENGTH: 4
<212> TYPE: PRT
<213> ORGANISM: unidentified
<220> FEATURE:
<221> NAME/KEY: UNSURE
<222> LOCATION: (1)..(4)

<400> SEQUENCE: 4

Xaa Xaa Xaa Xaa
 1

<210> SEQ ID NO 5
<211> LENGTH: 4
<212> TYPE: PRT
<213> ORGANISM: unidentified
<220> FEATURE:
<221> NAME/KEY: UNSURE
<222> LOCATION: (1)..(4)

<400> SEQUENCE: 5

Xaa Xaa Xaa Xaa
```

INHIBITORS OF β-AMYLOID PROTEIN PRODUCTION

This application is a national stage entry under 35 U.S.C. § 371 of an International Application No. PCT/US94/10679, filed Sep. 20, 1994, which claims the benefit of priority of European Patent Application No. 93402398.7, filed Oct. 1, 1993.

TECHNICAL FIELD

This invention relates to compounds and pharmaceutical compositions, and methods for inhibiting or preventing the amyloid protein deposits in the brain. More particularly, the present invention relates to the treatment of Alzheimer's disease.

BACKGROUND ART

It is estimated that over 5% of the U.S. population over 65 and over 15% of the U.S. population over 85 are affected by Alzheimer's disease. (Cross, A. J., *Eur. J. Pharmacol.* (1982) 82: 77–80; Terry, R. D., et al., *Ann. Neurol.* (1983) 14: 497–506). It is believed that the principal cause of confinement of the elderly in long term care facilities is due to this disease, and approximately 65% of those dying in skilled nursing homes suffer from it.

Certain facts about the biochemical and metabolic phenomena associated with the presence of Alzheimer's disease are known. Two morphological and histopathological changes noted in Alzheimer's disease brains are neurofibrillary tangles (NFT) and amyloid deposits. Intraneuronal neurofibrillary tangles are present in other degenerative diseases as well, but the presence of amyloid deposits both in the intraneuronal spaces (neuritic plaques) and in the surrounding microvasculature (vascular plaques) seems to be characteristic of Alzheimer's. Of these, the neuritic plaques seem to be the most prevalent (Price, D. L., et al., *Drug Development Research* (1985) 5: 59–68). Plaques are also seen in the brains of aged Down's Syndrome patients who develop Alzheimer's disease.

Plaque-rich brains of Alzheimer's patients have been used as a source to extract an approximately 4.2 kd "core" polypeptide, amyloid plaque core protein (APCP). This peptide was designated β-protein by (Glenner, G., et al., *Biochem. Biophys. Res. Commun.* (1984) 120: 885–890). The amino acid sequence of the amino-terminus was determined (Glenner, G., et al., *Biochem. Biophys. Res. Commun.* (1984) 122: 1131–1135; Masters, C. L., et al., *Proc. Natl. Acad. Sci USA* (1985) 82: 4245–42259). The amino acid sequences reported by the two groups were identical, except that Glenner et al. reported a glutamine residue at position 11 for Alzheimer's disease cerebral vascular amyloid whereas Master et al. reported glutamic acid at position 11. Also, the former authors reported that the cerebral vascular amyloid has a homogeneous amino-terminus, while the latter authors reported heterogeneous amino-termini. Both groups showed that the same peptide is found in the amyloid plaque cores and vascular amyloid of adult Down's syndrome-afflicted individuals and report glutamic acid at position 11. Wong, C. W., et al. (*Proc. Natl. Acad. Sci.* USA (1985) 82: 8729–8732) showed that a synthetic peptide which was homologous to the first ten amino acids of the β-amyloid core protein described by Masters (supra) was able to raise antibodies in mice and that these antibodies could be used to stain not only amyloid-laden cerebral vessels, but also neuritic plaques. These results were confirmed by Allsop, D. et al., *Neuroscience Letters* (1986) 68: 252–256 using antibodies directed against a synthetic peptide corresponding to amino acids 8–17. Thus, in general, the plaque protein found in various locations of the brain of Alzheimer's patients appears to be similar in immunoreactivity. It is highly insoluble, as shown by the inability to achieve solubilization in many commonly used denaturants, such as detergents and chaotropic agents (Masters, supra, Allsop, D., et al. (supra)).

There are six known instances of disease-associated amyloid deposits in which the amyloid is produced from a precursor protein: for primary amyloidosis, the precursor is an immunoglobulin light chain; for secondary amyloidosis, the precursor is amyloid A protein; for amyloidosis, prealbumin or a variant thereof; for medullary carcinoma of thyroid, a procalcitonin fragment; and for hereditary cerebral hemorrhage, gamma-trace fragment (See, e.g., Glenner, G. *New England Journal of Medicine* (1980.) 302: 1283; Sletton, K., et al. *Biochem J* (1981) 195: 561; Benditt, et al. *FEBS Lett*(1971) 19:169; Sletton, K., al., *Eur J Biochem* (1974) 41: 117; Sletton, K. *J Exp Med* (1976) 143: 993). The foregoing is a partial list and there are at least a number of additional references with regard to procalcitonin fragment as a precursor for the amyloid of the thyroid carcinoma.

It is believed, by analogy to other known instances of disease-associated amyloid deposits, that the β-amyloid core protein associated with Alzheimer's disease is formed from a precursor protein. A protein containing the β-amyloid core protein sequence within the framework of a larger protein was described by Kang, J., et al., (*Nature* (1987) 325: 733–736). The sequence of this protein was deduced from the sequence of a cDNA clone isolated from a human fetal brain tissue cDNA library and consists of 695 amino acid residues wherein the amino terminus of the β-amyloid core protein begins at position 597. A second precursor protein containing the β-amyloid sequence was predicted from a cDNA clone isolated by Ponte, et al. (*Nature* (1988) 331: 525–527). The cDNA clone isolated by Ponte et al. encoded a precursor protein which is identical to that identified by Kang, et al., except that it contains an additional 57-amino acid sequence inserted upstream of the β-amyloid core protein sequence. The 57-amino acid insert sequence comprises a functional domain which is highly homologous to a series of protease inhibitors known as the Kunitz-type serine protease inhibitors. Others have characterized an additional amyloid precursor protein (See Kitaguchi, et al., *Nature* (1988) 331: 530–532) which contains 770 amino acids. The precursor identified by Kitaguchi is identical to that of Ponte et al., except that it contains an additional 19 amino acids adjacent the 57-amino acid protease inhibitor domain. It is not known that these additional 19 amino acids provide any additional functionality to the molecule. The various amyloid precursor proteins which have been identified from cDNA clones arise as the result of alternative message splicing during transcription of a single amyloid precursor gene.

It has been shown that the amyloid precursor proteins are processed by normal cellular metabolism to produce the β-amyloid core protein (Haass, et al. *Nature* (1992) 359: 322–325; Shoji, et al. *Science* (1992) 258: 126–129,; Seubert, et al. *Nature* (1992) 359: 325–327). It is unclear, however, if individuals with Alzheimer's disease produce higher amounts of the β-amyloid core protein, although it has been shown that individuals with Down's syndrome, who invariably develop Alzheimer's disease, express twofold more B-amyloid precursor protein (Neve, et al. *Neuron* (1988) 1: 669–677). It is believed that the development of amyloid plaques in Alzheimer's disease brains results from excess production and/or reduced clearance or sequestration of the β-amyloid protein. Hence, if means could be devised for intervening in the process of plaque formation by preventing or inhibiting the processing of the precursor to produce the amyloid plaque core protein, such means could constitute a method of treating or ameliorating the progression of Alzheimer's disease. Until now, however, the processing of amyloid precursor protein to produce the β-amyloid core protein has not been sufficiently understood to allow for effective therapeutic intervention in the process which results in amyloid deposition.

Numerous reports exist describing putative proteinases which are purported to be responsible for generating the β-amyloid protein and/or Alzheimer's disease pathology. These putative proteinases include a broad spectrum of classes of enzymes, for example, serine, cysteine, and metallo-proteinases. A number of β-amyloid forming proteinases have been isolated and characterized. Some reported candidates include multicatalytic proteinase (*FEBS* 304: 57–60 (1992) and *FEBS Lett.* 257: 388–92 (1989)), mast cell chymase (*J. Biol. Chem.* 265: 3836–43 (1990), metallo-endopeptidase 24.15, *Biochem. Biophys. Res. Commun.* 185: 746–52 (1992)), calcium-activated neutral proteinases (calpain) (*J. Neurosci.*) 10: 2400–11 (1990), a calcium-activated serine proteinase (*Biochem. Biophys. Res. Commun.* 174: 790–96 (1991)), and prolyl-endopeptidase (*FEBS Lett.* 160: 131–34 (1990)). The physiological relevance for each of these candidate β-amyloid forming proteinases has not been demonstrated, for example, by concomitant inhibition of enzymatic activity with blocked β-amyloid protein formation.

Many proteinases have been reported as being altered in Alzheimer's disease brain tissue. For example, α-1-trypsin-like immunoreactivity has been shown to be increased in Alzheimer's disease brain (*Biochem. Biophys. Res. Comm. Vol.* 193(2): 579–84 (1993)), three different metalloproteinases have been reported as elevated in Alzheimer's disease brain (*J. Neurochem.* Vol. 58: 983–92 (1992)), multicatalytic proteinase alterations have been observed (*Neurosc. Res. Comm*, Vol. 8(3): 185–90 (1991)), abnormal cathepsin D and B immunoreactivity has been reported (*Neurosc. Lett.* 130: 195–98 (1991) and *Proc. Natl. Acad. Sci.* 87: 3861–65 (1990)), and calcium-activated neutral proteinase (calpain) has been variously shown to be decreased (*Neurobio. of Aging,* 11: 425–31 (1990)), increased (*Proc. Natl. Acad. Sci. USA* 90: 2628–32 (1993)), or to be unaltered (*J. Neurol. Sci,* 102: 220–34 (1991)) in Alzheimer's disease brain tissue.

The foregoing demonstrates that, although there has been a tremendous amount of work reported in this area, there is no general consensus as to classes of proteinases which are effective in treating Alzheimer's disease or if these proteinases are altered upon contact with Alzheimer's disease brain tissue.

It is an object of the present invention to provide compounds and pharmaceutical compositions, and methods for inhibiting the production of β-amyloid core protein and the formation of amyloid plaques in an individual suffering from dementia of the Alzheimer's type.

It is a further object of the invention to provide pharmaceutical compositions, and methods for treating or ameliorating the progression of Alzheimer's disease.

SUMMARY OF THE INVENTION

The present invention comprises compounds and the use of these compounds for treating conditions responsive to the inhibition or prevention of production of β-amyloid core protein in a patient. Some examples of these conditions are senile dementia of the Alzheimer's type and aged Down's syndrome disease.

The compounds in Formula IA are used in the treatment of senile dementia of the Alzheimer's type and aged Down's syndrome disease. However, some of these compounds have been previously disclosed for other uses. Therefore, Formula IB is also described which is a subset of Formula IA which is believed to describe compounds not previously disclosed. Formula IB differs from formula IA at the definition of $X^a$ and X in the provisos.

The compounds or the hydrate, stereoisomer, isostere or the pharmaceutically acceptable salt thereof are described in formulas IA which are used to treat senile dementia of the Alzheimer's type:

K—$P_4$—$P_3$—$P_2$—NH—CH(R)—[C(=O)]$_n$—X    IA
(SEQ ID NO:1)

wherein

X is H, $CHF_2$, $CF_3$, $CF_2F_3$, $CF_2CH_2NHC(=O)R_1$, $CHFCH_2NHC(=O)R_1$, $CF_2C(=O)W$, $C(=O)NHR_1$, $B(OH)_2$, or $C(=O)R_1$, wherein W is $NHCH_2$ $Si(C_{1-6}$ alkyl$)_2$ (Y), $NHR_1$ or $R_1$;

R is $C_{1-10}$ alkyl, benzyl, $CH_2$ $Si(C_{1-6}$ alkyl$)_2$ (Y), $C_{1-4}$ alkylene-O—$R_1$, $CH_2$ $CH(CF_3)_2$, $CH_2$ $CH(CH_3)(CF_3)$, $(CH_2)_m$-naphthyl, or a substituted benzyl, the substitution being 1, 2 or 3 substituents independently selected from the group consisting of $C_{1-6}$ alkyl, $C_{1-6}$ alkoxy, $C_{1-6}$ alkoxyalkyl, benzyloxy, hydroxy, NHC(=NH) $NH_2$, $NR_1H$, $NO_2$, —O—$(CH_2)_m$-aryl, $NHC(=O)R_1$ or halogeno, wherein m is 1 or 2;

Y is $C_{1-6}$ alkyl, $C_{1-6}$ alkenyl, aryl or arylalkyl;

n is 1 unless X is $B(OH)_2$ and then n is zero;

$R_1$ is H, $C_{1-6}$ alkyl, aryl or arylalkyl;

$P_2$ is a bond, or a residue of Leu, Ala, Met, Ile, Val, Nva, Nle, Phe, Asp, Ser, Pro, His, cyclopentylglycine, cyclohexylglycine, tert-leucine or —HN—CH[$CH_2$Si $(C_{1-6}$ alkyl$)_2$(X)]C(=O)—;

$P_3$ is a bond or a residue of Val, Leu, Ile or Met;

$P_4$ is a bond or a residue of Val, Leu, Ile or Met;

K is hydrogen, a desamino group, formyl, acetyl, succinyl, benzoyl, t-butyloxycarbonyl, carbobenzyloxy, tosyl, dansyl, isovaleryl, methoxysuccinyl, 1-adamantanesulphonyl, 1-adamantaneacetyl, 2-carboxybenzoyl, phenylacetyl, t-butylacetyl, bis [(1-naphthyl)methyl]acetyl, -A-$R_z$ wherein

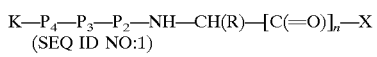

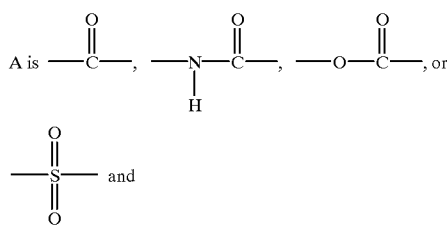

$R_z$ is an aryl or an arylalkyl in which the aryl group contains 6, 10 or 12 carbons, the aryl group being suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, 5-tetrazolyl, and acylsulfonamido (i.e., acylaminosulfonyl and sulfonylaminocarbonyl) containing from 1 to 15 carbons, provided that when the acylsulfonamido contains an aryl the aryl may be further substituted by a member selected from fluoro, chloro, bromo, iodo and nitro; and such other terminal amino protecting groups which are functionally equivalent thereto, or

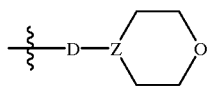

wherein
Z is N or CH, and
D is a group of the formulae

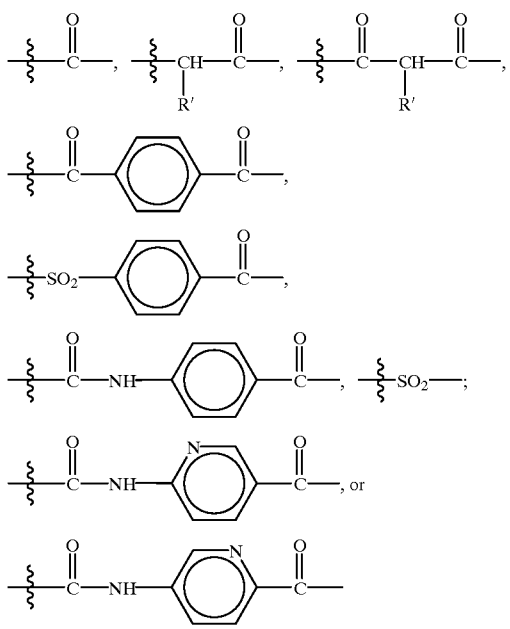

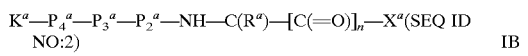

(the wavy line ⌇ being the attachment to the rest of the molecule, i.e., not to Z)
and wherein R' is hydrogen or a $C_{1-6}$ alkyl group, provided that X is not H, R is not benzyl, $P_2$ is not Val, $P_3$ is not a bond, $P_4$ is not a bond and K is not carbobenzyloxy, simultaneously. Theor preveunds are useful for inhibiting or preventing-the amyloid protein deposits in brain which are associated with Alzheimer's disease and Down's Syndrome.

A compound of the formula IB or the hydrate, stereoisomer, isostere or pharmaceutically acceptable salt thereof (which are believed to be compounds of formula IA which have not been previously disclosed):

$$K^a—P_4{}^a—P_3{}^a—P_2{}^a—NH—C(R^a)—[C(\!=\!O)]_n—X^a \text{(SEQ ID NO:2)} \quad \text{IB}$$

wherein
$X^a$ is H, $CHF_2$, $CF_3$, $CF_2F_3$, $CF_2$ $CH_2$ $NHC(\!=\!O)R_1{}^a$, $CHFCH_2NHC(\!=\!O)R_1{}^a$, $CF_2C(\!=\!O)W^a$, $C(\!=\!O)NHR_1{}^a$, $B(OH)_2$ or $C(\!=\!O)R_1{}^a$,
wherein $W^a$ is $NHCH_2Si(C_{1-6}alkyl)_2(y^a)$, $NHR_1{}^a$ or $R_1{}^a$;
provided that:
when $X^a$ is H, then $R^a$ is $CH_2Si(C_{1-6}\text{ alkyl})_2(C_{1-6}\text{alkenyl}$ or aryl), $CH_2CH(CF_3)_2$, $CH_2CH(CH_3)(CF_3)$, benzyl substituted with $NHC(\!=\!O)R_1{}^a$, or $NHC(\!=\!NH)NH_2$;

when $X^a$ is $CF_3$, $CHF_2$, or $C(\!=\!O)NHR_1{}^a$ then $R^a$ is not $C_{1-10}$alkyl, benzyl, $CH_2OH$, $CH(OH)CH_3$, or benzyl substituted with one hydroxy moiety;
when $X^a$ is $CF_2CH_2$ $NHC(\!=\!O)R_1{}^a$ then $R^a$ is not $C_{1-10}$ alkyl, benzyl, $(CH_2)_m$-napthyl or benzyl substituted with one hydroxy moiety;
when $X^a$ is $CF_2C(\!=\!O)NH$-benzyl then $R^a$ is not benzyl, t-butyl-methyl or $(CH_2)_m$-napthyl;
when $X^a$ is $CF_2C(\!=\!O)NHR_1{}^a$ then $R^a$ is not $CH_2Si(CH_3)_2(Y)$, $C_{1-10}$alkyl, benzyl, $CH_2OH$, $CH(OH)CH_3$, or benzyl substituted with one hydroxy moiety, $C_{1-6}$alkyl, $C_{1-6}$alkoxy, $C_{1-6}$alkyoxyalkyl, benzyloxy or —O—$(CH_2)_m$-phenyl;
when $X^a$ is $C(\!=\!O)R_1{}^a$ then $R^a$ is not $C_{1-10}$alkyl, benzyl, $C_{1-4}$alklylene-O-$C_{1-10}$alkyl, or $CH_2)_m$-napthyl;
when $X^a$ is $CF_2C(\!=\!O)$phenethyl then $R^a$ is not benzyl;
$X^a$ is not $C(\!=\!O)H$ when $R^a$ is $CH_2Si(C_{1-6}alkyl)_2(C_{1-6}alkenyl$ or aryl), $CH_2CH(CF_3)_2$, $CH_2CH(CH_3)(CF_3)$, or benzyl substituted with $NHC(\!=\!O)R_1{}^a$ or $NHC(\!=\!NH)NH_2$, $R^a$ is $C_{1-10}$ alkyl, benzyl, $CH_2Si(C_{1-6}\text{ alkyl})_2(Y^a)$, $C_{1-4}$ alkylene-O—$R_1{}^a$, $CH_2CH(CF_3)_2$, $CH_2CH(CH_3)(CF_3)$, $(CH_2)_m$-naphthyl, or a substituted benzyl, the substitution being 1, 2 or 3 substituents independently selected from the group consisting of $C_{1-6}$ alkyl, $C_{1-6}$ alkoxy, $C_{1-6}$ alkoxyalkyl, benzyloxy, hydroxy, $NHC(\!=\!NH)NH_2$, $NR_1{}^aH$, $NO_2$, —O—$(CH_2)_m$-aryl, $NHC(\!=\!O)R_1{}^a$ or halogeno, wherein m is 1 or 2;
$Y^a$ is $C_{1-6}$ alkyl, $C_{1-6}$ alkenyl, aryl or arylalkyl;
n is 1 unless $X^a$ is $B(OH)_2$ and then n is zero;
$R_1{}^a$ is hydrogen, $C_{1-6}$ alkyl, aryl or arylalkyl,
$P_2{}^a$ is a bond, —HN—CH[$CH_2Si(C_{1-6}$ alkyl$)_2(Y^a)$]C(=O)— or a residue of Leu, Ala, Met, Ile, Val, Nva, Nle, Phe, Asp, Ser, Pro, His, cyclopentyl-glycine, cyclohexylglycine, or tert-leucine;
$P_3{}^a$ is a bond or a residue of Val, Leu, Ile or Met;
$P_4{}^a$ is a bond or a residue of Val, Leu, Ile or Met;
$K^a$ is hydrogen, a desamino group, formyl, acetyl, succinyl, benzoyl, t-butyloxycarbonyl, carbobenzyloxy, tosyl, dansyl, isovaleryl, methoxysuccinyl, 1-adamantanesulphonyl, 1-adamantaneacetyl, 2-carboxybenzoyl, phenylacetyl, t-butylacetyl, bis[(1-naphthyl)methyl] acetyl, -$A^a$-$R_z{}^a$ wherein

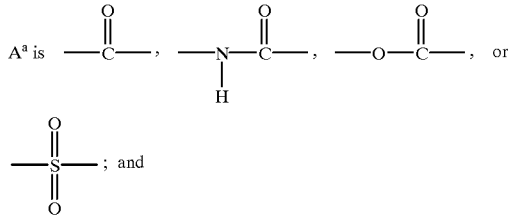

$R_z{}^a$ is an aryl or arylalkyl group in which the aryl group contains 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, 5-tetrazolyl, and acylsulfonamido (i.e., acylaminosulfonyl and sulfonylaminocarbonyl) containing from 1 to 15 carbons, provided that when the acylsulfonamido contains an aryl the aryl may be further substituted by a member selected from fluoro, chloro, bromo, iodo and nitro; and such other terminal amino protecting groups which are functionally equivalent thereto, or wherein

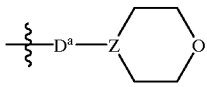

$Z^a$ is N or CH, and
$D^a$ is a group of the formulae

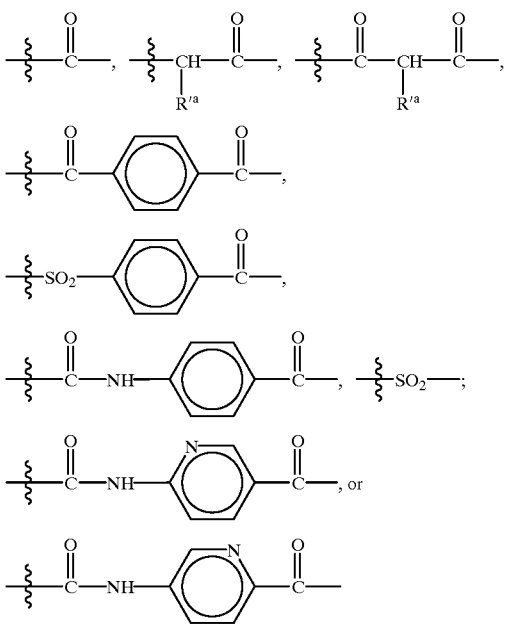

and wherein $R'^a$ is hydrogen or a $C_{1-6}$ alkyl group.

DETAILED DESCRIPTION OF THE INVENTION

A $C_{1-6}$ or $C_{1-10}$ alkyl group means straight, branched, cyclic alkyl groups or combinations thereof, for example, methyl, ethyl, propyl, isopropyl, butyl, isobutyl, tert-butyl, pentyl, isopentyl, sec-pentyl, cyclopentyl, hexyl, isohexyl, cyclohexyl, cyclohexylmethyl and cyclopentylmethyl. Likewise, $C_{1-6}$ alkylene and $C_{1-4}$ alkylene mean respectively a one to six and a one to four carbon bivalent radical which can be straight- or branched-chained. $C_{1-6}$ alkenyl has one to six carbons which are straight- or branched-chained with one or more double bonds. All of the $C_{1-10}$ moieties are preferably $C_{1-6}$ moieties and more preferably $C_{1-4}$ moieties. All of the $C_{1-6}$ moieties are preferably $C_{1-4}$ moieties and more preferably $C_{1-2}$ moieties.

The compounds of formula I having aspartic or glutamic acid moieties may be in free form or a salt form, e.g., acid addition or anionic salt. Such a compound may be converted into its salt or base form in an art-known manner, one from another. Preferred salts are trifluoroacetate, hydrochloride, sodium, potassium or ammonium salts, although the scope is extended to include all of the salts known to be used in the art of peptide chemistry.

The term "stereoisomer" is a general term for all isomers of individual molecules that differ only in the orientation of their atoms in space. It includes mirror image isomers (enantiomers), geometric (cis/trans) isomers, and isomers of compounds with more than one chiral center that are not mirror images of one another (diastereo-isomers). For amino-acids, the designations D/L or R/S can be used as described in IUPAC-IUB Joint Commission on Biochemical Nomenclature, Eur. J. Biochem. 138: 9–37 (1984). The natural amino acids, with the exception of glycine, contain a chiral carbon atom. Unless otherwise specifically indicated, the preferred compounds are the optically active amino acids of the L-configuration; however, applicants contemplate that the amino acids of the formula I compounds can be of either the D- or L-configurations or can be mixtures of the D- and L-isomers, including racemic mixtures. The recognized abbreviations for the α-amino acids are set forth in Table I.

As used herein "Alzheimer's Disease" also means senile dementia of the Alzheimer's type.

"Hydrate" means that the ketone of the compounds of this invention may exist as a di-hydroxymethylene group. The compounds of the present invention are expected to be in the hydrated form under normal physiological conditions.

"Desamino group" means an α-amino acid without the amino group attached thereto. Preferred desamino groups are represented by the alpha amino acids Val, Phe, Ala, Asp, Ser, and His, without their respective terminal amino groups.

"Isostere" means the normal peptide bond between attached amino acids (—C(O)NH—) is in a modified form of —CH$_2$NH— (reduced), C(O)N(CH$_3$) (N-methylamide), —COCH$_2$— (keto), —CH$_2$(OH)CH$_2$— (hydroxy), —CH(NH$_2$)CH$_2$— (amino), —CH$_2$CH$_2$— (hydrocarbon), or is inverted (—HN(C═O)—). Isostere as used herein also means an inversion of the C(═O)NH bond between an amino acid and the carbonyl moiety of the blocking group K. For example, Example 21 has two isostere groups: one isostere is between the blocking group (K═[C$_6$H$_5$—(CH$_2$)$_2$—C(═O)]— and the amino moiety of the valine residue, and the second isostere is between the valine residue and the phenylalanine aldehyde residue. Preferably the isostere only applies to the K-P$_4$-P$_3$-P$_2$-moiety or portions thereof. Most preferably the compounds of the present invention are not in isosteric forms.

"Aryl" means monocyclic or bicyclic carbocyclic ring systems having one or more aromatic rings including, but not limited to, phenyl, naphthyl, tetrahydronaphthyl, indanyl and the like. Aryl groups can be substituted or unsubstituted with one, two or three substituents independently selected from $C_{1-6}$ alkyl, haloalkyl, alkoxy, thioalkoxy, aminoalkylamino, dialkylamino, hydroxy, halo, mercapto, nitro, carboxaldehyde, carboxy, carboalkoxy and carboxamide. The above alkyl- and alkoxy compounds contain 1 to 6 carbons. Likewise, "arylalkyl" means a $C_{1-6}$ alkylene, straight or branched chain, appended to an aryl as defined herein, for example, benzyl.

"Substituted benzyl" means that a benzyl group is substituted at the phenyl moiety thereof at available carbon atoms, i.e., meta, ortho and/or para positions, having from one to three substituents. Preferably there is only one substituent, and more preferably that substituent is at the para position.

Each α-amino acid has a characteristic "R-group", the R-group being the side chain, or residue, attached to the α-carbon atom of the α-amino acid. For example, the R-group side chain for glycine is hydrogen, for alanine it is methyl, for valine it is isopropyl. For the specific R-groups or side chains of the α-amino acids see A. L. Lehninger's text on Biochemistry.

"(CH$_2$)$_m$-naphthyl" is a straight- or branched-chain alkylene attached to naphthyl at the 1- or 2-position thereof.

The natural amino acids, with the exception of glycine, contain a chiral carbon atom. Unless otherwise specifically indicated, the preferred compounds are the optically active amino acids of the L-configuration; however, applicants contemplate that the amino acids of the formula I compounds can be of either the D- or L-configurations or can be mixtures of the D- and L-isomers, including racemic mixtures. The recognized abbreviations for the α-amino acids are set forth in Table I.

TABLE I

| AMINO ACID | SYMBOL |
|---|---|
| Alanine | Ala |
| Glycine | Gly |
| Isoleucine | Ile |
| Leucine | Leu |
| Lysine | Lys |
| Serine | Ser |
| Arginine | Arg |
| Threonine | Thr |
| Asparagine | Asn |
| Valine | Val |
| Norvaline | Nva |
| Norleucine | Nle |
| Glutamic acid | Glu |
| Cysteine | Cys |
| Histidine | His |

Note that even though formula IB has an "a" superscript to all of its variables, the only difference between formulae IA and IB is at X and X$^a$ in the provisos. The following schemes are directed to variables which do not have an "a" superscript but are used to describe the synthesis for both formulae IA and IB.

In general, the compounds of formula I may be prepared using standard chemical reaction analogously known in the art and as depicted in Scheme A.

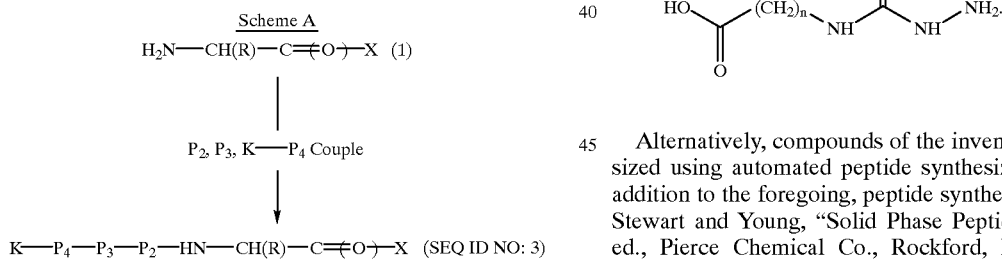

Scheme A provides a general synthetic scheme for preparing the compounds of formula I.

The P$_2$, P$_3$ and K-P$_4$ groups can be linked to the free amino group of the amino acid derivative of structure (1). The P$_2$, P$_3$ and K-P$_4$ can be linked to the unprotected, free amino compound by well known peptide coupling techniques.

Generally, peptides are elongated by deprotecting the α-amine of the C-terminal residue and coupling the next suitably protected amino acid through a peptide linkage using the methods described. This deprotection and coupling procedure is repeated until the desired sequence is obtained. This coupling can be performed with the constituent amino acids in stepwise fashion, as depicted in Scheme A, or by condensation of fragments (two to several amino acids), or combination of both processes, or by solid phase peptide synthesis according to the method originally described by Merrifield, *J. Am. Chem. Soc.*, 1963, 85, 2149–2154, the disclosure of which is hereby incorporated by reference. When a solid phase synthetic approach is employed, the C-terminal carboxylic acid is attached to an insoluble carrier (usually polystyrene). These insoluble carriers contain a group which will react with the aldehyde group to form a bond which is stable to the elongation conditions but readily cleaved later. Examples of which are chloro- or bromomethyl resin, hydroxymethyl resin, and aminomethyl resin. Many of these resins are commercially available with the desired C-terminal amino acid already incorporated. For compounds of formula I wherein X is H, a linker compound may also be used in the reaction of Scheme A to link a resin to the aldehyde functionality of the amino acid derivative of structure (1) wherein X is H. Examples of suitable linker compounds are

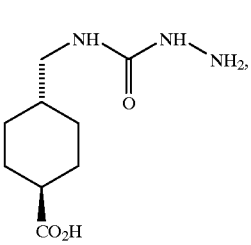

L1

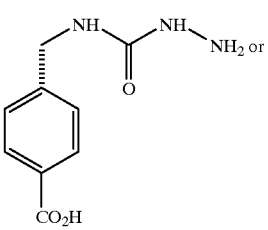

L2

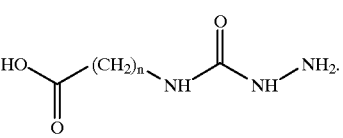

L3

Alternatively, compounds of the invention can be synthesized using automated peptide synthesizing equipment. In addition to the foregoing, peptide synthesis are described in Stewart and Young, "Solid Phase Peptide Synthesis", 2nd ed., Pierce Chemical Co., Rockford, Ill. (1984); Gross, Meienhofer, Udenfriend, Eds., "The Peptides: Analysis, Synthesis, Biology", Vol 1, 2, 3, 5 and 9, Academic Press, New York, 1980–1987; Bodanszky, "Peptide Chemistry: A Practical Textbook", Springer-Verlag, New York (1988); and Bodanszky, et al. "The Practice of Peptide Synthesis" Springer-Verlag, New York (1984), the disclosures of which are hereby incorporated by reference.

Coupling between two amino acids, an amino acid and a peptide, or two peptide fragments can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinic imido ester) method, Woodward reagent K method, carbonyldiimidazole method, phosphorus reagents such as BOP-Cl, or oxidation-reduction methods. Some of these methods (especially the carbodiimide method) can be enhanced by adding 1-hydroxybenzotriazole. These coupling reactions can be performed in either solution (liquid phase) or solid phase.

The functional groups of the constituent amino acids must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), the disclosure of which is hereby incorporated by reference.

The α-carboxyl group of the C-terminal residue is usually protected by an ester that can be cleaved to give the carboxylic acid. Protecting groups which can be used include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters.

The α-amino group of each amino acid must be protected. Any protecting group known in the art can be used. Examples of which include: 1) acyl types such as formyl, trifluoroacetyl, phthalyl, and p-toluenesulfonyl; 2) aromatic carbamate types such as benzyloxycarbonyl (Cbz or Z) and substituted benzyloxycarbonyls, 1-(p-biphenyl)-1-methylethoxy-carbonyl, and 9-fluorenylmethyloxycarbonyl (Fmoc); 3) aliphatic carbamate types such as tertbutyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl;; 5) alkyl types such as triphenylmethyl and benzyl; 6) trialkylsilane such as trimethylsilane; and 7) thiol containing types such as phenylthiocarbonyl and dithiasuccinoyl. The preferred α-amino protecting group is either Boc or Fmoc, preferably Fmoc. Many amino acid derivatives suitably protected for peptide synthesis are commercially available.

The α-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or insitu with basic solutions such as aqueous buffers, or tertiary amines in dichloromethane or dimethylformamide. When the Fmoc group is used, the reagents of choice are piperidine or substituted piperidine in dimethylformamide, but any secondary amine or aqueous basic solutions can be used. The deprotection is carried out at a temperature between 0° C. and room temperature.

Any of the amino acid bearing side chain functionalities must be protected during the preparation of the peptide using any of the above-described groups. Those skilled in the art will appreciate that the selection and use of appropriate protecting groups for these side chain functionalities depends upon the amino acid and presence of other protecting groups in the peptide. The selection of such protecting groups is important in that it must not be removed during the deprotection and coupling of the α-amino group.

For example, when Boc is used as the a-amino protecting group, the following side chain protecting groups are suitable: p-toluenesulfonyl (tosyl) moieties can be used to protect the amino side chains of amino acids such as Lys and Arg; p-methylbenzyl, acetamidomethyl, benzyl (Bzl), or t-butylsulfonyl moieties can be used to protect the sulfide containing side chains of amino acids such as cysteine; and benzyl (Bzl) ether can be used to protect the hydroxy containing side chains of amino acids such as Ser or Thr.

When Fmoc is chosen for the a-amine protection usually tert-butyl based protecting groups are acceptable. For instance, Boc can be used for lysine, tert-butyl ether for serine and threonine and tert-butyl ester for glutamic acid.

Once the elongation of the peptide is completed all of the protecting groups are removed. When a solution phase synthesis is used, the protecting groups are removed in whatever manner is dictated by the choice of protecting groups. These procedures are well known to those skilled in the art.

When a solid phase synthesis is used, the peptide is cleaved from the resin usually simultaneously with the protecting group removal. When the Boc protection scheme is used in the synthesis, treatment with anhydrous HF containing additives such as dimethyl sulfide, anisole, thioanisole, or p-cresol at 0° C. is the preferred method for cleaving the peptide from the resin. The cleavage of the peptide can also be accomplished by other acidic reagents such as trifluoromethanesulfonic acid/trifluoroacetic acid mixtures. If the Fmoc protection scheme is used the N-terminal Fmoc group is cleaved with reagents described earlier. The other protecting groups and the peptide are cleaved from the resin using a solution of trifluoroacetic acid and various additives such as anisole, etc.

For those compounds of formula I wherein X is H, the peptide compound of formula I may be cleaved from the linker compound and resin with aqueous acid/formaldehyde.

Alternatively, the compounds of formula I may be prepared using standard chemical reactions analogously known in the art and as depicted in Scheme B.

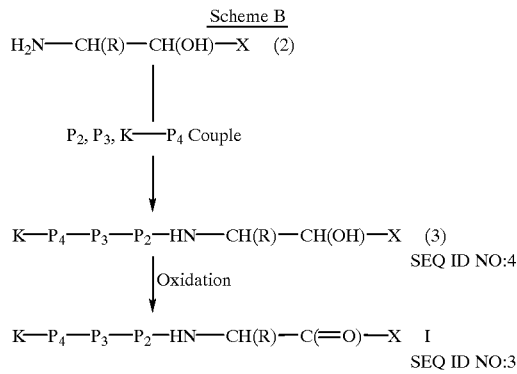

Scheme B provides an alternative general synthetic scheme for preparing the compounds of formula I.

The $P_2$, $P_3$ and $K-P_4$ groups can be linked to the free amino group of the amino alcohol derivative of structure (2) as described previously in Scheme A to give the peptido alcohol of structure (3).

The alcohol functionality of the peptido alcohol of structure (3) is then oxidized by techniques and procedures well known and appreciated by one of ordinary skill in the art, such as a Swern Oxidation using oxalyl chloride and dimethylsulfoxide, to give the compounds of formula I.

Starting materials for use in Schemes A and B are readily available to one of ordinary skill in the art. For example, amino acids $P_2$, $P_3$ and $K-P_4$ wherein K is hydrogen are commercially available and the linker compound of structure (L1) is described in *J. Am. Chem. Soc.*, 114, 3157–59 (1992). In addition, substituted amino acids $K-P_4$ wherein K is acetyl, succinyl, benzoyl, t-butyloxycarbonyl, carbobenzyloxy, tosyl, dansyl, isovaleryl, methoxysuccinyl, 1-adamantanesulphonyl, 1-adamantaneacetyl, 2-carboxbenzoyl, phenylacetyl, t-butylacetyl, bis [(1-naphthyl)methyl]acetyl or -A-R$_z$ wherein

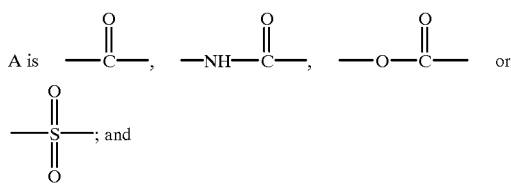

Rz is an aryl group containing 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, 5-tetrazolyl, and acylsulfonamido (i.e., acylaminosulfonyl and sulfonylaminocarbonyl) containing from 1 to 15 carbons, provided that when the acylsulfonamido contains an aryl the aryl may be further substituted by a member selected from fluoro, chloro, bromo, iodo and nitro; and such other terminal amino protecting groups which are functionally equivalent thereto are described in European Patent Application No. 0363284, Apr. 11, 1990.

Starting amino compounds of formula (1) are readily available to one of ordinary skill in the art. For example, certain protected amino compounds of Formula IA wherein:

X is H and R is benzyl is described in European Patent Application No. 0363284 and WO84/00365;

X is H and R is CH$_2$Si(CH$_3$)$_3$ is described in European Patent Application No. 0363284 and described herein in Examples 12. As described in Example 13 and 14, substituents on the silyl can be different;

X is H and R is substituted benzyl is described in Patent Application PCT/US91/09741;

X is CF$_3$ and CHF$_2$, and R is benzyl or benzyl substituted with NHC(NH)NH$_2$ are described in European Patent Application No. 0195212 with a publication date of Sep. 24, 1986, inventors Michel Jung et al.;

X is CF$_2$CH$_2$NHC($=$O)R1 and R is benzyl is described as an intermediate in European Patent Application OPI No. 0275101, filed Jan. 14, 1988, inventors Daniel Schirlin et al.; the monofluoro derivative CFHCH$_2$NHC($=$O)R1 can be synthesized by similar methods using bromo-fluoroacetic acid, ethyl ester in place of bromo-difluoroacetic acid, ethyl ester;

X is CF$_2$C(O)W wherein W is NHCH$_2$Si(alkyl)$_3$ and R is benzyl, CH$_2$Si(CH$_3$)$_3$ or substituted benzyl are described in Patent Application No. PCT/US91/09741, inventors Daniel Schirlin et al., filed Dec. 20, 1991, and when R is (CH$_2$)$_m$-naphthyl similar methods may be used with starting materials well known in the art;

X is CF$_2$C(O)W wherein W is NHR1 or R1 and R is benzyl, CH$_2$Si(CH$_3$)$_3$ or substituted benzyl are described in Patent Application No. PCT/US91/09741, inventors Daniel Schirlin et al., filed Dec. 20, 1991, and when R is (CH$_2$)$_m$-naphthyl similar methods may be used with starting materials well known in the art;

X is C(O)R1 and R is benzyl, CH$_2$Si(CH$_3$)$_3$, (CH$_2$)$_m$-naphthyl or substituted benzyl are described in U.S. Pat. No. 4,820,691, filed Apr. 11, 1989; and The linker compound trans-4-(aminomethylcyclohexane)carboxylic acid, benzyl ester used in the synthesis of compound of formula I wherein X is H is prepared from the corresponding acid as described in *J. Am. Chem. Soc.* 1992, 114, 3156–3157.

All of the foregoing cites are hereby incorporated herein by reference.

In addition, other starting materials for use in Schemes A and B may be prepared by the following synthetic procedures which are well known and appreciated by one of ordinary skill in the art.

Substituted amino acids K-P$_4$ of structure wherein K is

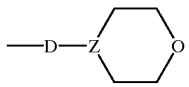

wherein

Z is N or CH, and

D is a group of the formulae

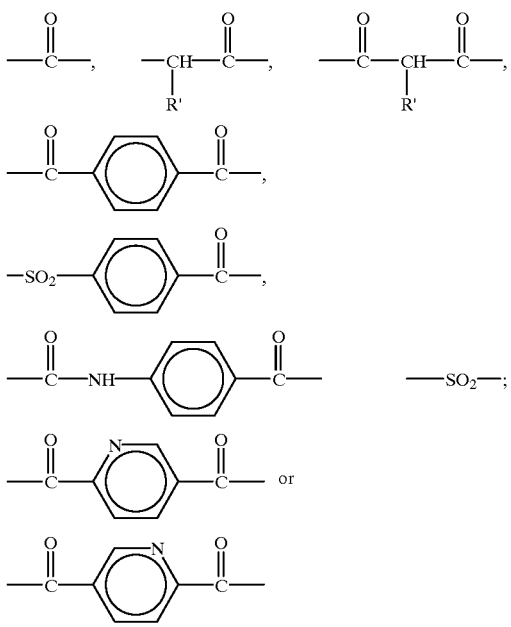

wherein R' is hydrogen or a C$_{1-6}$ alkyl group are prepared using standard chemical reactions analogously known in the art.

The procedure for preparing the substituted amino acids K-P$_4$ wherein K is

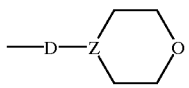

wherein

D is a —C($=$O)— is outlined in Scheme B wherein P$_4$ and Z are as previously defined or are the functional equivalents of these groups.

Scheme C

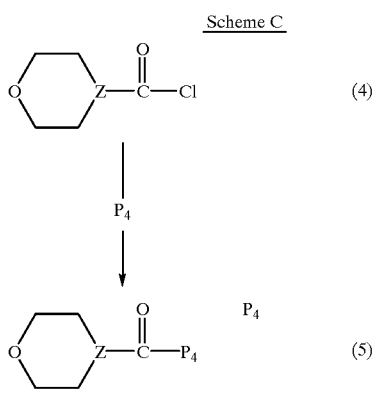

Specifically the amino acids K-P₄ wherein K is

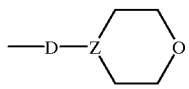

wherein
D is a —C(=O)—are prepared by coupling of the amino acid K-P₄ wherein K is hydrogen with acid chloride of structure (4) in the presence of from one to four molar equivalents of a suitable amine which can act as a hydrogen halide acceptor. Suitable amines for use as hydrogen halide acceptors are tertiary organic amines such as tri-(lower alkyl)amines, for example, triethylamine, or aromatic amines such as picolines, collidines, and pyridine. When pyridines, picolines, or collidines are employed, they can be used in high excess and act therefore also as the reaction solvent. Particularly suitable for the reaction is N-methylmorpholine ("NMM"). The coupling reaction can be performed by adding an excess, such as from 1–5, preferably about a 4-fold molar excess of the amine and then the acid chloride of structure (4), to a solution of the amino acid K-P₄ wherein K is hydrogen. The solvent can be any suitable solvent, for example, petroleum ethers, a chlorinated hydrocarbon such as carbon tetrachloride, ethylene chloride, methylene chloride, or chloroform; a chlorinated aromatic such as 1,2,4-trichlorobenzene, or o-dichlorobenzene; carbon disulfide; an ethereal solvent such as diethylether, tetrahydrofuran, or 1,4-dioxane, or an aromatic solvent such as benzene, toluene, or xylene. Methylene chloride is the preferred solvent for this coupling reaction. The reaction is allowed to proceed for from about 15 minutes to about 6 hours, depending on the reactants, the solvent, the concentrations, and other factors, such as the temperature which can be from about 0° C. to about 60° C., conveniently at about room temperature, i.e. 25° C. The amino acids K-P₄ wherein K is

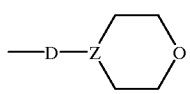

wherein
D is a —C(=O)— can be isolated from the reaction mixture by any appropriate techniques such as by chromatography on silica gel.

The substituted amino acids K-P₄ wherein K is

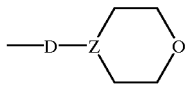

wherein
D is other then a —C(=O)—can be prepared analogously, merely by substituting the appropriate intermediate

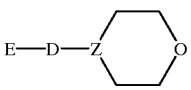

wherein
D is other than a —C(=O)—and E is Cl or OH (the corresponding acid, acid chloride or sulphonyl chloride) for the compound of structure (5) in Scheme C.

The acid chloride of structure (4) and the appropriate intermediate of formula

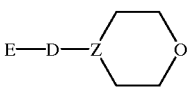

wherein
B is other then a —C(=O)— and E is Cl or OH (the corresponding acid, acid chloride or sulphonyl chloride) are commercially available or may be readily prepared by techniques and procedures well known and appreciated by one of ordinary skill in the art.

For example, the appropriate intermediates of formula

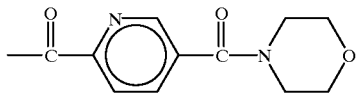

may be prepared as outlined in Scheme D wherein all substituents are as previously defined.

Scheme D

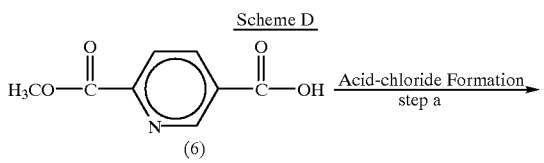

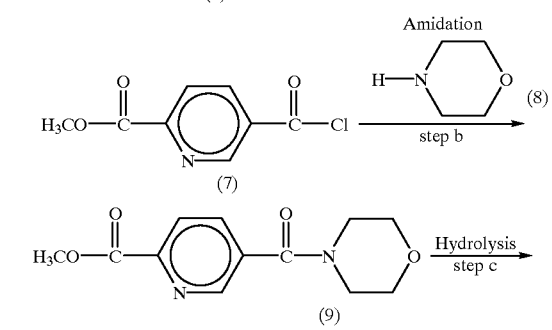

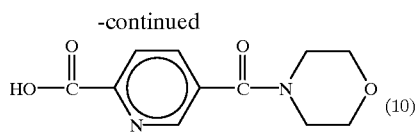
(10)

Scheme D provides a general synthetic procedure for preparing the appropriate intermediates of formula

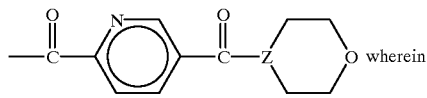 wherein

Z is as previously defined.

In step a, carboxylic acid functionality of the appropriate 2,5-pyridinedicarboxylic acid, 2-methyl ester (6) (*Nippon Kagaku Zasshi,* 1967, 88, 563) is converted to its acid chloride using techniques and procedures well known and appreciated by one of ordinary skill in the art, such as thionyl chloride, to give the corresponding 2,5-pyridinedicarboxylic acid, 2-methyl ester, 5-acid chloride (7)

In step b, the 2,5-pyridinedicarboxylic acid, 2-methyl ester, 5-acid chloride (7) is amidated with morpholine (8) by techniques and procedures well known and appreciated by one of ordinary skill in the art to give the corresponding 2,5-pyridinedicarboxylic acid, 2-methyl ester, 3-morpholino amide (9).

In step c, the methyl ester functionality of 2,5-pyridinedicarboxylic acid, 2-methyl ester, 3-morpholino amide (9) is hydrolyzed by techniques and procedures well known and appreciated by one of ordinary skill in the art, with for example, lithium hydroxide in methanol, to give the 2,5-pyridinedicarboxylic acid, 5-morpholino amide (10).

In addition, the appropriate intermediate of formula

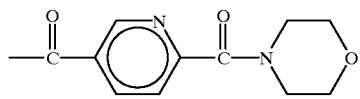

may be prepared as outlined in Scheme E wherein all substituents are as previously defined.

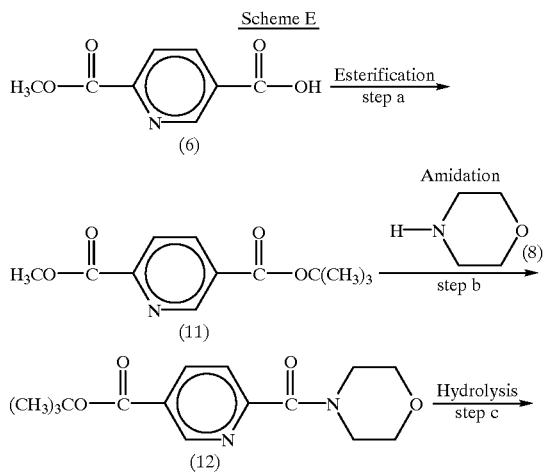

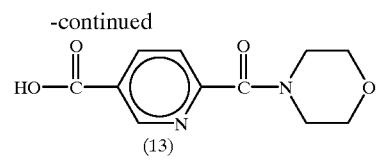
(13)

Scheme E provides a general synthetic procedure for preparing the appropriate intermediates of formula

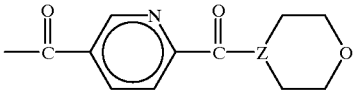

wherein

Z is as previously defined.

In step a, the free carboxylic acid functionality of 2,5-pyridinedicarboxylic acid, 2-methyl ester (6) (*Nippon Kagaku Zasshi,* 1967, 88, 563) is converted to its t-butyl ester using techniques and procedures well known and appreciated by one of ordinary skill in the art, such as the t-butyl alcohol adduct of dicyclohexylcarbodiimide (*Synthesis,* 1979, 570), to give the corresponding 2,5-pyridinedicarboxylic acid, 2-methyl ester, 5-t-butyl ester (11).

For example, the 2,5-pyridinedicarboxylic acid, 2-methyl ester (6) is reacted with a molar excess of the t-butyl alcohol adduct of dicyclohexylcarbodiimide in an appropriate organic solvent, such as methylene chloride. The reaction is typically conducted at a temperature range of from 0° C. to room temperature and for a period of time ranging from 2–24 hours. The 2,5-pyridinedicarboxylic acid, 2-methyl ester, 5-t-butyl ester (11) is isolated from the reaction zone by standard extractive methods as is known in the art. and may be purified by crystallization.

In Step b, the methyl ester functionality of 2,5-pyridinedicarboxylic acid, 2-methyl ester, 5-t-butyl ester (11) is amidated with morpholine (8) to give the corresponding 2,5-pyridinedicarboxylic acid, 2-morpholino amide, 5-t-butyl ester (12).

For example, the 2,5-pyridinedicarboxylic acid, 2-methyl ester, 5-t-butyl ester (11) is contacted with molar excess of morpholine in an appropriate organic solvent, such as tetrahydrofuran. The reaction is typically conducted at a temperature range of from room temperature to reflux and for a period of time ranging from 5 hours to 3 days. The 2,5-pyridinedicarboxylic acid, 2-morpholino amide, 5-t-butyl ester (12) is isolated from the reaction zone by standard extractive methods as is known in the art. and may be purified by crystallization.

In step c, the t-butyl ester functionality of 2,5-pyridinedicarboxylic acid, 2-morpholino amide, 5-t-butyl ester (12) is hydrolyzed, with for example, HCl in nitromethane, to give the corresponding, 2,5-pyridine-dicarboxylic acid, 2-morpholino amide (13).

In general, the compounds of formula IA may be prepared using standard chemical reactions analogously known in the art. For example, a synthesis of the compounds of formula IA where X is H is depicted in Scheme F. All the substituents, unless otherwise indicated, are as previously defined. The reagents and starting materials are readily available to one of ordinary skill in the art.

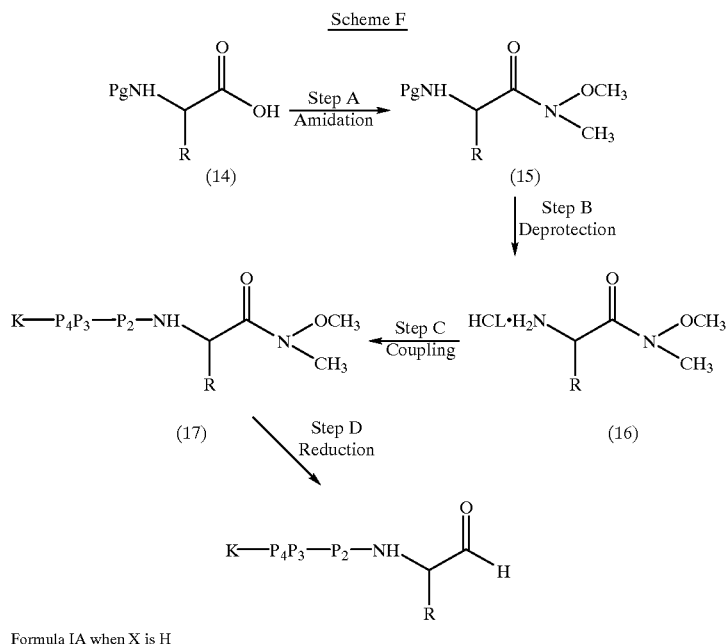

The required starting material defined by compound (14) is readily available either commercially or by applying known prior art principles and techniques. The term "Pg" refers to a suitable protecting group as more fully defined previously. Examples of such compounds are the suitably protected amino acids serine, homoserine, threonine, allo-threonine and the like. In addition, L-lysine can be transformed into 2(S)-2-amino-6-hydroxyhexanoic acid following generally the procedure described by Baldwin, J. E. et al., *Tetrahedron*, 44, 2633 (1988), incorporated herein.

In Scheme F, Step A the protected amino acid (14) is transformed into the amide (15). This amidation can be performed utilizing a coupling reaction as between two amino acids using the protected amino acid (14) and the N-alkyl O-alkylhydroxylamine. The standard coupling reaction can be carried out using standard coupling procedures as described previously for the coupling between two amino acids to provide the amide (15).

In Scheme F, Step B the amide (15) is deprotected under conditions well known in the art as described by T. H. Green, "Protective Groups in Organic Synthesis", John Wiley and Sons, 1981, Chapter 7, to provide the deprotected amide (16). For example, when "Pg" is a t-butyloxycarbonyl (Boc), the amide (15) is dissolved in a suitable solvent, such as ethyl acetate treated with excess hydrogen chloride (gas) and stirred at about 0° C. to 30° C. for about 30 minutes to 4 hours. The solvent is then removed under vacuum to provide the deprotected amide (16) as the HCl salt.

In Scheme F, Step C the deprotected amide (16) is elongated by coupling the next suitably protected amino acid through a peptide linkage using the methods previously described in Scheme A, or by condensation of fragments, or combination of both processes to provide the elongated peptide (17).

In Scheme F, Step D the elongated peptide (17) is reduced to provide the desired aldehyde of formula IA.

For example, the elongated peptide (17) is dissolved in a suitable organic solvent, such as tetrahydrofuran and cooled to 0° C. under an atmosphere of nitrogen. An excess of a suitable reducing agent is added to the solution. Examples of suitable reducing agents are lithium aluminum hydride, diisobutylaluminum hydrides, tri-tert-butyloxy-aluminum hydrides, sodium aluminum hydrides, diamino-aluminum hydrides and the like. The preferred reducing agent is lithium aluminum hydride. The reaction is stirred for 20 minutes to 2 hours at a temperature of about 0° C. to 20° C. The reaction is then quenched and the product isolated by techniques well known in the art. For example, the reaction is quenched with 10% potassium hydrogen sulfate followed by addition of 10% hydrochloric acid. The aqueous mixture is then extracted with a suitable organic solvent, such as ethyl acetate. The organic extract is washed with water, dried over magnesium sulfate, filtered and concentrated under vacuum to provide the aldehyde of formula IA.

The compounds of formula IA, wherein X is C(=O)NHR$_1$ can be prepared following the procedure described in Scheme F. All the substituents, unless otherwise indicated, are previously defined. The reagents and starting materials are readily available to one of ordinary skill in the art.

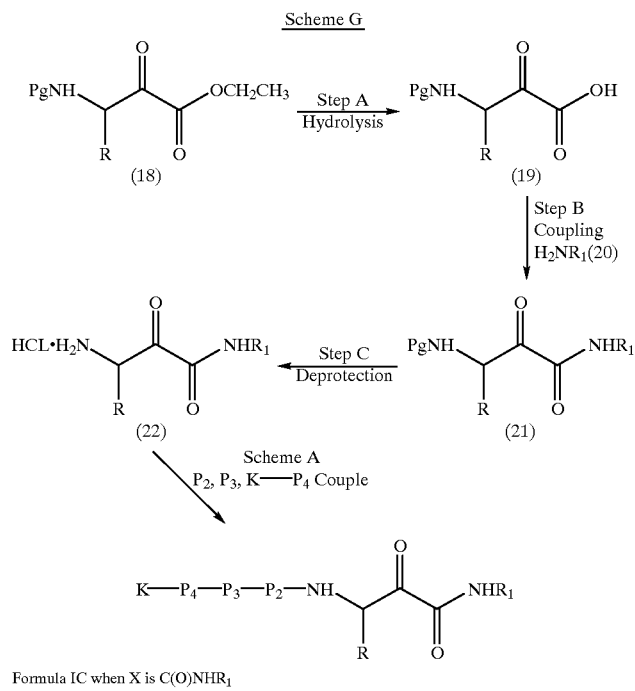

Formula IC when X is C(O)NHR₁

In Scheme G, Step A, the α-keto ester (18) is selectively hydrolyzed to the α-keto acid (19) by treatment with a suitable base. [The α-keto ester (18) is readily prepared following generally the procedure described by Angelastro, M. R. et al., *J. Med. Chem.*, 33, 11 (1990).]

For example the appropriately substituted α-keto ester (18) is dissolved in a suitable solvent mixture, such as methanol:water (50:50) and treated with an equivalent of a suitable base, such as lithium hydroxide. The reaction is stirred at a temperature of about 0° C. to 30° C. for about 1 to 10 hours. The α-keto acid (19) is then isolated by extractive techniques well known in the art. For example, the reaction is diluted with a suitable organic solvent, such as ethyl acetate and an equal volume of water. The layers are separated. The aqueous layer is acidified with dilute hydrochloric acid and extracted with a suitable organic solvent, such as ethyl acetate. The combined organic extracts are dried over anhydrous magnesium sulfate, filtered and concentrated under vacuum to provide the α-keto acid (19).

In Scheme G, Step B the α-keto acid (19) is coupled with a primary amine (20) under conditions well known in the art to provide the desired a-keto amide (21).

For example, the appropriately substituted α-keto acid (19) is dissolved in a suitable organic solvent, such as methylene chloride. The solution is then treated with one equivalent of 1-hydroxybenzotriazole, one equivalent of diisopropylethylamine and one equivalent of a primary amine (20). An equivalent of dicyclohexylcarbodiimide is added and the reaction is stirred at a temperature of about 0° C. to 25° C. for about 2 to 10 hours. The product is then isolated by techniques well known in the art. For example, the reaction is diluted with ethyl acetate, rinsed with cold 0.5 N hydrochloric acid, saturated sodium bicarbonate, dried over anhydrous magnesium sulfate, filtered and concentrated under vacuum to provide the α-keto amide (21).

In Scheme G, Step C the α-keto amide (21) is deprotected under conditions well known in the art as described by T. H. Green, "Protective Groups in Organic Synthesis", John Wiley and Sons, 1981, Chapter 7, to provide the deprotected a-keto amide (22). For example, when "Pg" is a t-butyloxycarbonyl (Boc), the α-keto amide (21) is dissolved in a suitable solvent, such as ethyl acetate treated with excess hydrogen chloride (gas) and stirred at about 0° C. to 30° C. for about 30 minutes to 4 hours. The solvent is then removed under vacuum to provide the deprotected a-keto amide (22) as the HCl salt.

The deprotected α-keto amide (22) is then subjected to the reaction conditions described in Scheme A to provide the compounds of formula IA wherein X is C(=O)NHR₁.

In formula IA, wherein X is B(OH)₂, the following general scheme may be followed (other starting materials where R is other than benzyl may be used as is well knwon in the art):

Scheme H

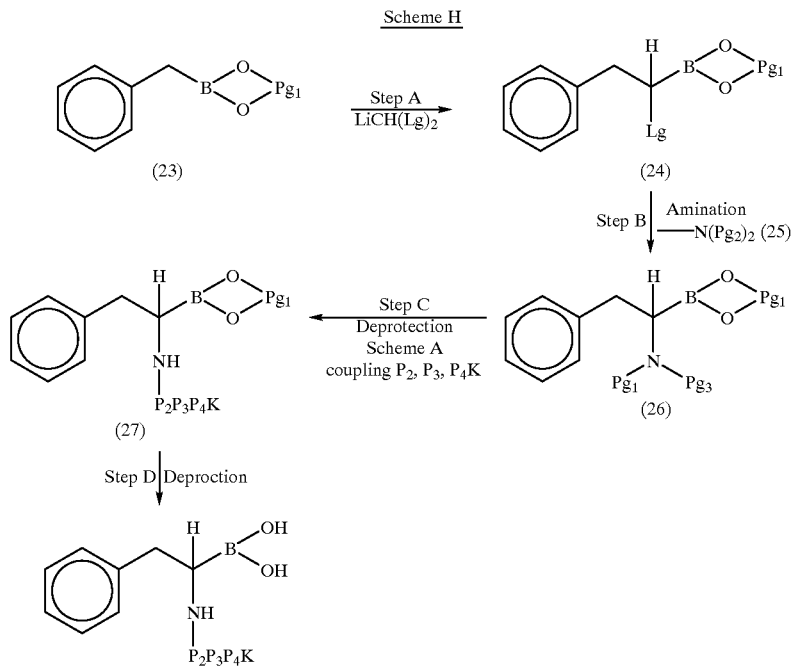

Formula IC wherein X = B(OH)2

In Scheme H, the boronic acid derivative (23) is protected by a protecting group ($Pg_1$), which can be cyclic (e.g., $Pg_1$=pinane) or two separate protecting groups.

In Step A, a homologation occurs and a leaving group (Lg) such as chloride is introduced. Then, in Step B, the boronate (24) is aminated. The amine (25) is preferably protected with any two protecting groups ($Pg_2$ and $Pg_3$). For example, see descriptions in *J. Am. Chem. Soc.* 1981, 103: 5241–5242. In Step C, the amine may be deprotected as previously described herein or as well known in the art. Coupling in Step C may occur as previously described in Scheme A. The boronate moiety of the coupled compound (27) may then be deprotected by well known means (see *J. Am. Chem. Soc.*, 1981, 103: 5241–5242 for an example of the foregoing reactions).

In order to incorporate a substituent of the following type: $NR_1H$, the starting material in Scheme I should be in a protected form as follows:

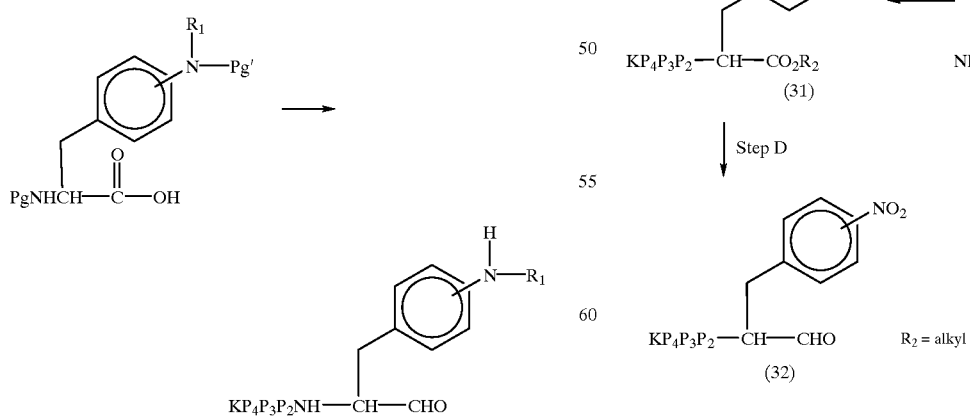

When the substituent on the benzyl (R side chain) is $NO_2$, the following scheme is preferred Scheme I

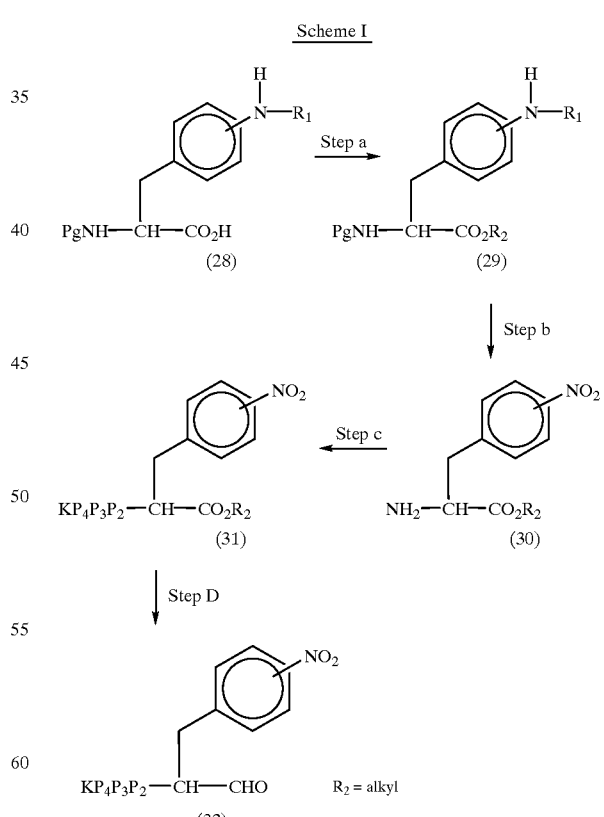

In step a, the —$NO_2$ phenylalanine derivative is converted to an ester using techniques and procedures well known and appreciated by one of ordinary skill in the art, such as methanol in presence of dicyclohexylcarbodiimide and 4-dimethyl aminopyridine.

In step b, the ester (29) is deprotected under conditions well known in the art as described by T. H. Green, "Protective Groups in Organic Synthesis", John Wiley and Sons, 1981, Chapter 7, to provide the deprotected ester (30).

In step c, the deprotected ester (30) is elongated by coupling the next suitably protected amino acid through a peptide linkage using the methods previously described in Scheme I, or by condensation of fragments, or combination of both processes to provide the elongated peptide (31).

In step d, the elongated peptide (31) is reduced to aldehyde (32) using techniques and procedures well known and appreciated by one of ordinary skill in the art, such as diisobutylaluminum hydride (Dibal) in a toluene/diethyl ether mixture at low temperature (—78° C. to -50° C.).

Compounds of formula IA with X being $CHF_2$ or $CF_3$, can be prepared according to scheme J.

For those compounds wherein X is either —$CF_2H$ or —$CF_3$, intermediates for the application of the standard peptide coupling techniques are compounds of formula IIa–b

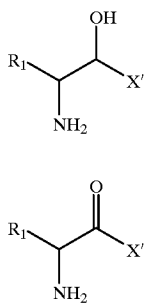

wherein X' is —$CF_3$ or —$CF_2H$, and R is as previously defined in formula IA. Similarly, designations $P_1$, $P_2$, $P_3$, $P_4$, and K shown in the foregoing schemes are as defined in formula IA, except that any subgeneric or other modifications thereof (as in X) are highlighted by the use of a primed symbol with a specific designation for such modified symbol. The preparation and application of these compounds are depicted in scheme J.

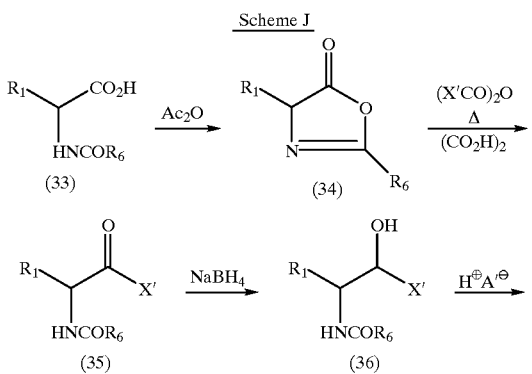

Scheme J

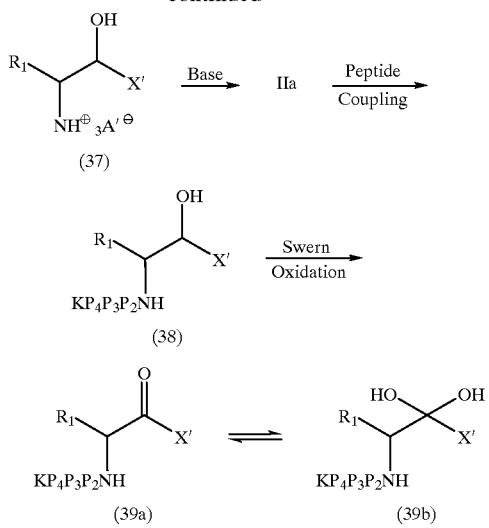

wherein $R_6$ is alkyl, phenyl or other equivalent moiety, and X' is —$CF_2H$ or —$CF_3$,. H⊖A'⊖ means an acid.

In general the formation of the substituted azlactones (34) is effected from the N-protected amino acids (33) by standard reaction conditions wherein the amino acid derivative (33) is heated in the presence of an acid anhydride. The so-produced azlactone (34) is reacted with a di- or trifluoroacetic acid anhydride or acid halide to give a fluorinated intermediate which (with or without isolation) is treated with anhydrous oxalic acid to produce the N-protected fluorinated ketone (35) whereupon the ketone is chemically reduced to its alcoholic amide (36). The amide (36) is cleaved under standard acidic conditions to yield its amide acid salt [e.g., its hydrochloride (37)]. After neutralization, the alcohols (IIa) may be coupled to $KP_4P_3P_2OH$ using standard peptide chemistry techniques to produce compounds (38) which are subjected to the Swern oxidation procedure to obtain the desired product (39a) and (39b) (the ketone or hydrate respectively). Alternatively, the alcohols (IIa) may be oxidized to the ketones (IIb) which are coupled to $KP_4P_3P_2OH$ according to standard peptide chemistry techniques. When employing this alternative route, the amino moiety is first protected with a Boc protecting group, the OH function oxidized to its ketone via Swern oxidation procedures, and then the Boc protecting group removed and the resulting compounds (IIb) are the coupled to $KP_4P_3P_2OH$.

Scheme J is also applicable for the preparation of compounds of formula IA wherein X is $CF_2CF_3$, the substituted azlactones (34) being heated in the presence of pentafluoropropanoic acid anhydride or acid halide.

An alternate route for the preparation of compounds of formula IA wherein X=$CF_2CF_3$, is shown in scheme K.

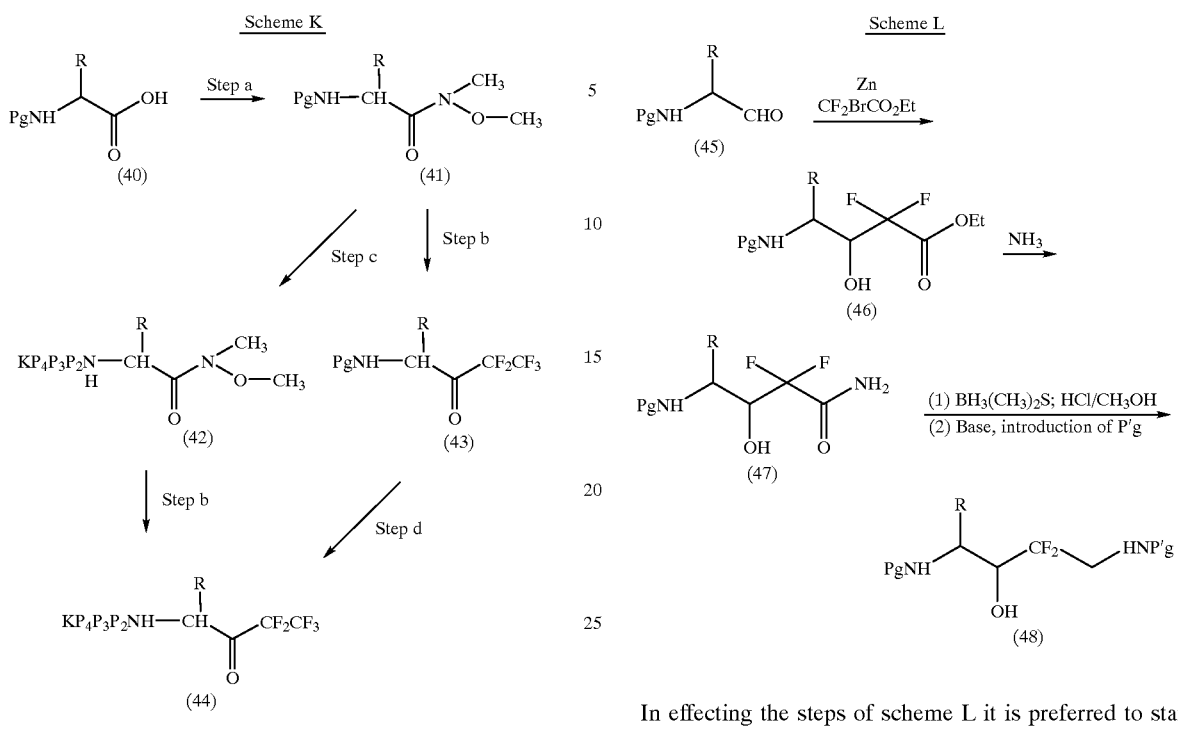

Scheme K / Scheme L

In step a the protected amino acid (40) is transformed into the hydroxamate (41). This amidation can be performed utilizing a coupling reaction as between two amino acids using the protected amino acid (40) and the N-alkyl O-alkylhydroxylamine. The standard coupling reaction can be carried out using standard coupling procedures as described previously for the coupling between two amino acids to provide the hydroxamate (41).

In step b, the protected hydroxamate (41) is transformed into the protected pentafluoroketone (43) [or (44)]. This reaction can be performed utilizing a coupling reaction of the type described in the following reference M. R. Angelastro, J. P Burkhart, P. Bey, N. P. Peet, *Tetrahedron Letters,* 33 (1992), 3265–3268.

In step c, the hydroxamate (41) is deprotected under conditions well known in the art as described by T. H. Green "Protection Groups in Organic Synthesis", John Wiley and Sons, 1981, Chapter 7, to provide the deprotected hydroxamate (41). The deprotected hydroxamate (41) is elongated by coupling the next suitably protected amino acid through a peptide linkage using the methods previously described in Scheme K, or by condensation of fragments, or combination of both processes to provide the elongated peptide (42).

In step d, the ketone (43) is deprotected under conditions as previously described. The deprotected ketone (43) is elongated by coupling the next suitably protected amino acid through a peptide linkage using the methods previously described in Scheme K, or by condensation of fragments, or combination of both processes to provide the elongated ketone (43).

For the preparation of compounds of formula IA wherein X is $CF_2CH_2NHCOR_1$ the following schemes may be used.

In effecting the steps of scheme L it is preferred to start with the aldehyde (45) wherein the protecting group is a carbamate preferably wherein Pg is benzyloxycarbonyl (CBZ). This so-protected aldehyde is subjected to a condensation reaction with an ester of bromodifluoroacetic acid, preferably the ethyl ester in the presence of zinc. Preferably the reaction is conducted in an anhydrous aprotic solvent, e.g., tetrahydrofuran, ether, dimethoxy-ethane and the like under a nitrogen atmosphere. The reaction mixture is gently heated under reflux conditions, preferably to about 60° C. for about 1–12 hours. The ester (46) is converted to its primary amide ((47) by treatment with liquid ammonia under anhydrous conditions, preferably using such solvents as anhydrous diethyl ether. The amidation is initiated at −78° C. and following saturation with ammonia the reaction mixture is slowly allowed to rise to room temperature. The so-formed amide is chemically reduced to form the free amine. This chemical reduction is easily effected by reacting the amide with a diborane, preferably as a diborane/dimethylsulfide complex, under a nitrogen atmosphere in an anhydrous aprotic solvent (e.g., THF) under reflux conditions. The reduction yields the desired amine, in the form of an acid (e.g., HCl) salt which, by pH adjustment, yields the free amine which may be suitably protected with an N-protecting group, e.g., P'g is t-butoxy carbonyl using the standard reaction conditions (e.g., $(BOC)_2O$, THF at room temperature) for protection the amine. Alternatively the free amine may be subjected to reaction conditions designed to build the desired a-amino acid or peptide moiety on the P' side of the difluoro-methylene moiety.

Having obtained the intermediates of formula (48) standard α-amino acid or peptide coupling procedures may be conducted to prepare the individual compounds of formula IA. In practice it is more convenient to effect coupling on the P' side of the difluoromethylene moiety.

For compounds of formula IA wherein X is $CF_2CH_2NHCOR_1$, the following scheme M should be used.

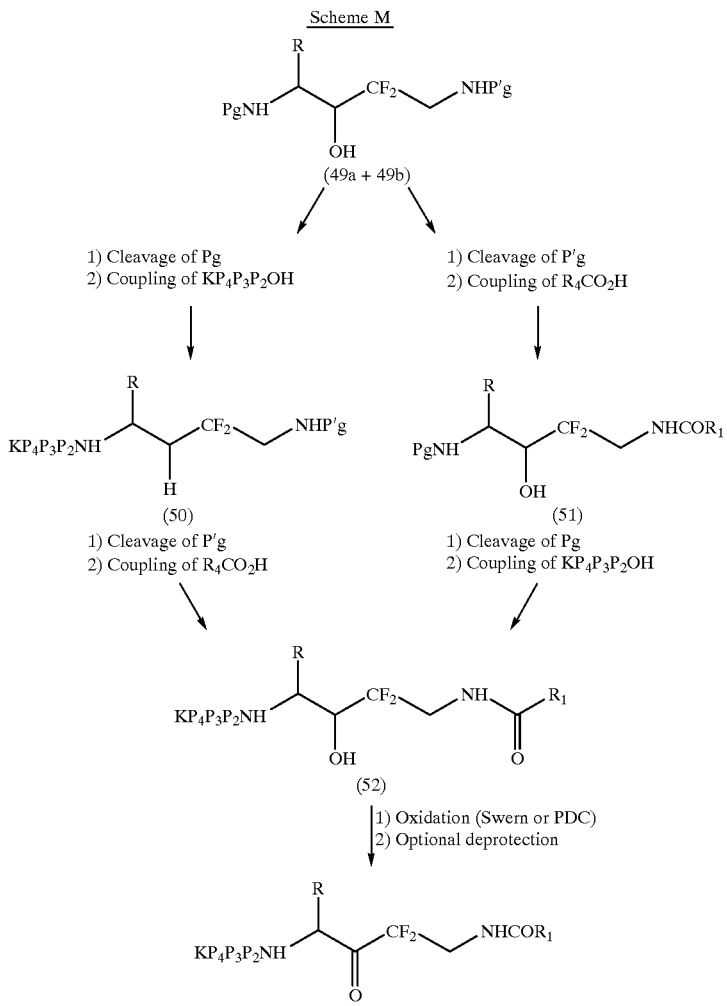

The oxidation step may be effected via the well known Swern oxidation procedure, or with a modified Jones reaction using pyridinium dichromate, or a chromic anhydride pyridinium complex, or with 1,1,1-triacetoxy-2,1-benzoxiodol (Dess-Martin reagent).

For the preparation of compounds of formula IA wherein X is $CHFCH_2NHCOR_1$, scheme L could be used, the first step being a condensation reaction between aldehyde (45) and an ester of bromofluoroacetic acid, preferably ethyl ester in the presence of zinc. Preferably, the reaction is conducted in an anhydrous aprotic solvent (THF, ether, dimethoxyethane) and under nitrogen. Conditions are as described for scheme L.

For the preparation of compounds of formula IA wherein X is $CF_2(C=O)W$ and W is $NHCH_2Si(C_{1-6}alkyl)_2(B)$ or $NHR_1$, scheme N may be used.

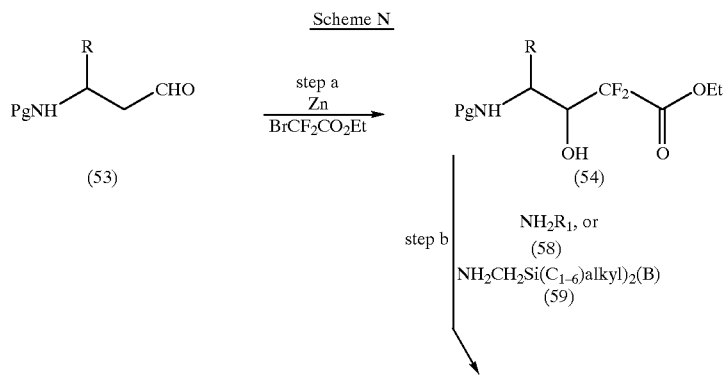

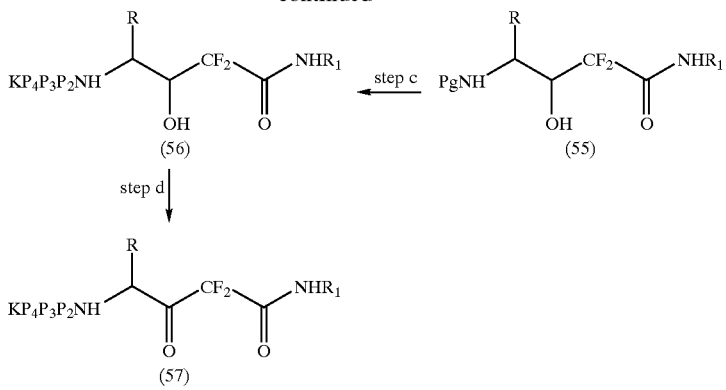

Step a is similar to scheme L step a, and applicable to all side chains of the present invention. Ester (54) in scheme N is converted to the secondary amide (55) by treatment with the corresponding primary amines (58) or (59) under anhydrous conditions, preferably using such solvents as THF. The amidation is initiated at 0° C. or at room temperature and the reaction mixture might be heated to reflux for completion of the reaction.

In step c, the so-formed amide (55) is deprotected under conditions similar to the one described in scheme F, step b. The deprotected amide is elongated by coupling the next suitably protected amine and through a peptide linkage using the methods previously described in scheme A or by condensation of fragments, or by combination of both processes to provide the elongated peptide (56).

In step d the alcohol functionality of the alcohol(56) is then oxidized by techniques and procedures well known and appreciated of one ordinary skill in the art, such as Swern oxidation using oxalyl chloride and dimethyl-sulfoxide, to give the compounds of formula (58).

For compounds of formula IA wherein X is $CF_2C(=O)W$ and $W=R_1$, the following scheme may be used.

temperature (preferably 0° C.) to chlorodifluorodimethylhydroxamate (60).

In step a', chlorodifluoromethy ketones (61) are preferably prepared by addition of an organometallic derivative of type $MR_1$(derived from $R_1$halogeno) (preferably Li or Mg) in an inert solvent under anhydrous conditions (e.g., THF) at low temperature (preferably −20° C.) to chlorodifluoroacetic acid (60a)

The aforementioned ketone (61) is added to a mixture of zinc, titanium tetrachloride and desired aldehyde* at 0° C. under nitrogen in THF.

In step c, the alcohol functionality of the peptido alcohol of structure (62) is then oxidized by techniques and procedures well known and appreciated by one of ordinary skill in the art, such as a Swern oxidation using oxalyl chloride and dimethylsulfoxide, to give the compounds of formula (63). Reference: D. Schirlin et al., *Bioorg. and Medicinal Chem. Letters,* 3 (1993), 253–258.

The following examples present typical syntheses. These examples are understood to be illustrative only and are not intended to limit the scope of the present invention in any

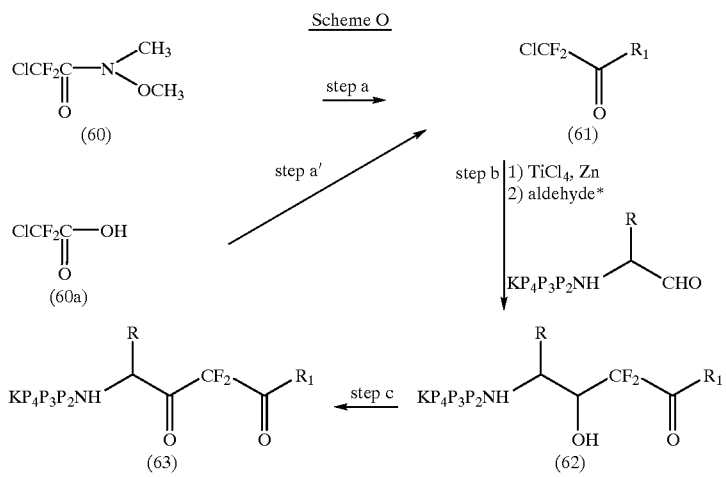

* previously described

In step a, chlorodifluoromethy ketones (61) are preferably prepared by addition of an organometallic derivative of type $MR_1$(derived from $R_1$halogeno) (preferably Li or Mg) in an inert solvent under anhydrous conditions (e.g., THF) at low way. As used herein, the following terms have the indicated meanings: "g" refers to grams; "mmol" refers to millimoles; "mL" refers to milliliters; "bp" refers to boiling point; "° C" refers to degrees Celsius; "mm Hg" refers to millimeters of mercury; "μL" refers to microliters; "μg" refers to micrograms; and "μM" refers to micromolar; "Z" or "Cbz" means carbobenzyloxy; "THF" means tetrahydrofuran; "DCU" means N,N-dichlorourethane; "Eq" means equivalent; "Atg" means gram atoms.

EXAMPLE 1

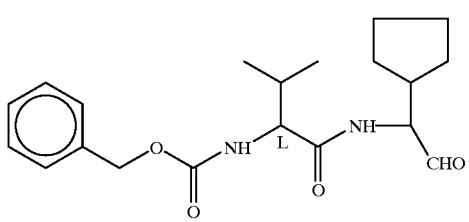

Preparation of Benzyloxycarbonyl-L-valyl-cyclopentyl glycinal

Step A: Benzyloxycarbonyl-cyclopentyl glycinol

A solution of borane-dimethylsulfide complex (1 M in dichloromethane, 2.4 mL) is added dropwise under an atmosphere of nitrogen to a well stirred solution of CbZ-cyclopentylglycine (0.336 g, 1.2 mmol) in 3 mL of anhydrous tetrahydrofuran. The resulting solution is stirred at room temperature for 16 hours. Water (1 mL) is carefully added and the mixture evaporated. The oily residue is dissolved in ethyl acetate and the solution washed with saturated solutions of citric acid, sodium bicarbonate, and brine. The organic layer is dried over magnesium sulphate, filtered, and evaporated to afford 0.2 g (60%) of the alcohol as an oil. $R_f$=0.25 (silica gel, ethyl acetate: petroleum ether 3:1) MS: MH$^+$=264.

Step B: Cyclopentyl glycinol

A mixture of the alcohol of Example 1, Step A (0.74 mmol) and 0.05 g of palladium hydroxide on carbon (Pearlman's catalyst, 10%) in 20 mL of isopropanol is hydrogenated at room temperature and atmospheric pressure for 16 hours. Filtration from the catalyst and evaporation of the filtrate affords 0.076 g (80%) of the unprotected amino alcohol.

Step C: Benzyloxycarbonyl-L-valyl-cyclopentylglycinol

A solution of cyclopentylglycinol (0.065 g, 0.5 mmol) in 5 mL dichloromethane is added to a solution of benzyloxycarbonyl-L-valyl-0-benzotriazolyl ester [prepared by usual activation of Cbz-valine (0.13 g, 0.5 mmol) with hydroxy-benzotriazole (0.077 g, 0.5 mmol), dicyclohexyl carbodiimide (0.103 g, 0.5 mmol) and N-methyl morpholine (0.101 g, 1 mmol)] in 5 mL of anhydrous dichloromethane. The resulting mixture is stirred for 16 hours at room temperature and filtered. The filtrate is evaporated and the oily residue dissolved in ethyl acetate. The solution is washed with saturated solutions of citric acid, sodium bicarbonate, and brine. Drying over MgSO$_4$ and evaporation of solvents give 0.13 g of a pale yellow oil which is subjected to flash chromatography on silica gel (ethyl acetate: petroleum ether 1:1, $R_f$=0.2). Evaporation of the pooled product-containing fractions yields 0.13 g (70%) of the dipeptide alcohol as an oil. MS: MH$^+$=363.

Step D: Benzyloxycarbonyl-L-valyl-cyclopentyl glycinal

A mixture of the above dipeptide alcohol (0.086 g, 0.24 mmol), Dess-Martin periodinane (0.2 g, 0.48 mmol), and 4 mL of anhydrous dichloromethane is stirred at room temperature for 2 hours. Isopropanol (1 mL) is added and the solution evaporated to dryness. The solid residue is applied to flash chromatography (silica gel, ethyl acetate: petroleum ether 1:7, $R_f$=0.3). Evaporation of the pooled, product-containing fractions affords 0.038 g (47%) of the title compound as a solid.

Anal. Calcd for C$_{20}$OH$_{28}$O$_4$N$_2$.025 H$_2$O: C, 65.90; H, 7.74; N, 7.68. Found: C, 66.04; H, 7.62; N, 7.66.

EXAMPLE 2

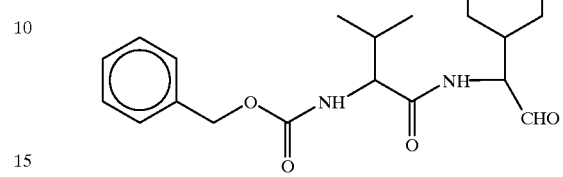

Preparation of Benzyloxycarbonyl-L-valyl-cyclohexyl glycinal

Step A: 2-cyclohexylglycinol

A mixture of L-phenylglycine (0.96 g, 7 mmol), 0.1 g of 5% rhodium on charcoal, and 50 mL acetic acid is hydrogenated at room temperature under a pressure of 8 bar for 48 hours. After filtration from the catalyst the solution is evaporated to dryness (several evaporations with carbon tetrachloride as cosolvent) to give an oil. Treatment of this oil with a saturated hydrochloric acid gas-ether solution and evaporation of solvent affords the title compound as a white solid (0.1.26 g, 100%).

Step B: Benzyloxycarbonyl-L-valyl-cyclohexyl glycinol

The title compound is obtained in 47% yield from the compound of Example 2, Step A, and benzyloxycarbonyl-L-valine using the coupling procedure described in Example 1, Step C. $R_f$=0.3 (silica gel, ethyl acetate: petroleum ether 4:6)

Anal. Calcd for C$_{21}$H$_{32}$ $_{O4}$N$_2$: C, 66.99; H, 6.57; N, 7.44 Found: C, 67.17; H, 6.76; N, 7.61.

Step C: Benzyloxycarbonyl-L-valyl-cyclohexyl glycinal

The title aldehyde is obtained in 78% yield from the alcohol of Example 2, Step B, using the Dess-Martin oxidation procedure described in Example 1, Step D. $R_f$=0.5 (silica gel, ethyl acetate:petroleum ether 2:3) MS: MH$^+$=375

Anal. Calcd for C$_{21}$H$_{30}$N$_2$O$_4$0.0.25 H$_2$O: C, 66.55; H, 6.11; N, 7.39 Found; C, 66.35; H, 6.12; N, 7.56.

EXAMPLE 3

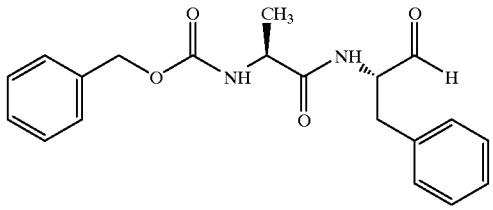

Preparation of CBz-L-Ala-L-Phe-H

Dissolve CBz-Ala-Phe-OH (0.5 g, 1.4 mmol) in methylene chloride (10 mL). Add N,N'-diisopropylethylamine (DIEA, 0.23 mL) and cool the solution to 0° C. Add bis(2-oxo-3-oxazolidinyl) phosphinic chloride (BOP-Cl, 0.34 g), N,O-Dimethylhydroxylaminee●HCl (0.15 g, 1.5 mmol) and DIEA (0.46 mL) to the reaction. Stir for 2 hours and then pour into water. Extract the aqueous with ethyl acetate, dry the combined organic extracts over anhydrous sodium sulfate, filter and concentrate under vacuum. Purify the residue by flash chromatography (30% ethyl acetate/ hexane, silica gel) to provide the hydroxamate (0.23 g).

Dissolve the above prepared hydroxamate (16 g) in diethyl ether (10 mL) and cool the solution to 0° C. Add lithium aluminum hydride (0.20 g) and stir the reaction at −2° C. for 25 minutes. Then quench the reaction by dropwise addition of 10% aqueous potassium hydrogen sulfate and pour into water (100 mL). Extract the aqueous with diethyl ether (3×50 mL). Combine the organic extracts, dry over anhydrous sodium sulfate, filter and concentrate under vacuum. Purify the residue by flash chromatography (30% ethyl acetate/hexane, silica gel) to provide the title compound (0.05 g).

EXAMPLE 4

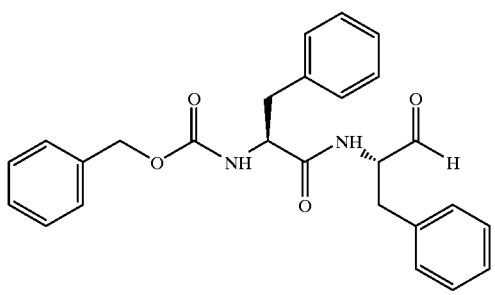

Preparation of CBz-L-Phe-L-Phe-H

Dissolve CBz-Phe-Phe-OH (2.14 g, 4.8 mmol, obtained from Bachem Bioscience) and N-methylmorpholine (1.6 mL, 14.4 mmol) in methylene chloride (22 mL). Cool the solution to −22° C. and add isobutyl chloroformate (0.62 mL, 4.8 mmol). Stir the reaction for 30 minutes and add N,O-dimethylhydroxylaminee●HCl (0.6 g, 6.2 mmol). Stir the reaction for 45 minutes at −22° C. and then warm to room temperature and stir overnight. Pour the reaction into dilute aqueous hydrochloric acid and extract the aqueous with diethyl ether (2×200 mL). Combine the organic extracts and wash with saturated sodium bicarbonate, saturated sodium chloride, dry over anhydrous sodium sulfate, filter and concentrate under vacuum to provide the hydroxamate (1.81 g).

Dissolve the above prepared hydroxamate (1.0 g, 2.0 mmol) in THF (60 mL) and cool the solution to 0° C. Add lithium aluminum hydride (0.21 g, 5.5 mmol) and stir the reaction for 40 minutes. Then quench the reaction by dropwise addition of 10% aqueous potassium hydrogen sulfate (approximately 3 mL). Pour the reaction mixture into water (300 mL). Extract the aqueous phase with diethyl ether (2×200 mL), dry the combined organic extracts over anhydrous sodium sulfate, filter and concentrate under vacuum. Crystallize the residue from ethyl acetate/hexane to provide the title compound (0.25 g).

EXAMPLE 5

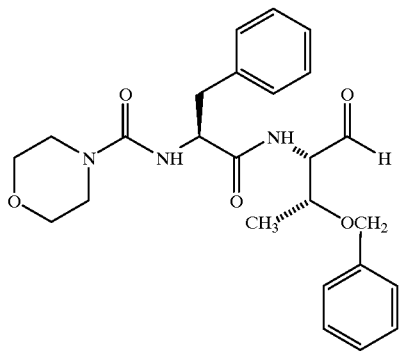

Preparation of N-(N-Morpholylcarbonyl)-L-phenylalanyl-L-(O-benzyl) threoninal amide Dissolve Boc-Thr(Bn)-OH (5.00 g, 16.3 mmol, obtained from Bachem Bioscience) in methylene chloride (65 mL). Then add consecutively 1-hydroxybenzotriazole hydrate (2.20 g, 16.3 mmol), N,O-dimethylhydroxylamine●HCl (1.59 g, 16.3 mmol), N-methylmorpholine (1.79 mL, 16.3 mmol) and 1-(3-dimethylmorpholinel) 3-ethylcarbodiimide●HCl (3.10 g, 16.3 mmol). Stir the reaction for 1 hour under an atmosphere of nitrogen. Then dilute the reaction with 10% aqueous hydrochloric acid (200 mL) and extract with methylene chloride (135 mL). Wash the separated organic layer with 10% aqueous hydrochloric acid (100 mL), saturated sodium bicarbonate (100 mL), saturated sodium chloride (100 mL), dry over anhydrous magnesium sulfate, filter and concentrate under vacuum to provide the desired hydroxamate (4.83 g) as a clear colorless oil.

Dissolve the above prepared hydroxamate (4.80 g, 13.6 mmol) in ethyl acetate (270 mL) and cool the solution to 0° C. under an atmosphere of nitrogen. Bubble hydrogen chloride (gas) through the solution for 50 minutes. Then bubble nitrogen through the solution as it warms to room temperature. Concentrate under vacuum, add hexane (100 mL) and again concentrate under vacuum to provide the HCl salt of the amide (3.64 g) as a white foam.

Dissolve Boc-Phe-OH (3.22 g, 12.12 mmol) in methylene chloride (48 mL). Add consecutively 1-hydroxybenzotriazole hydrate (1.64 g, 12.12 mmol), the above prepared HCl salt of the hydroxamate (3.50 g, 12.12 mmol), N-methylmorpholine (1.23 mL, 12.12 mmol) and 1-(3-dimethylaminopropyl)-3-ethylcarbodiimide●HCl (2.23 g, 12.12 mmol) and stir the reaction overnight at room temperature under an atmosphere of nitrogen. Then dilute the reaction with methylene chloride (100 mL) and add 10% aqueous hydrochloric acid (150 mL). Separate the layers and wash the organic layer with 10% aqueous hydrochloric acid (2×75 mL), saturated sodium bicarbonate (2×75 mL), saturated sodium chloride (75 mL), dry over anhydrous magnesium sulfate, filter and concentrate under vacuum to provide the coupled amide (5.19 g) as a white foam.

Dissolve the above prepared coupled amide (5.00 g, 10.01 mmol) in ethyl acetate (200 mL) and cool the solution to 0° C. under an atmosphere of nitrogen. Bubble hydrogen chloride (gas) through the solution for 1 hour. Then bubble nitrogen through the solution as it warms to room temperature. Concentrate under vacuum, add hexane (100 mL) and again concentrate under vacuum. Dry the residue over potassium hydroxide to provide the HCl salt of the coupled amide (quantitative yield).

Dissolve the above prepared HCl salt of the coupled amide (0.750 g, 1.72 mmol) in methylene chloride (34 mL). Add morpholine chloride (0.399 mL, 3.44 mmol) and N-methylmorpholine (0.389 g, 3.44 mmol). Stir the reaction at room temperature under an atmosphere of nitrogen for approximately 2 hours. Concentrate the reaction under vacuum and purify the residue by flash chromatography (80% ethyl acetate/acetone, silica gel) to provide the morpholine carboxamide (0.430 g) as a white foam.

Dissolve the above prepared morpholine carboxamide (0.4 g, 0.780 mmol) in THF (7.8 mL) and cool to 0° C. under an atmosphere of nitrogen. Add lithium aluminum hydride (36.9 g, 0.975 mmol) and stir the reaction for 1 hour at 0° C. Quench the reaction by addition of 10% potassium hydrogen sulfate add ethyl acetate (20 mL) and 10% aqueous hydrochloric acid (20 mL). Separate the layers and wash the organic layer with 10% aqueous hydrochloric acid (2×15 mL), saturated sodium bicarbonate (15 mL), saturated sodium chloride (15 mL), dried over anhydrous magnesium sulfate, filtered and concentrated under vacuum to provide the title compound (0.264 g) as a white foam.

EXAMPLE 6

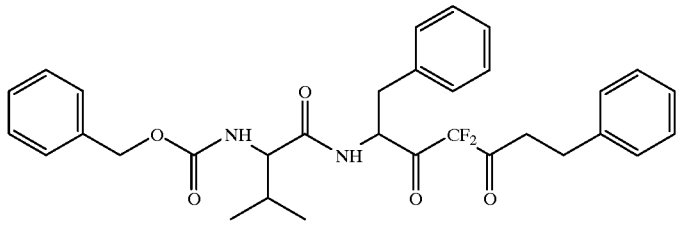

Preparation of 2-(N-Benzyloxycarbonyl-L-valyl)amino-4,4-difluoro-1,7-diphenyl-3,5-dioxoheptane Step A : N-Benzyloxycarbonyl-L-valyl-L-phenylalanine, N,O-dimethyl hydroxamate Add N,N'-dicyclohexylcarbodiimide (0.920 g, 4.5 mmol) to a solution of CBz(L)-Val-Phe-OH (0.220 g, 0.55 mmol) and hydroxybenzotriazole (0.93 g, 0.61 mmol) in methylene chloride (12 mL). Stir at 0° C. for 1 hour. Add N,O-dimethyl-hydroxylamine●HCl (0.59 g, 0.61 mmol) and N-methylmorpholine (0.61 g, 0.61 mmol) to the reaction and stir at 25° C. for 12 hours. Filter the mixture, wash with methylene chloride and concentrate the filtrate under vacuum to provide the crude amide as an oil. Purify the crude residue by flash chromatography (silica gel, 2:8 ethyl acetate:cyclohexane) to provide the title compound (0.250 g).

Step B: N-Benzyloxycarbonyl-L-valyl-L-phenylalaninal

Add the above prepared hydroxamate (0.220 g, 5 mmol) to a solution of lithium aluminum hydride (0.19 g, 0.49 mmol) in diethyl ether (10 mL) at 0° C. under inert atmosphere. Stir for 30 minutes, allow the reaction to warm to room temperature and stir for 1 hour. Separate the phases and wash the organic phase with saturated sodium carbonate (10 mL), saturated sodium chloride, dry over magnesium sulfate, filter and concentrate under vacuum to provide the title compound CBz(L)-Val-Phe-H (0.179 g) used without further purification.

Step C: 2-(N-Benzyloxycarbonylvalyl)amino-4,4-difluoro-1,7-diphenyl-3-hydroxy-5-oxoheptane Add titanium tetrachloride (0.019 g, 0.1 eq) to a suspension of activated zinc (0.196 g, 3mAtg) in anhydrous THF (3 mL) at 0° C. under nitrogen. Stir 30 minutes and add CBz(L)-Val-Phe-H (0.42 g, 1.1 mmol), 1-chloro-1,1-difluoro-2-oxo-4-phenylbutane (0.218 g, 1.1 mmol), in anhydrous THF (4 mL). Allow the reaction to warm to room temperature and stir for 12 hours. Add a saturated solution of ammonium chloride (2 mL). Extract two times with diethyl ether (4 mL) and wash the organic phase with brine and dry over anhydrous magnesium sulphate. Concentrate the organic phase under vacuum. Purify the crude residue by flash chromatography (silica gel, 3:7 ethyl acetate:cyclohexane) to provide the title alcohol (0.381 g).

Step D: 2-(N-Benzyloxycarbonyl-L-valyl)amino-4,4-difluoro-1,7-diphenyl-3,5-dioxoheptane Add dimethylsulfoxide (0.331 g, 4.26 mmol) to a solution of oxalyl chloride (0.269 g, 2.13 mmol) in anhydrous methylene chloride (2 mL) at −55° C. under nitrogen. Stir for ten minutes at −55° C. and add the above prepared alcohol (0.3 g, 0.53 mmol) in anhydrous methylene chloride (2 mL). Stir the reaction 2 hours at this temperature and allow the reaction to warm to −20° C. Add triethylamine (0.321 g, 1.68 mmol) and allow the reaction to warm to room temperature. Stir the mixture an additional few minutes. Dilute with ethyl acetate (10 mL). Wash the organic phase with hydrochloric acid (3×3 mL, 0.1N) and saturated aqueous ammonium chloride. Dry the organic phase over anhydrous magnesium sulfate, filter and concentrate under vacuum to provide the crude compound (0.22 g).

Purification of the crude material by crystallization provides the title compound (0.102 g).

Anal. Calcd: 67.95; H, 6.24; N, 4.95. Found: C, 66.99; H, 6.15; N, 5.30.

EXAMPLE 7

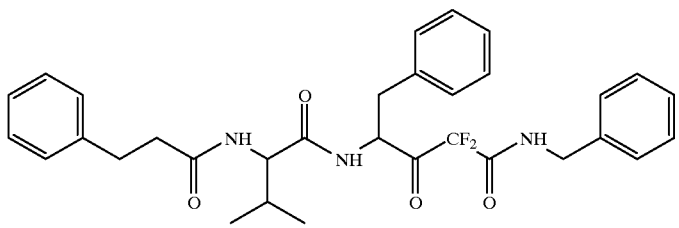

Preparation of 4-(N-Phenylpropionyl-L-valyl)amino-2,2-difluoro-3-oxo-5-phenyl-N-benzylpentanamide Step A: N-Benzyloxylcarbonyl-phenylalaninal The aldehyde CBz(L)-Phe-H (4.19 g) is obtained by reduction of CBz(L)-Phe-OH (15.00 g, 50 mmol) following the procedure described in Example 6 (step A and B).

Step B: 4-Benzyloxycarbonyl amino-2,2-difluoro-3-hydroxy-5-phenylpentanoic acid, ethyl ester Add CBz-(L)-Phe-H (4.19 g, 14.8 mmol) and ethylbromo-difluoroacetate (6.30 g, 31 mmol) in dry THF (40 mL) to a refluxing suspension of activated zinc wool (2.0 g, 31 mAtg) in dry THF (10 mL) to maintain a gentle reflux of the mixture. Stir the solution 12 hours at room temperature. Add to the mixture ethyl acetate (100 mL), brine (20 mL), potassium hydrogenosulfate (20 mL). Extract the aqueous phase with ethyl acetate (3×60 mL), dry over magnesium sulfate and concentrate under vacuum. Purify the crude residue by flash chromatography (silica gel, 3:7 ethyl acetate:cyclohexane) to provide the title compound (3.70 g).

Step C: 4-Benzyloxycarbonylamino-2,2-difluoro-3-hydroxy-5-phenyl-N-benzylpentanamide Add a solution of benzylamine (1.93 g, 18 mmol) in THF (10 mL) to a solution of the ethyl ester (1.42 g, 3.5 mmol) in THF (10 mL). Stir 12 hours. Add ethyl acetate (100 mL), wash with a 0.1 N aqueous hydrochloric acid (2×100 mL) and with water (100 mL) and brine (100 mL). Dry over anhydrous magnesium sulfate. Purification of the crude material by flash chromatography (silica gel, 2:8 ethyl acetate:cyclohexane) provides the title compound (1.16 g).

Step D: 4-Amino-2,2-difluoro-3-hydroxy-5-phenyl-N-benzyl pentanamide

Add the above prepared amide (0.81 g, 1.70 mmol) to a suspension of 10% palladium on carbon (0.28 g) in absolute ethanol (75 mL). Stir for 12 hours, under atmospheric pressure of hydrogen. Filtrate the catalyst, wash with ethanol and concentrate under vacuum to provide the title deprotected amine (0.5 g).

Step E: 4-(N-Phenylpropionyl-L-valyl)amino-2,2-difluoro-3-hydroxy-5-phenyl-N-benzylpentanamide Add N,N'-dicyclohexylcarbodiimide (0.165 g, 0.80 mmol) to a solution of hydrocinnamoyl-Val-OH (3-phenylpropionyl-Val-OH) (0.199 g, 0.80 mmol) in anhydrous acetonitrile (15 mL). Stir at 0° C. for 1 hour. Add the above prepared amine (0.210 g, 0.80 mmol) to the reaction and stir at 25° C. for 12 hours. Filter the mixture, wash with ethyl acetate and concentrate the filtrate under vacuum to provide the crude amide as an oil. Purify the crude residue by flash chromatography (silica gel, 2:8 ethyl acetate:cyclohexane) to provide the title compound (0.16 g).

Step F: 4-(N-Phenylpropionyl-L-valyl)amino-2,2-difluoro-3-oxo-5-phenyl-N-benzylpentanamide Add the above prepared alcohol (0.145 g, 0.25 mmol) in methylene chloride (10 mL) and tert-butyl alcohol (0.055 g, 0.75 mmol) to a suspension of Dess-Martin reagent (0.318 g, 0.75 mmol) in methylene chloride. Stir 12 hours at room temperature and concentrate the mixture under vacuum. Purify the crude residue by flash chromatography (silica gel, 3:7 ethyl acetate:cyclohexane) to provide the title compound (0.063 g).

Anal. Calcd for $C_{32}H_{35}N_3O_4F_2$: C, 68.19; H, 6.26; N, 7.45 Found: C, 67.90; H, 6.30; N, 7.33.

EXAMPLE 8

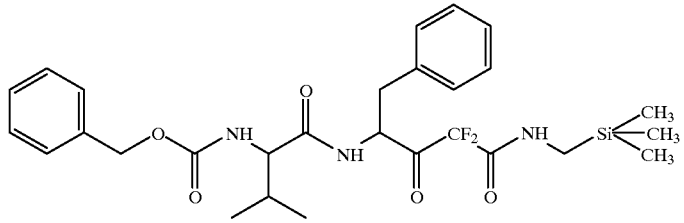

Preparation of 4-(N-Benzyloxycarbonyl-L-valyl)amino-2,2-difluoro-3-oxo-4-phenyl-N-(trimethylsilylmethyl)pentanamide Prepare the 4-benzyloxycarbonylamino-2,2-difluoro-3-hydroxy-5-phenylpentanoic acid, ethyl ester as described in Example 7, Step B.

Step A: 4-Benzyloxycarbonylamino-2,2-difluoro-3-hydroxy-5-phenyl-N-trimethylsilylmethylpentanamide Add the above prepared difluoro alcohol (0.25 g, 0.61 mmol) to trimethylsilylmethylamine (0.81 mL, 6.10 mmol) in THF (2.5 mL). Stir and heat under reflux for 12 hours. Concentrate under vacuum. Dilute with an aqueous solution of potassium hydrogenosulphate (5 mL) and extract with diethyl ether (3×5 mL). Wash the organic phase with water (2×15 mL). Dry over sodium sulphate. Purify the crude residue by flash chromatography (silica gel, 25:75 ethyl acetate:cyclohexane) to provide the title compound (0.212 g).

Step B; 4-Amino-2,2-difluoro-3-hydroxy-5-phenyl-N-(trimethylsilylmethyl)pentanamide Add the above prepared amide (0.10 g, 0.22 mmol) to a suspension of 10% palladium on carbon (0.10 g) in absolute ethanol (10 mL). Stir for 12 hours under atmospheric pressure of hydrogen. Filter the catalyst, wash with ethanol and concentrate under vacuum to provide the title deprotected amine (0.71 g).

Step C: 4-(N-Benzyloxycarbonyl-L-valyl)amino-2,2-difluoro-3-hydroxy-5-phenyl-N-(trimethylsilylmethyl)pentanamide Add N,N'-dicyclohexylcarbodiimide (0.045 g, 0.22 mmol) to a solution of CBz(L)-Val-OH (0.055 g, 0.22 mmol) and hydroxybenzotriazole (0.03 g, 0.22 mmol) in dimethylformamide (10 mL). Stir at 0° C. for 30 minutes. Add the above prepared amine (0.073 g, 0.22 mmol) to the reaction and stir at 25° C. for 12 hours. Add water and brine. Extract with ethyl acetate, wash with water, dry over sodium sulphate and concentrate. Dilute with acetonitrile (5 mL) and precipitate DCU. Filter and concentrate the filtrate under vacuum to provide the crude amide. Purify the crude residue by flash chromatography (silica gel, 35:65 ethyl acetate:petroleum ether) to provide the title compound (0.40 g).

Step D: 4-(N-Benzyloxycarbonyl-L-valyl)amino-2,2-difluoro-3-oxo-5-phenyl-N-(trimethylsilylmethyl)pentanamide Add dimethylsulfoxide (0.031 g, 0.44 mmol) in anhydrous methylene chloride (1 mL) to a solution of oxalyl chloride (0.02 mL, 0.22 mmol) in methylene chloride (1 mL) at −60° C. Stir for 5 minutes at −60° C. and add the above prepared alcohol (0.041 g, 0.07 mmol) in methylene chloride (2 mL). Stir the reaction 1 hour at this temperature. Add the triethylamine (0.09 mL, 0.65 mmol) and allow the reaction to warm to room temperature. Stir the mixture an additional few minutes. Dilute with methylene chloride (10 mL). Wash the organic phase with potassium hydrogenosulphate (3×10 mL, 1N) and water (2×10 mL). Dry the organic phase over sodium sulfate, filter and concentrate under vacuum to provide the crude compound. Purify the crude residue by flash chromatography (ethylacetate:petroleum ether 25:75, $R_f$: 0.2) to provide the title compound (0.015 g).

Anal. Calcd for $C_{31}H_{33}N_3O_5F_2$, 0.25 $H_2O$: C, 58.93; H, 6.71; N, 7.36 Found: C, 58.74; H, 6.72; N, 7.16

EXAMPLE 9

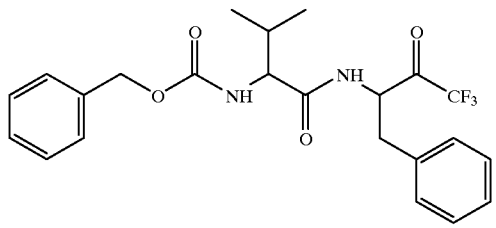

Preparation of 3-(benzyloxYcarbonyl-L-valyl)amino-1,1,1,-trifluoro-2-oxo-4-phenylbutane Prepare the 3-[benzyloxycarbonyl-L-valyl]amino-1,1,1,-trifluoro-2-hydroxy-4-phenylbutane from CBz(L)-Val-OH (0.128 g, 0.5 mmol) and 1,1,1-trifluoro-3-amino-4-phenyl-2-butanol (0.112 g, 0.5 mmol, J. Med. Chem. 1990, 33, 394–407) by the coupling reaction described in Example 6.

Oxidize the above prepared alcohol (0.71 g, 0.16 mmol) using oxalyl chloride as described in Example 8 to provide the title compound (0.60 g).

Anal. Calcd for $C_{23}H_{25}F_2N_2O_4F_2$, 0.5 $H_2O$: C, 60.12; H, 5.70; N, 6.10 Found: C, 60.08; H, 5.81; N, 5.89.

EXAMPLE 10

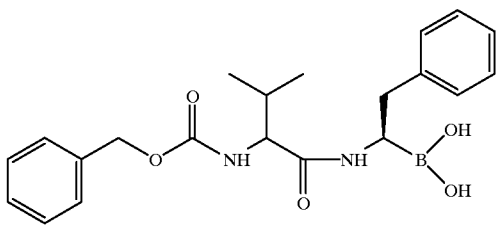

Preparation of 1-N-Benzyloxycarbonylvalylamino-2-phenyl-ethane boronic acid

Desilylate (+)pinanediol-1-N,N-bis(trimethylsilyl)amino-2-phenylethaneboronate (J. Am. Chem. Soc. (1981) 103, 5241) with methanol at 0° C. Concentrate under vacuum and wash with diethyl ether to provide the crude deprotected aminoboronate.

Add N-carbobenzoxyvaline anhydride to the solution of the crude deprotected aminoboronate prepared above in anhydrous THF to yield the coupled compound.

Cleave the pinanediol of the coupled compound prepared above using boron trichloride as described in the procedure J. Am. Chem. Soc. (1980), 102, 7590.

Purify the title compound by ion exchange column or by the procedure described in Biochemistry (1987), 26, 7609 and references herein.

EXAMPLE 11

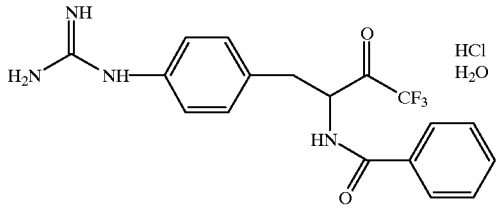

Peparation of N-[2-[4-(Aminoiminomethyl)amino)phenyl]-1-trifluoroacetvlethyl]benzamide, hydrochloride hydrate The synthesis for this compound is described in Liebigs Ann. Chem. 1990, 1–6 which is incorporated herein by reference.

EXAMPLE 12

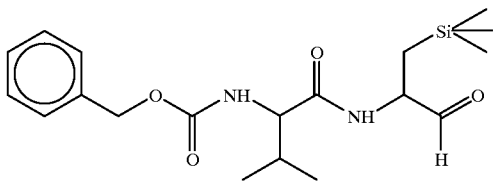

Preparation of 2-(N-Benzyloxycarbonyl-L-valyl)amino-3-trimethylsilylpropanal

Step A: 2-Benzyloxycarbonylamino-3-trimethylsilyl-propanoic acid, methyl ester

A solution of 5.58 g (25 mmol) of N-benzyloxycarbonyl glycine methyl ester in dry THF (70 ml) is added dropwise to a solution at −78° C. of lithium diisopropylamine (8.76 ml, 62.5 mmol) and tetramethylethylene diamine (9.43 ml, 62.5 mmol) in dry THF (100 ml), under nitrogen. After the addition is complete, the solution is stirred for 2 hours at −78° C., then 15 minutes at −30° C. and cooled to −78° C. A solution of 5.36 g (25 mmol) of iodomethyl-trimethylsilane in dry hexamethylphosphoramide (39 ml) is added dropwise to the resultant syrupy mixture. After the addition is complete, the reaction mixture is warmed up to −50° C., kept at this temperature for 1 hour and cooled to −78° C., just before hydrolysis. The reaction mixture is quenched by addition of water and ammonium chloride and diluted with ether. The organic layer is washed with 1N potassium hydrogen sulfate, twice with water and dried over sodium sulfate. The solvent is evaporated and the residue obtained (8.03 g) is purified by flash chromatography (silica gel,ethyl acetate/petroleum ether: 2/8). 4.30 g of the title compound are obtained (yield: 56%) (colorless oil). $R_f$: 0.51 (ethyl acetate/petroleum ether: 2/8).

Step B: 2-Amino-3-trimethylsilylpropanoic acid, methyl ester, hydrochloride

A solution of the derivative of Example 12, Step A (0.309 g, 1 mmol) in ethanol (30 ml) and in dry diethylether saturated in hydrogen chloride (1.5 ml) is stirred at room temperature for 24 hours under an atmosphere of hydrogen in the presence of 10% Palladium on charcoal (0.03 g). The hydrogen atmosphere is changed to a nitrogen atmosphere and the catalyst filtered off. After concentration under vacuo, the title compound obtained as a solid is used as such in the next step.

Step C: 2-(N-Benzyloxycarbonyl-L-valyl)amino-3-trimethyl-silylpropanoic acid, methyl ester To a stirred solution of N-benzyloxy-carbonyl-L-valine (0.311 g, 1.24 mmol), 1-hydroxybenzotriazole, hydrate (0.167 g, 1.24 mmol) and N,N'-dicyclohexylcarbodiimide (0.255 g, 1.24 mmol) in methylene chloride (20 ml) and dimethylformamide (3 ml), at 0° C. are successively added the amine of Example 12, Step B (0.262 g, 1.24 mmol) and N-methylmorpholine (0.136 ml, 1.24 mmol). The cooling bath is removed and the reaction mixture is stirred at room temperature for 17 hours. The reaction mixture is then filtered off and the filtrate wis concentrated under vacuo. The residue (0.476 g) is purified by flash chromatography (silica gel, petroleum ether/ethyl acetate: 8/2; $R_f$: 0.14) to give the title compound (0.316 g, 77% yield for two steps).

Step D: 2-(N-Benzyloxycarbonyl-L-valyl)amino-3-trimethyl-silylpropanal

A solution of 1M diisobutylaluminum hydride in hexane (1.55 ml) is added dropwise to a solution of the ester of Example 12, Step C, at −78° C. (0.316 g, 0.77 mmol) in anhydrous ether (7.5 ml) and anhydrous toluene (3.5 ml), under nitrogen. The solution is stirred at −78° C. for 45 minutes and hydrolyzed slowly with a saturated solution of ammonium chloride in water. The aqueous phase is extracted twice with ether (2×20 ml) and the organic phases washed successively with iN potassium hydrogen sulfate (10 ml) and water (20 ml). The combined organic layers are dried over sodium sulfate, filtered off and removal of the solvent under vacuo affords a solid residue (0.260 g) which is purified by flash chromatography (silica gel, petroleum ether/ethyl acetate: 75/25, $R_f$: 0.25) to give the title compound in 53% yield (0.15 g). Crystallization from dichloromethane/pentane gives 0.077 g of a white cottony solid.

Analysis calcd for $C_{19}H_{30}N_2O_4Si$: C, 60.29; H, 7.99; N, 7.40. Found: C, 60.23; H, 8.10; N, 7.42.

EXAMPLE 13

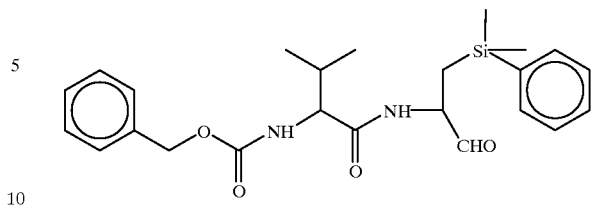

Preparation of 2-(N-Benzyloxycarbonyl-L-valyl)amino-3-phenyldimethylsilyl-propanal Step A: 2-tert-Butoxycarbonylamino-3-phenyldimethylsilyl-propanoic acid, methyl ester The title ester is prepared in 28% yield from N-tert-butoxycarbonyl glycine methyl ester and iodomethyl-phenyldimethylsilane (prepared in 81% yield from commercially available chloromethyl-phenyldimethylsilane) following the procedure described in Example 12, Step A. $R_f$: 0.23 (silica gel, ethyl acetate/petroleum ether: 1/9).

Step B: 2-Amino-3-phenyldimethylsilane-propanoic acid, methyl ester

A solution of the derivative of Example 13, Step A (0.92 g, 2.73 mmol) in formic acid (30 ml) is kept for 2 hours at room temperature. After removal of formic acid in vacuo, the residue is dissolved in ethyl acetate (20 ml), extracted with 1M sodium carbonate (20 ml) and washed twice with water, the aqueous phases being extracted once more with ethyl acetate (20 ml). After drying of the combined organic layers over sodium sulfate, the solvent is evaporated and the title compound is obtained in 98% yield (0.64 g).

Step C: 2-(N-Benzyloxycarbonyl-L-valyl)amino-3-phenyl-dimethylsilyl-propanoic acid, methyl ester The title compound is obtained from the amine of Example 13, Step B and N-benzyloxycarbonyl-L-valine using the coupling method given in Example 12, Step C but with 1-ethyl -3(3-dimethylaminopropyl)carbodiimide, hydrochloride instead of N,N'-dicyclohexylcarbodiimide (74% yield). $R_f$: 0.19 (silica gel, ethyl acetate/petroleum ether: 2/8).

Step D: 2-(N-Benzyloxycarbonyl-L-valyl)amino-3-phenyldimethylsilyl-propanal

The title aldehyde is prepared in 33% yield from the ester of Example 13, Step C following the reduction procedure described in Example 12, Step D. $R_f$: 0.17 (silica gel, ethyl acetate/petroleum ether: 2/8).

Anal. Calcd for $C_{24}H_{32}N_2O_4Si$: C, 65.42; H, 7.32; N, 6.36 Found: C, 65.33; H, 7.10; N, 6.26.

EXAMPLE 14

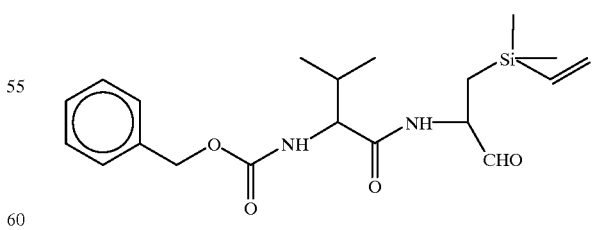

Preparation of 2-(N-Benzyloxycarbonyl-L-valyl)amino-3-vinyldimethylsilyl-propanal Step A; 2-tert-Butoxycarbonylamino-3-vinyldimethylsilyl-propanoic acid, methyl ester The title ester is prepared in 51% yield from N-tert-butoxycarbonyl glycine, methyl ester and iodomethylvinyldimethylsilane following the procedure given in Example 12, Step A.

$R_f$: 0.35 (silica gel, ethyl acetate/petroleum ether: 1/9).

Step B: 2-Amino-3-vinyldimethylsilyl-propanoic acid, methyl ester

The title amine is obtained from the derivative of Example 14, Step A following the deprotection method given in Example 13, Step B (quantitative yield).

Step C: 2-(N-Benzyloxycarbonyl-L-valyl)amino-3-vinyldimethylsilyl propanoic acid, methyl ester The title compound is prepared in 68% yield from the amine of Example 14, Step B and N-benzyloxycarbonyl-L-valine using the coupling method described in Example 13, Step C.

$R_f$=0.22 (silica gel, ethyl acetate: petroleum ether 2:8)
MS: MH$^+$=421, MNH$_4^+$=438

Step D: 3-(N-Benzyloxycarbonyl-L-valyl)amino-3-vinyl-dimethylsilyl-propanal

The title aldehyde is obtained from the ester of Example 14, Step C following the reduction procedure given in Example 12, Step D.

EXAMPLE 15

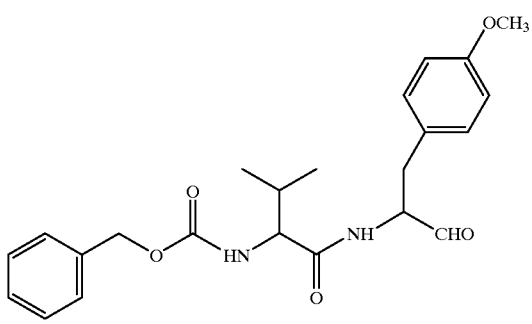

Preparation of N-Benzyloxycarbonyl-L-valyl-(O-methyl)-L-tyrosinal

Step A: N-Benzyloxycarbonyl-L-valyl-O-methyl-L-tyrosine benzyl ester

To a solution of N-benzyloxycarbonyl-L-valine anhydride (0.339 g, 0.7 mmol) in anhydrous dichloromethane (15 ml) are added O-methyl-L-tyrosine, benzyl ester, toluene-4-sulfonate (0.330 g, 0.7 mmol) and N-methyl morpholine (0.081 g, 0.8 mmol). The reaction is stirred at room temperature overnight. The solvent is removed invacuo and the residue is purified by flash chromatography (silica gel: 2:8 ethyl acetate/cyclohexane) to give the title compound as a white solid.

Step B: N-Benzyloxycarbonyl-L-valyl-(O-methyl)-L-tyrosinal

To a solution of N-benzyloxycarbonyl-L-valyl-o-methyl-L-tyrosine benzyl ester (0.250 g, 0.48 mmol) in anhydrous toluene (5 ml) and diethyl ether (5 ml) at −78° C., is added a 1.2 M solution of diisobutyl aluminum hydride in hexane. (1.6 ml, 2 mmol). The reaction is stirred at −78° C. for one hour then hydrolized with a saturated solution of potassium sodium tartrate (5 ml). The temperature is then allowed to rise to room temperature.

The mixture is acidified with a 1M solution of potassium hydrogenosulfate until pH~3 and extracted three times with ethyl acetate (3×20 ml). The organic layer is dried over anhydrous magnesium sulfate. Filtration and removal of the solvent invacuo affords a residue which is purified by flash chromatography (silica gel: 3:7 ethyl acetate/cyclohexane) to give the title compound as a white solid.

EXAMPLE 16

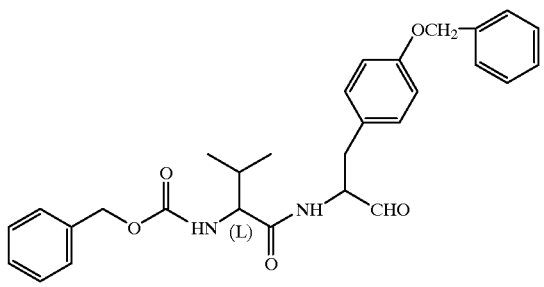

Preparation of N-Benzyloxycarbonyl-L-valyl-O-benzyl-L-tyrosinal

Step A: N-tert-Butoxycarbonyl-O-Benzyl-L-tyrosine,N,O-dimethyl hydroxamate

To a solution of tert-butoxycarbonyl amino-O-(L)benzyl tyrosine (23 g, 61.9 mmol), in anhydrous methylene chloride (250 ml) at 0° C. are added N,N-dicyclohexylcarbodiimide (12.75 g, 61.9 mmol) and hydroxybenzotriazole (9.47 g, 61.9 mmol). The mixture is stirred at 0° C. for 10 minutes, and N,O-dimethylhydroxylamine, HCl (6.04 g, 61.9 mmol) and N-methylmorpholine (6.25 g, 61.9 mmol) are then added. The reaction is stirred at room temperature for 12 hours. The mixture is then filtered and the filtrate concentrated. The crude mixture is purified by flash chromatography (silica gel: 2:8 ethyl acetate:cyclohexane) to provide the title compound as a white solid (22.60 g, 88% yield). $R_f$=0.36 (ethyl acetate/cyclohexane).

Step B: O-Benzyl-L-tyrosine,N,O-dimethyl hydroxamate

A solution of N-tert-butoxycarbonyl-O-benzyl (L) tyrosine, N,O-dimethyl hydroxamate (8.28 g, 20 mmol) in trifluoroacetic acid (100 ml) is stirred at 0° C. for 1 hour. The solvent is removed in vacuo. The residue is taken off in diethyl ether (250 ml) and washed three times with a saturated solution of sodium carbonate (3×50 ml). The organic layer is dried over anhydrous magnesium sulphate. Filtration and removal of the solvent in vacuo yields the title compound as a pale yellow oil (6.00 g, 90% yield) which is used without purification in the next step.

Step C: N-Benzyloxycarbonyl-L-valyl-O-benzyl-L-tyrosine,N,O-dimethyl hydroxamate To a solution of Z-L valine anhydride (8.47 g, 17.5 mmol) in anhydrous methylene chloride (150 ml) is added O-benzyl-L-tyrosine,N,O-dimethylhydroxamate (5.50 g, 17.5 mmol). The mixture is stirred at room temperature overnight. The solvent is removed in vacuo and the crude mixture is purified by flash chromatography (silica gel: 2:7 ethyl acetate/cyclohexane) to provide the title compound as a white solid (8.90 g, 93% yield). $R_f$=0.18 (1:1 ethylacetate/cyclohexane).

Step D: N-Benzyloxycarbonyl-L-valyl-O-benzyl-L-tyrosinal

To a solution of N-benzyloxycarbonyl-L-valyl-O-benzyl-L-tyrosine, N,O-dimethylhydroxamate (8.90 g, 16.2 mmol) in anhydrous diethyl ether (150 ml) and anhydrous THF (20 ml) at 0° C. is added lithium aluminum hydride (0.67 g, 17.7 mmol). The mixture is stirred at 0° C. for 1 hour. A solution of 1M potassium hydrogenosulphate (25 ml) is then added with precaution. The organic layer is separated and the aqueous phase is extracted twice with ethyl acetate (2×100 ml). The combined organic layers are then washed with a 3N solution of hydrochloric acid (30 ml), water (30 ml) and brine (30 ml), and dried over anhydrous magnesium sulphate. Filtration and evaporation of the solvent in vacuo affords a white solid which is recrystallized in ethylacetate/pentane to give the title compound (5.40 g, 68% yield).

$R_f \cong 0.33$ (ethyl acetate/cyclohexane) m.p.: 160–162° C.

Analysis calculated for $C_{29}H_{32}N_2O_5$: Calc. C, 71.29; H, 6.60; N, 5.73. Found: C, 71.18; H, 6.94; N, 6.30.

anhydrous THF (20 ml) at 0° C. is added lithium aluminum hydride (0.121 g, 3.2 mmol). The mixture is stirred at 0° C. for 1 hour. A solution of 1M aqueous potassium hydrogenosulphate sulphate (25 ml) is added. The mixture is extracted three times with ethyl acetate (3×50 ml). The combined organic layer is washed with 3N hydrochloric acid, water and brine, then dried over anhydrous magnesium sulphate. Filtration and evaporation of the solvent invacuo afforded a white solid which is purified by recrystallization (Ethyl acetate/pentane) to give the title compound (0.96 g, 67% yield).

$R_f \cong 0.34$ (ethyl acetate/cyclohexane 1:1) MS: $[MH]^+ = 515$ $[MNH_4]^{30} = 532$ Analysis calculated for $C_{31}H_{34}N_2O_5$: Calc.: C, 72.35; H, 6.66; N, 5.44. Found: C, 72.38; H, 6.64; N, 5.52.

EXAMPLE 18

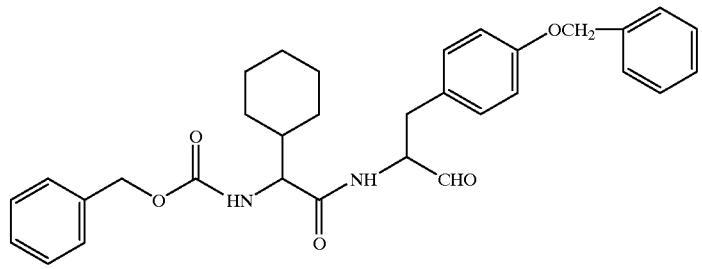

EXAMPLE 17

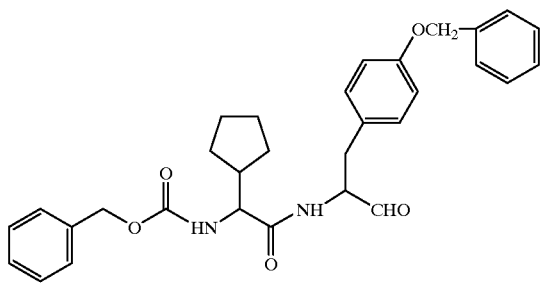

Preparation of N-Benzyloxycarbonyl-2-cyclopentylglycine-O-benzyl-L-tyrosinal

Step A: N-Benzyloxycarbonyl-2-cyclopentylglycine-O-benzyl-L-tyrosine,N,O-dimethyl hydroxamate To a solution of racemic N-benzyloxycarbonyl-2-cyclopentylglycine (0.831 g, 3 mmol) in anhydrous acetonitrile (20 ml) is added N-methylmorpholine (0.323 g, 3.2 mmol). The mixture is cooled to −20° C. under nitrogen and isobutyl-chlorformate 0.410 g, 3 mmol) is added. After 10 minutes stirring at −20° C., O-benzyl-L-tyrosine,N,O-dimethyl hydroxamate (1.00 g, 3.1 mmol) in anhydrous acetonitrile (10 ml) is added. The mixture is stirred at −20° C. under nitrogen for 4 hours and then the temperature is allowed to rise to room temperature overnight. The crude mixture is evaporated and the residue is purified by flash chromatography (silica gel: 3:7 ethyl acetate/cyclohexane) to provide the title compound as a white solid (1.60 g, 93% yield). $R_f \cong 0.26$ (ethyl acetate/cyclohexane 1:1).

Step B: N-Benzyloxycarbonyl-2-cyclopentylglycine-O-benzyl-L-tyrosinal

To a solution of N-benzyloxycarbonyl-2-cyclopentylglycine-O-benzyl-L-tyrosine,N,O-dimethyl hydroxamate (1.60 g, 2.8 mmol) in anhydrous diethyl ether (20 ml) and Preparation of N-Benzyloxycarbonyl-2-cyclohexylglycine-O-benzyl-L-tyrosinal Step A: N-Benzyloxycarbonyl-2-cyclohexylglycine-O-benzyl-L-tyrosine,N,O-dimethyl hydroxamate To a solution of racemic N-benzyloxycarbonyl-2-cyclohexylglycine (0.873 g, 3 mmol) in anhydrous acetonitrile (25 ml) is added N-methylmorpholine (0.323 g, 3.2 mmol). The mixture is cooled to −20° C. and isobutylchloroformate (0.410 g, 3 mmol) is added. After 10 minutes stirring at −20° C. under nitrogen, O-benzyl-L-tyrosine,N,O-dimethyl hydroxamate (1.00 g, 3.1 mmol) in anhydrous acetonitrile (10 ml) is added. The mixture is stirred at −20° C. under nitrogen for 4 hours and then the temperature is allowed to rise to room temperature overnight. The solvent is removed inuacuo and the residue is purified by flash chromatography (silica gel: 3:7 ethyl acetate/cyclohexane) to provide the title compound as a white solid (1.00 g, 57% yield). $R_f \cong 0.35$ (ethyl acetate/cyclohexane).

Step B: N-Benzyloxycarbonyl-2-cyclohexylglycine-O-benzyl-L-tyrosinal

To a solution of N-benzyloxycarbonyl-2-cyclohexylglycine-O-benzyl-L-tyrosine,N,O-dimethyl hydroxamate (0.96 g, 1.6 mmol) in anhydrous diethyl ether (20 ml) and anhydrous THF (20 ml) at 0° C. is added lithium aluminum hydride (0.068 g, 1.8 mmol). The mixture is stirred at 0° C. for 1 hour. An aqueous solution of 1M aqueous potassium hydrogenosulphate (25 ml) is added. The mixture is extracted three times with ethyl acetate (3×50 ml). The combined organic layer is washed with 3N hydrochloric acid, water and brine, then dried over anhydrous magnesium sulphate.

Filtration and evaporation of the solvent invacuo affords a white solid which is purified by recrystallization (AcOEt/pentane) to give the title compound (0.56 g, 67% yield).

MS: $[EMH]^+ = 529$ $[MNH_4]^+ = 546$ Analysis calculated for $C_{32}H_{36}N_2O_5$: Calc: C, 72.71; H, 6.86; N, 5.30. Found: C, 72.43; H, 6.92; N, 5.43.

EXAMPLE 19

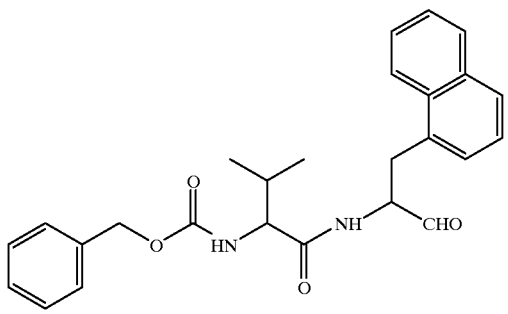

Preparation of N-Benzyloxycarbonyl-L-valyl-3-(1-naphthyl)-L-alaninal

Step A: N-tert-Butoxycarbonyl-[3-(1-naphthyl)-L-alanine]-N,O-dimethyl hydroxamate To a solution of N-tert-butoxycarbonyl-[3-(1-naphthyl)-L-alanine] (0.65 g, 2 mmol) in anhydrous dichloromethane (20 ml) at 0° C. are added N,N-dicyclohexyl carbodiimide (0.412 g, 2 mmol) and hydroxybenzotriazole (0.306 g, 2 mmol). After 10 minutes stirring, N,O-dimethylhydroxyl- amine, chlorohydrate (0.195 g, 2 mmol) and N-methylmorpholine (0.202 g, 2 mmol) are added. The reaction is stirred at room temperature for 12 hours. The mixture is filtered and the filtrate concentrated. The crude residue is purified by flash chromatography (silica gel: 4:6 ethyl acetate/cyclohexane). The title compound is obtained as a colorless oil (0.56 g, 78% yield). $R_f$=0.36 (ethyl acetate/cyclohexane 1:1).

Step B: 3-(1-Naphthyl)-L-alanine-N,O-dimethyl hydroxamate

A solution of N-tert-butoxycarbonyl-[3-(1-naphthyl)-L-alanine]-N,O-dimethyl hydroxamate (0.560 g, 1.5 mmol) in formic acid (20 ml) is stirred at room temperature for 4 hours. The solvent is removed invacuo. The residue is taken off in ethyl acetate (50 ml) and washed three times with a saturated solution of sodium carbonate (3×10 ml) and dried over anhydrous magnesium sulphate. Filtration and evaporation of the solvent invacuo affords a colorless oil which is used without purification in the next step (0.330 g, 85% yield).

Step C: N-Benzyloxycarbonyl-L-valyl-3-(1-naphthyl)-L-alanine-N,O-dimethyl hydroxamate To a solution of Z-L-valine anhydride (0.581 g, 1.2 mmol) in anhydrous dichloromethane (10 ml) is added 3-(1-naphthyl)-L-alanine-N,O-dimethyl hydroxamate (0.320 g, 1.2 mmol). The mixture is stirred at room temperature overnight. The solvent is removed invacuo and the residue is purified by flash chromatography (silica gel: 3:7 ethyl acetate/cyclohexane). The title compound is obtained as a white solid (0.470 g, 80% yield). $R_f$=0.23 (ethyl acetate/cyclohexane).

Step D: N-Benzyloxycarbonyl-L-valyl-3-(1-naphthyl)-L-alaninal

To a solution of N-benzyloxycarbonyl-L-valyl-3-(1-naphthl) -L-alanine-N,O-dimethyl hydroxamate (0.470 g, 0.96 mmol) in anhydrous diethyl ether (10 ml) and anhydrous THF (10 ml) at 0° C. is added lithium aluminum hydride (0.042 g, 1.1 mmol). The reaction is stirred at 0° C. for 1 hour. A solution of 1M potassium hydrogenosuphate (5 ml) is then added. The mixture is extracted three times with ethyl acetate (3×30 ml). The organic layer is washed with 1N hydrochloric acid, water and brine, and dried over anhydrous magnesium sulphate. Filtration and evaporation of the solvent invacuo affords a white solid which is purified by recrystallization in ethylacetate/pentane to give the title compound (0.260 g, 63% yield). $R_f$=0.36 (Ethyl acetate/cyclohexane 1:1) MS: $[MH]^+$=433 $[MNH_4]^+$=450 Analysis calculated for $C_{26}H_{28}N_2O_4$: Calc: C, 72.20; H, 6.52; N, 6.48. Found: C, 71.87; H, 6.50; N, 6.48.

EXAMPLE 20

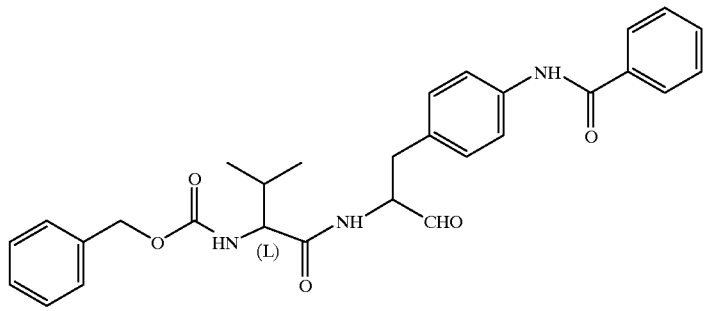

Preparation of N-Benzyloxycarbonyl-L-valyl-4-(phenylcarbonylamino)-L-phenylalaninal Step A: N-Benzyloxycarbonyl-L-valyl-4-nitro-L-phenylalanine methyl ester To a solution of Z-L-valine anhydride (4.80 g, 10 mmol) in anhydrous dichloromethane (50 ml) is added 4-nitro-L-phenylalanine methyl ester (2.24 g, 10 mmol). The mixture is stirred at room temperature overnight. The solvent is removed invacuo and the residue is purified by flash chromatography (silica gel: 4:6 ethyl acetate/cyclohexane) to give the title compound (2.10 g, 56% yield). $R_f$=0.32 (ethyl acetate/cyclohexane 1:1).

Step B: N-Benzyloxycarbonyl-L-valyl-4-(phenylcarbonylamino)-L-phenylalanine methyl ester A solution of N-benzyloxycarbonyl-L-valyl-4-nitro-L-phenylanine phenylalanine methyl ester (0.91 g, 2 mmol) and Tin (II) chloride dihydrate (1.56 g, 7 mmol) in absolute ethanol (50 ml) and N,N-dimethylformamide (5 ml) is heated under reflux for 4 hours. The mixture is cooled and diluted with water, neutralized with sodium hydrogenocarbonate, extracted three times with ethyl acetate (3×50 ml). The organic layer is dried over magnesium sulphate. After filtration and evaporation of the solvent, the residue is taken up in anhydrous dichloromethane (20 ml) and cooled to 0° C. Triethylamine (0.202 g, 2 mmol), followed by benzoyl chloride (0.281 g, 2 mmol) are added. The mixture is stirred at room temperature overnight. The solvent is removed inuacuo and the residue purified by flash chromatography (silica gel: 98;2 dichloromethane/ methanol) to give the title compound (0.500 g, 50% yield).
Step C: N-Benzyloxycarbonyl-L-valyl-4-(phenylcarbonyl-amino)-L-phenylalanine To a solution of N-benzyloxycarbonyl-L-valyl-4-(phenylcarbonylamino)-L-phenylalanine methyl ester (0.500 g, 0.94 mmol) in dioxane (30 ml) is added lithium hydroxide monohydrate (0.084 g, 2 mmol) in water (10 ml). The reaction is stirred at room temperature overnight. The mixture is taken off in water (20 ml) and washed twice with ethyl acetate (2×20 ml). The aqueous phase is acidified until pH ~2 with 1N hydrochloric acid and extracted three times with ethyl acetate (3×20 ml). The organic layer is dried over anhydrous magnesium sulphate. After filtration and remtial of the solvent invacuo the title compound is obtained as a white solid (0.400 g, 82% yield). MS: [MH]$^+$=518 [MNH$_4$]$^+$=535.

Step D: N-Benzyloxycarbonyl-L-valyl-4-(phenylcarbonyl-amino)-L-phenylalanine-N,O-dimethyl hydroxamate To a solution of N-benzyloxycarbonyl-L-valyl-4-(phenylcarbonylamino)-L-phenylalanine (0.390 g, 0.75 mmol) in anhydrous N,N-dimethylformamide (5 ml) and anhydrous dichloromethane (15 ml) at 0° C., are added N,N-dicyclohexyl-carbodiimide (0.155 g, 0.75 mmol) and hydroxybenzotriazole (0.115 g, 0.75 mmol). After 10 minutes stirring N,O-dimethyl hydroxamate chlorohydrate (0.073 g, 0.75 mmol) and N-methylmorpholine (0.076 g, 0.75 mmol) are added. The reaction is stirred at room temperature overnight, the solvent removed in vacuo, and the residue is taken up in ethyl acetate and filtered. The filtrate is concentrated and the residue is purified by flash chromatography (silica gel: 98:2 dichloromethane/ methanol) to give the title compound (0.230 g, 53% yield).

R$_f$≅0.59 (CH$_2$Cl$_2$/MeOH 9:1) MS: [MH]$^+$=561 [MNH$_4$]$^+$=578.

Step E: N-Benzyloxycarbonyl-L-valyl-4-(phenylcarbonyl-amino)-L-phenylalaninal

To a solution of N-benzyloxycarbonyl-L-valyl-4-(phenylcarbonylamino)-L-phenylalanine-N,O-dimethyl hydroxamate (0.230 g, 0.41 mmol) in anhydrous diethyl ether (10 ml) and anhydrous THF (5 ml) at 0° C., is added lithium aluminum hydride (0.017 g, 0.45 mmol). The reaction is stirred at 0° C. for 1 hour. A 1M solution of potassium hydrogenosulphate (5 ml) is added and the mixture is extracted three times with ethyl acetate (3×15 ml). The organic layer is washed with 1N hydrochloric acid, water and brine, and then dried over anhydrous magnesium sulphate. After removal of the solvent invacuo, the residue is purified by flash chromatography (silica gel: 98:2 dichloromethane/methanol) to give the title compound (0.050 g, 25% yield).

R$_f$≅0.43 (CH$_2$Cl$_2$/MeOH 9:1) MS: [MH]$^+$=502 [MNH$_4$]$^+$=519.

EXAMPLE 21

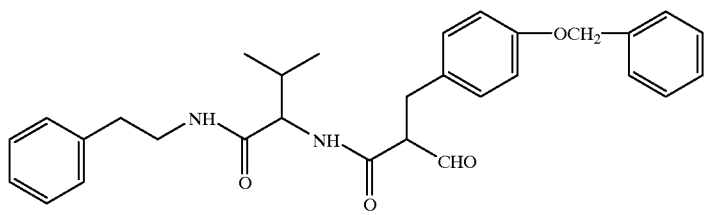

Preparation of 2(D)-[3-(4-Benzyloxy-phenyl)-2-formyl-propionylamino]-3-methyl-N-phenethyl butyramide Step A: 4-Benzyloxybenzyl malonic acid, tert-butyl, ethyl ester To a suspension of 45% sodium hydride (6.40 g, 0.12 mmol) in anhydrous tetrahydrofuran (100 ml) under nitrogen, is added tert-butyl ethyl malonate (20,7 g, 0.11 mmol) in anhydrous tetrahydrofuran (100 ml). The mixture is stirred at room temperature for 2 hours. 4-benzyloxybenzyl bromide (29.60 g, 0.11 mmol) in anhydrous THF (50 ml) is then added. The reaction is stirred at room temperature overnight, hydrolized with water and concentrated. The mixture is extracted three times with diethyl ether (3×200 ml). The residue is purified by flash chromatography (silica gel: 9:1 toluene/ ether) and recrystallized (diethyl ether: pentane) to give the title compound (20.0 g; 47% yield).

R$_f$=0.65 (toluene: ether 9:1).

Step B: 4-Benzyloxybenzyl malonic acid, ethyl ester

A solution of 4-Benzyloxybenzyl malonic acid, tert-butyl-ethyl ester (19.0 g, 49.5 mmol) in trifluoroacetic acid (200 ml) is stirred at 0° C. for one hour. The solvent is removed in vacuo. The residue is recrystallized in diethyl ether/ pentane to give the title compound (8.50 g; 53% yield).

Step C: 2(D)-[3-(4-Benzyloxy-phenyl)-2-carboxy diethylester-propionylamino]-3-methyl-N-phenethyl butyramide To a solution of 4-Benzyloxybenzyl malonic acid, ethyl ester (8.50 g, 25.9 mmol) in anhydrous dichloromethane (150 ml) at 0° C., are added N,N-dicyclohexylcarbodiimide (5.33 g, 25.9 mmol), hydroxybenzotriazole (3.96 g, 25.9 mmol) and (D) valine phenethylamide (5.70 g, 25.9 mmol). The reaction is stirred at room temperature overnight.

The precipitate is filtered and the filtrate is concentrated. The residue is purified by flash chromatography (silica gel: 3:7 ethyl acetate/cyclohexane) to give the title compound (7.0 g; 51% yield) as a white solid.

R$_f$=0.33 (ethyl acetate/cyclohexane 1:1) MS: [MH]$^+$=531 Analysis calculated for C$_{32}$H$_{38}$N$_2$O$_5$: Calc: C, 72.43; H, 7.22; N, 5.28. Found: C, 72.15; H, 7.36; N, 5.39.

Step D: 2(D)-[3-(4-Benzyloxy-phenyl)-2-carboxy-propionylamino]-3-methyl-N-phenethyl butyramide To a solution of 2(D)-[3-(4-Benzyloxy-phenyl)-2-carboxydiethylester-propionylamino]-3-methyl-N-phenethyl butyramide (7.0 g, 13.2 mmol) in 2-methoxy ethanol (100 ml) is added a solution of lithium hydroxide (0.84 g, 20 mmol) in water (50 ml). The reaction is refluxed for 12 hours. The solvent is removed invacuo, the residue taken off in water (100 ml) and washed two times with ethyl acetate (2×30 ml). The aqueous phase is acidified until pH ~2 with 3N hydrochloric acid, saturated with sodium chloride and extracted three times with ethyl acetate (3×50 ml). The organic layer is dried over anhydrous magnesium sulfate.

After filtration and removal of the solvent invacuo, the residue is purified by recrystallization (ethyl acetate/pentane) to give the title compound (4.0 g; 60% yield).

MS: $[MH]^+=503$

Step E: 2(D)-[3-(4-Benzyloxy-phenyl)-2-N,O-dimethyl carboxamate-propionylamino]-3-methyl-N-phenethyl butyramide To a solution of 2(D)-[3-(4-Benzyloxy-phenyl)-2-carboxy-propionylamino]3-3-methyl-N-phenethyl butyramide (4.00 g, 8 mmol) in anhydrous dichloromethane (100 ml) and N,N dimethylformamide (10 ml) at 0° C. are added N,O dimethylhydroxamate, hydrochloride (0.78 g, 8 mmol) N-methylmorpholine (0.81 g, 8 mmol) and N,N dicyclohexylcarbodiimide (1.65 g, 8 mmol). The reaction is stirred at room temperature overnight. The mixture is filtered and the filtrate concentrated invacuo. The residue is purified by flash chromatography (silica gel: 1:1 ethyl acetate/cyclohexane) to give the title compound as a white solid (3.20 g; 74% yield).

$R_f \cong 0.45$ (ethyl acetate) MS: $[MH]^+=546$ $[MNH_4]^+=563$ Analysis calculated for $C_{32}H_{39}N_3O_5$: Calc: C, 70.44; H, 7.20; N, 7.70. Found: C, 70.22; H, 7.02; N, 7.65.

Step F: 2(D)-[3-(4-Benzyloxy-phenyl)-2-formyl-propionylamino]-3-methyl-N-phenethyl butyramide To a solution of 2(D)-[3-(4-Benzyloxy-phenyl)-2-N,O-dimethyl carboxamate-propionylamino]-3-methyl-N-phenethyl butyramide (3.0 g, 5.5 mmol) in anhydrous tetrahydrofuran (50 ml is added lithium aluminum hydride (0.240 g, 6.3 mmol). The reaction is stirred at 0° C. for one hour then hydrolized with a solution 1M of potassium hydrogeno sulfate (20 ml) and extracted three times with ethyl acetate (3×50 ml). The organic layer is washed with 1N hydrochloric acid, water and brine then dried over anhydrous magnesium sulfate. Filtration and removal of the solvent invacuo affords a white solid which is recrystallized in ethyl acetate/pentane to give the title compound (2.30 g; 86% yield).

MS: $[MH]^+=487$ $[MNH_4]^+=504$ Analysis calculated for $C_{30}H_{34}N_2O_4$, $0.5H_2O$: Calc.: C, 72.70; H, 7.12; N, 5.65. Found: C, 72.90; H, 7.03; N, 5.89.

EXAMPLE 22

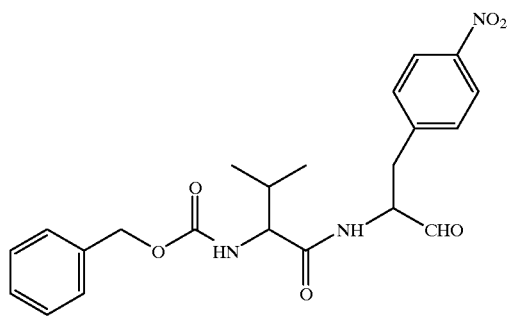

Preparation of N-Benzyloxycarbonyl-L-valyl-4-nitro-L-phenylalaninal

To a solution of N-Benzyloxycarbonyl-L-valyl-4-nitro-L-phenylalaninal methyl ester (0.375 g, 0.8 mmol) in anhydrous toluene (10 ml), at −78° C. under nitrogen is added a solution of 1.2 M diisobutyl aluminum hydride in hexane (3 ml, 3.5 mmol). The reaction is stirred at −78° C. for one hour, then hydrolized with a saturated solution of potassium sodium tartrate. The temperature is allowed to rise to room temperature. The mixture is acidified until pH ~3 with a 1M solution of potassium hydrogenosulfate and extracted three times with ethyl acetate (3×20 ml). The organic layer is dried over anhydrous magnesium sulfate. Filtration and removal of the solvent invacuo affords a residue which is purified by flash chromatography (silica gel: 1:1 ethyl acetate/cyclohexane). The title compound is obtained with 20% yield (70 mg).

$R_f \cong 0.50$ (ethyl acetate).

EXAMPLE 23

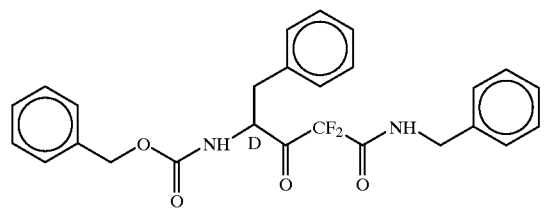

Preparation of 4-D-(N-Benzyloxycarbonyl)amino-2,2-difluoro-3-oxo-5-phenyl-N-benzyl pentanamide Step A: N-Benzyloxycarbonyl-D-phenylalanine,N,O-dimethyl hydroxamate To a solution of Z(D)Phe-OH (31 g, 0.103 mol) in anhydrous methylene chloride (300 mL) at 0° C. are added N,N'-dicyclohexyl carbodiimide (21.21 g, 0.103 mol) and hydroxybenzotriazole hydrate (15.76 g, 0.103 mol). Stir at 0° C. for 10 minutes, add N,O-dimethylhydroxylamine, HCl (10.04 g, 0.103 mol) and N-methyl morpholine (10.40 g, 0.103 mol) to the reaction and stir at 25° C. for 12 hours.

Filter the mixture, wash with methylene chloride and concentrate the filtrate under vacuo to provide the crude 30 hydroxamate as an oil. Purify the crude residue by flash chromatography (silica gel: ethyl acetate/cyclohexane 4:6) to provide the title compound as a colorless oil (29.8 g, 85% yield).

$R_f \cong 0.37$ (ethylacetate:cyclohexane 1:1).

Step B: N-Benzyloxycarbonyl-D-phenylalaninal

Lithium aluminum hydride (3.8 g, 0.1 mol) is added to a solution of the hydroxamate (29 g, 0.084 mol) in anhydrous diethyl ether (500 mL) at 0° C. under an inert atmosphere. Stir for 1 hour. Add cautiously a 1M solution of potassium hydrogenosulphate (150 mL). Separate the phases and extract the aqueous layer twice with diethylether (2×150 mL). Wash the combined organic layers with an aqueous 3N hydrochloric acid (50 mL), water (50 mL) and brine (50 mL). Dry over anhydrous magnesium sulphate, filter and concentrate under vacuum to provide the title compound. Purify by recrystallization in ethyl acetate/pentane (10.9 g, 46% yield).

$R_f \cong 0.41$ (ethylacetate:cyclohexane 1:1).

Step C: 4-D-N-Benzyloxycarbonylamino-2,2-difluoro-3-hydroxy-5-phenyl pentanoic acid, ethyl ester To a suspension of zinc (2.30 g, 35.2 mAtq) in anhydrous tetrahydrofuran (15 mL) under nitrogen, add a mixture of ethylbromodifluoroacetate (7.14 g, 35.2 mmol) and N-benzyloxycarbonyl-(D)-phenylalaninal (4.75 g, 16.8 mmol) in anhydrous tetrahydrofuran (30 mL). After addition of 2 mL of this solution, heat the suspension at reflux with stirring. Maintain gentle reflux by slow addition (dropwise) of the rest of the solution of aldehyde and bromoester. Stir the mixture for 4 hours at room temperature after completion of the addition. Hydrolyze by addition of 1M potassium hydrogensulphate (30 mL). Extract the solution with ethyl acetate (3×30 mL). Wash the combined organic layers with brine and dry over anhydrous magnesium sulphate. Filter and concentrate the filtrate under vacuum. Purify the crude residue by flash chromato-graphy (silica gel, ethyl acetate-:cyclohexane 1:9) to provide the title compound as a white solid (2.95 g, 43% yield).

$R_f \approx 0.50$ (ethylacetate:cyclohexane 1:1). Anal. Calcd for $C_{21}H_{23}NO_5F_2$: C, 61.91; H, 5.69; N, 3.44. Found: C, 62.19; H, 5.75; N, 3.55.

Step D: 4-D-N-Benzyloxycarbonylamino-2,2-difluoro-3-hydroxy-5-phenyl-N-benzylpentanamide Stir a solution of the ester of Example 23, Step C (1.42 g, 3.5 mmol) and benzylamine (1.93 g, 18 mmol) in anhydrous tetrahydrofuran (10 mL) at 25° C. for 12 hours. Take off with ethyl acetate (100 mL) and wash three times with 1N aqueous hydrochloric acid (3×15 mL), water (15 mL) and brine (15 mL). Dry over anhydrous magnesium sulphate, filter and concentrate the filtrate. Purify the crude residue by flash chromatography (silica gel, gradient ethyl acetate:cyclohexane 3:7 to ethyl acetate). The title compound is obtained as a white solid (1.16 g, 71% yield).

$R_f \approx 0.40$ (ethylacetate:cyclohexane 1:1) MS: MH$^+$=469.

Step E: 4-D-(N-Benzyloxycarbonyl)amino-2,2-difluoro-3-oxo-5-phenyl-N-benzyl pentanamide To a mixture of Dess-Martin periodinane reagent (0.36 g, 0.85 mmol) in dry methylene chloride, add a solution of the alcohol of Example 23, Step D (0.11 g, 0.23 mmol) in methylene chloride and N,N-dimethyl formamide (2 mL, 1 mL), and stir at 25° C. for 3 hours. Evaporate the solvent under vacuum, and purify the crude residue by flash chromatography (silica gel, ethyl acetate:cyclohexane 1:1) followed by recrystallization (ethyl acetate/pentane). The title compound is obtained as a white solid (0.074 g, 69% yield).

$R_f \approx 0.45$ (ethylacetate:cyclohexane 1:1). Anal. Calcd for $C_{26}H_{24}N_2O_4F_2 \cdot 0.5\ H_2O$: C, 65.68; H, 5.30; N, 5.89 Found: C, 66.05; H, 5.22; N, 5.97. MS: MH$^+$=467 MP: 130° C.

EXAMPLE 24

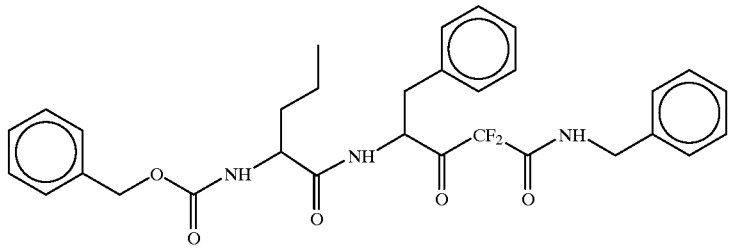

Preparation of 4-(N-Benzyloxycarbonyl-L-norvalyl)amino-2,2-difluoro-3-oxo-5-phenyl-N-benzyl pentanamide Step A: 4-(N-Benzyloxycarbonyl-L-norvalyl)amino-2,2-difluoro-3-hydroxy-5-phenyl-N-benzyl pentanamide The title compound is obtained from the amine described in Example 7, Step D, and carbobenzoxy-L-norvaline following the coupling procedure described in Example 8, Step C (65% yield).

$R_f \approx 0.40$ (ethylacetate:cyclohexane 1:1) MS: MH$^+$=568.

Step B: 4-(N-Benzyloxy-L-norvalyl)amino-2,2-difluoro-3-oxo-5-phenyl-N-benzyl pentanamide To a suspension of Dess-Martin periodinane (0.271 g, 0.64 mmol) in methylene chloride (5 mL) add the alcohol described in Example 23, Step A (0.09 g, 0.16 mmol) in 5 mL dichloromethane. Stir at 25° C. for 4 hours. Concentrate under vacuum and purify the crude residue by flash chromatography (silica gel, ethyl acetate:cyclohexane 2:8) followed by recrystallization (ethyl acetate/pentane). The title compound is obtained as a white solid (0.04 g, 45% yield).

$R_f \approx 0.41$ (ethylacetate:cyclohexane 1:1) MS: MH$^+$=566 Anal. Calcd for $C_{31}H_{33}N_3O_5F_2 \cdot 0.5\ H_2O$: C, 64.80; H, 5.96; N, 7.31 Found: C, 64.82; H, 5.92; N, 7.16.

EXAMPLE 25

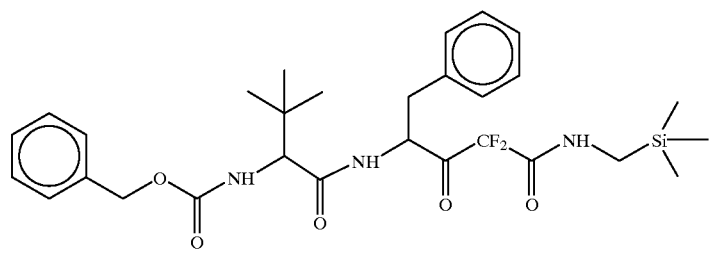

Preparation of 4-(N-Benzyloxycarbonly-L-tert-leucyl)amino-2,2-difluoro-3-oxo-5-phenyl-N-trimethvlsilylmethyl pentanamide Step A: 4-(N-Benzyloxycarbonyl-L-tert-leucyl)amino-2,2-difluoro-3-hydroxy-5-phenyl-N-trimethylsilylmethyl pentanamide A mixture of the amine described in Example 8, Step B [prepared as its trifluoroacetic acid salt (0.222 g, 0.5 mmol)], N-methyl morpholine (115 µL, 1.05 mmol) and carbobenzoxy-L-tert-leucyl anhydride [previously prepared in Situ from the acid and N,N'-dicyclohexyl carbodiimide in 3 mL of dimethylformamide (0.566 g, 1.1 mmol)] is kept overnight under stirring at room temperature. The mixture is diluted with ethyl acetate, washed twice with water and the aqueous layer concentrated under vacuum. The crude residue is purified by flash chromatography (silica gel, ethyl acetate:petroleum ether 3:7) to give the title alcohol in 52% yield (0.15 g)

$R_f \cong 0.69$ (ethylacetate:petroleum ether 4:6)

Step B: 4-(N-Benzyloxycarbonyl-L-tert-leucyl)amino-2,2-difluoro-3-oxo-5-phenyl-N-trimethylsilylmethyl pentanamide The title ketone is prepared in 69% yield from the alcohol of Example 25, Step A, using the Swern oxidation procedures described in Example 8, Step D.

$R_f \cong 0.30$ (ethylacetate:petroleum ether 3:7).

Anal. Calcd for $C_{29}H_{39}F_2N_3O_5Si$, 0.5 $H_2O$: C, 59.57; H, 6.90; N, 7.19 Found: C, 59.65; H, 6.89; N, 7.00.

EXAMPLE 26

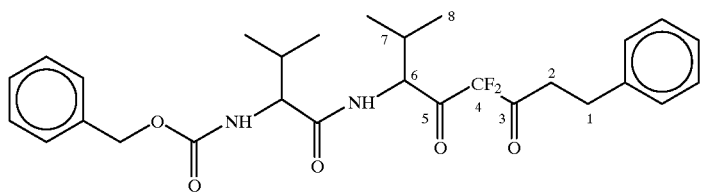

Preparation of 6-(N-Benzyloxycarbonyl-L-valyl)amino-4,4-difluoro-1-phenyl-7-methyl-3,5-dioxooctane Step A: Benzyloxycarbonyl-L-valyl-valinal The title aldehyde is prepared in 43% yield from-N-benzyl-oxycarbonyl-L-valyl-L-valine, ethyl ester using the reduction method described in Example 12, Step D.

$R_f \cong 0.25$ (silica gel ethylacetate:petroleum ether 3:7) MS: $MH^+ = 335$, $MNH_4^+ = 352$.

Step B: 6-(N-Benzyloxycarbonyl-L-valyl)amino-4,4-difluoro-1-phenyl-7-methyl-5-hydroxy-3-oxooctane The title difluoro alcohol is obtained in 39% yield from the aldehyde of Example 26, Step A, and 1-chloro-1,1-difluoro-2-oxo-4-phenylbutane following the procedure described in Example 6, Step C.

$R_f \cong 0.43$ (silica gel ethylacetate:petroleum ether 3:7) MS: $MH^+ = 519$, $MNH_4^+ = 536$.

Anal. Calcd for $C_{28}H_{36}F_2N_2O_5$: C, 64.85; H, 7.00; N, 5.40 Found: C, 65.11; H, 7.25; N, 5.22.

Step C: 6-(N-Benzyloxycarbonyl-L-valyl)amino-4,4-difluoro-1-phenyl-7-methyl-3,5-dioxooctane The title diketone is obtained from the alcohol of Example 26, Step C, using the Swern oxidation described in Example 8, Step D (34% yield).

$R_f \cong 0.31$ (silica gel ethylacetate:petroleum ether 2:8) MS: $MH^+ = 517$, $MNH_4^+ = 534$.

Anal. Calcd for $C_{28}H_{34}F_2N_2O_5$: C, 65.10; H, 6.63; N, 5.42 Found: C, 65.22; H, 6.90; N, 5.05.

EXAMPLE 27

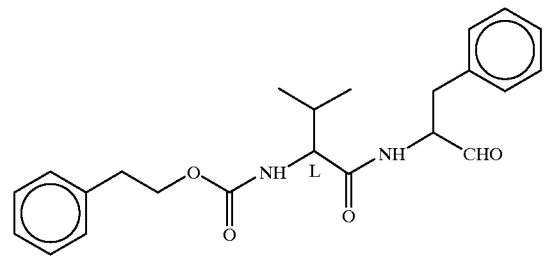

Preparation of (1-Phenethyl-2-oxy)carbonyl-L-valyl-phenylalaninal

Step A: (1-Phenethyl-2-oxy)carbonyl-L-valine, methyl ester

To a suspension of carbonyldiimidazole (4.02 g, 24.8 mmol) in anhydrous dichloromethane (10 mL) is added valine methyl ester (1.63 g, 12.4 mmol) in dichloromethane (3 mL) dropwise via a syringe (over a 3 minute period). The reaction mixture becomes homogeneous and is continued to stir at room temperature for 15 minutes. The mixture is then concentrated invacuo to give a white solid. The solid is suspended in anhydrous toluene (10 mL) and 2-phenylethanol (7.4 mL, 62.0 mmol) is added dropwise. The reaction mixture becomes clear and is heated at 68° C. (oil bath) for 3 hours. The solvent is removed by rotoevaporation and the residue is taken up in dichloromethane, washed with water twice and brine, dried over magnesium sulphate, filtered, and concentrated invacuo. The crude material is purified on silica gel with hexane:petroleum ether (80:20 to 60:40) as eluent to give 2.51 g (72%) of the desired product.

Step B: (1-Phenethyl-2-oxy)carbonyl-L-valine

To a mixture of the carbamate of Example 27, Step A (0.43 g, 1.54 mmol) in 5 mL of methanol and 1 mL of water is added lithium hydroxide (1.0 M, 1.4 mL, 1.4 mmol). The reaction is heated to reflux (80° C.) for 3 hours and stirred at room temperature overnight. More lithium hydroxide (1M, 0.5 mL) is added and the reaction is continued to stir at room temperature for another 3 hours. The reaction mixture is concentrated invacuo. Dichloromethane and water are added. The two layers are separated, and the aqueous layer is acidified to pH 1 with HCl (1M) and extracted with dichloromethane twice. The combined organic layers are dried over magnesium sulphate, filtered, and concentrated in vacuo to yield 0.33 g (81%) of the desired acid.

Step C: (1-Phenethyl-2-oxy)carbonyl-L-valyl-L-phenyl-alaninol

To a solution of the acid of Example 27, Step C (0.33 g, 0.88 mmol), phenylalaninol (0.3 g, 1.24 mmol), 1-hydroxybenzotriazole (0.27 g, 1.24 mmol), N-methyl morpholine (0.22 mL, 1.24 mmol) in dichloromethane (10 mL) is added 1-(3-dimethylaminopropyl)-3-ethylcarbodiimide (0.33 g, 1.24 mmol). The reaction mixture is stirred at room temperature overnight, diluted with dichloromethane, washed with iN HCl, water, saturated aqueous sodium bicarbonate, water and brine, dried over magnesium sulphate, filtered and concentrated invacuo. The remaining white fluffy solid is crystallized from hexane/ethyl acetate to yield the title compound as a white solid (0.35 g, 71%)

Step D: (1-Phenethyl-2-oxy)carbonyl-L-valyl-phenylalaninal

The title aldehyde is obtained in 54% yield from the alcohol of Example 27, Step C, using the oxidation method described in Example 8, Step D.

Anal. Calcd for $C_{23}H_{28}N_2O_4$: C, 69.67; H, 7.12; N, 7.07 Found: C, 69.61; H, 7.22; N, 6.77.

EXAMPLE 28

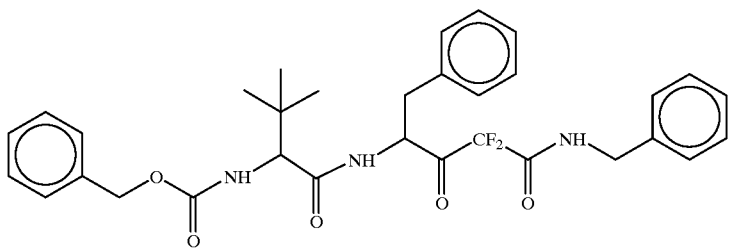

Preparation of 4-(N-Benzyloxycarbonyl-L-tert-leucyl) amino-2,2-difluoro-3-oxo-5-phenyl-N-benzyl pentanamide Step A: 4-(N-Benzyloxycarbonyl-L-tert-leucyl)amino-2,2-difluoro-3-hydroxy-5-phenyl-N-benzyl pentanamide The title compound is obtained from the amine depicted in Example 7, Step D, and carbobenzoxy-L-tert-leucine using a coupling procedure analogous to that described in Example 25, Step A (77% yield).

$R_f \approx 0.37$ (silica gel ethylacetate:petroleum ether 4:6).

Step B: 4-(N-Benzyloxycarbonyl-L-tert-leucyl)amino-2,2-difluoro-3-oxo-5-phenyl-N-benzyl pentanamide The title final compound is prepared in 85% yield from the alcohol of Example 28, Step A, using the Swern oxidation procedure analogous to that described in Example 8, Step D. $R_f \approx 0.24$ (silica gel ethylacetate:petroleum ether 3:7).

Anal. Calcd for $C_{32}H_{35}F_2N_3O_5$: C, 66.31; H, 6.03; N, 7.25 Found: C, 65.99; H, 6.15; N, 7.13.

EXAMPLE 29

The activity of the compounds of this invention to prevent or reduce the accumulation of β-amyloid plaques and thus the usefulness in the treatment of senile dementia of the Alzheimer's type and other conditions known to be associated with the formation of β-amyloid plaque such as Down's syndrome can be demonstrated by various invitro and in vivo models of β-amyloid plaque formation. For example the ability of the compounds of this invention to prevent or reduce the accumulation of β-amyloid plaques can be demonstrated by several cellular and cell free in vitro methods described as Assay's 1–3 as follows. These assays make use of the fact that native β-APP is expressed by all cells and is processed to produce 11-12 KDa C-terminal fragments and β-amyloid. The endogenous level of β-APP expression can be enhanced if desired by transfecting β-APP cDNA sequences, e.g., β-APP (751) into the cells using standard methodology.

IN VITRO ASSAYS

Assay #1: Immunoprecipitation

Cells; CHO-Kl (Chinese Hamster Ovary; ATCC origin) cell line stably transfected to express large amounts of βAPP-695, and referred to as "CP-6-36" are used for screening inhibitors. Other mammalian cultured cell lines can also be used and have been used. For example, the human neuronal cell line SK-N-MC (ATCC origin) gives good results under the same assay conditions. Transfection with βAPP-695 is not a requisite of βA4 production; it merely enhances the βA4 signal. In preparation for an experiment, CP-6-36 cells are seeded at low density in 10 cm dishes and grown for two to four days to a confluent monolayer (~1.5×10^7 cells per dish) in a 37° C./5% $CO_2$ incubator; growth media consists of DMEM 21/Coon's F12 (1:1) +10% FBS (fetal bovine serum) +50 U/mL penicillin and 50 μg/mL streptomycin.

Treatment: All compounds are initially screened on CP-6-36 cells at a dose of 200 μM. Prior to testing, a 20 mM stock of each compound to be tested is prepared using cell culture grade DMSO as a solvent. Each 20 mM stock compound is then diluted 100-fold into serum free EMEM media deficient in the amino acids cysteine and methionine ("Cys-/Met-EMEM"), giving a 200 μM final concentration of compound in the media. To begin the experiment the cells are "starved" for cysteine and methionine by washing the cell monolayers 3 times with 3 mL/dish of Cys-/Met- EMEM, then incubating (37° C./5% $CO_2$) with 3 mL/dish of the same media for 15 minutes. This media is aspirated from the dishes, then media containing the compounds at 200 μM is added at 3 mL/dish. These plates and a "control" dish (3 mL/dish Cys-/Met- EMEM containing 1% DMSO and no compound) are incubated as above for 15 minutes. This media is aspirated, then to each dish an additional 3 mL of the media from the previous step now containing $^{35}$S-Trans label ($^{35}$-S labeled cysteine and methionine) at ~150 μCi/mL is added. The cells are incubated as above for 4 hours.

Harvest: At the end of the 4 hour labeling period, the cells are observed under the microscope for overall appearance and to check for gross toxicity effects of the compounds, after which the dishes of cells are placed on ice. The conditioned media from each dish is transferred to 15 mL conical screw-cap tubes, centrifuged at 2000 rpm for 10 minutes and transferred to a set of similar tubes, leaving behind any pelleted cells. The labeled cell mono-layers are washed three times with 2 mL/dish phosphate-buffered saline (PBS), then 1 mL of a buffer which promotes cell lysis (5% Triton X-114; 20 mM Tris, pH 7.5; 300 mM NaCl; protease inhibitors) is added to each dish, followed by a 10 minute incubation on ice. The cell lysates are scraped from the dishes and transferred to 1.5 mL microfuge tubes. The lysates are then sonicated for 4 minutes on ice, spun at high speed in a microfuge for 10 minutes, then transferred to 15 mL conical screw-cap tubes, leaving behind the pellet of cell debris.

Immunoprecipitation: In preparation for immunoprecipitation, the lysates harvested above are diluted in 5 mL of 1×RIPA buffer (10 mM Tris, pH 8.0; 150 mM NaCl; 0.125% NaN$_3$; 1% Triton X-100; 1% deoxycholate; 0.1 SDS); the conditioned media samples are immunoprecipitated without dilution. Both conditioned media and lysates are first precleared by adding 5 μL of normal rabbit serum to each sample, rocking 10 minutes at room temperature, followed by the addition of 100 μL 10% protein A-Sepharose (PAS) in RIPA buffer, and rocking at room temperature for 1.5 hours. The samples are then centrifuged at 3000 rpm, and the supernatants are transferred to new 15 mL tubes. The precleared lysates are then immunoprecipitated by adding 30 μL of an antibody which recognizes the carboxyl terminus of βSAPP to each tube, rocking for 10 minutes at room temperature, followed by the addition of 100 μL of 10% PAS and rocking at room temperature for 1.5 hours. The precleared conditioned media samples are immunoprecipitated identically, however 45 μL of an antibody which recognizes βA4 is used instead of the carboxyl terminal directed antibody. All samples are then centrifuged for 1 minute at 3000 rpm to pellet the PAS-antibody complexes, and the resulting pellets are washed extensively; 4 times with a high salt buffer (50 mM Tris, pH 7.5; 500 mM NaCl; 5 mM EDTA; 0.5% Nonidet P-40), 3 times with a low salt buffer (50 mM Tris, pH 7.5; 150 mM NaCl; 5 mM EDTA; 0.5 Nonidet P-40), and 2 times with 10 mM Tris buffer, pH 7.5.

Gel electrophoresis: The washed pellets are boiled for 5 minutes in 50 μL of 2×Laemmli gel loading buffer. These samples as well as molecular weight markers are loaded onto a 16.5% SDS-polyacrylamide gel with Tris/Tricine reservoir buffers. The gel is run at 90V for ~18–20 hours, fixed in 20% methanol/20% acetic acid, and dried onto filter paper at 65° C. for 2 hours. Autoradiography is used to visualize the results.

Analysis: Results are obtained by analysis of the autoradiogram. A positive acting compound is one which inhibits the 4 kDa βA4 protein band relative to the control sample, and additionally some may increase levels of the 9–12 kDa C-terminal protein bands relative to the control sample. Quantitation of inhibition of βA4 or increase of C-terminal bands can be made by densitometric scanning of the bands, normalized to control bands. A negative acting compound is one which shows no change in the yield of 4 kDa βA4 or 9–12 kDa C-terminal protein bands, relative to the bands from the control sample.

Additional testing: If a compound is found to be active (i.e., substantial inhibition of 4 kDa βA4 with concomitant increase in C-terminal fragments, by gel analysis), then a dose response experiment is performed to determine the lowest dose of compound necessary to elicit above effects. The dose range typically used is 12.5–300 μM, and with the exception of these dose changes, the experiment is done identically as described above. If a compound is found to be only slightly active or not active at all, the experiment is repeated using a higher dose, typically 400 μM. If a compound is found to be toxic (i.e., cells appear unhealthy by observation under the microscope, or lysates appear to not have been labeled well after gel analysis), then the compound is tested again at lower doses, for example: 25, 50 and 100 μM, to determine the effect of the compound at a non-toxic dose.

Assay #2: Radioimmunoassay

Preparation and Speak concentration of media for the RIA: Cultured mammalian cells such as Chinese hamster ovary (CHO) cells or human neuronal SK-N-MC cells produce β-amyloid and secrete this peptide into the culture medium. If cells are treated with potential inhibitors of β-amyloid formation, no soluble β-amyloid would be found in the medium of the treated cells. As with Assay #1, varying doses of inhibitory compounds can be tested beginning with 200 μM. For CHO cells, both wild type and β-APP695 transfected, 10 cm plates are incubated in 2 mL EMEM (serum free) for 4 to 6 hours at 37° C. in the presence or absence of inhibitory compounds to be evaluated. The medium is removed and centrifuged for 10 minutes at 1500 rpm (Sorvall RT6000B) to remove any cells/debris. The medium is either used immediately or stored at −20° C. The Sepak C18 step is performed to remove salts and other unwanted contaminants and to concentrate the β-amyloid peptides. Medium sample (2 ml) is passed through a C18 Sepak cartridge and the cartridge is washed in 2 ml 5% CH$_3$CN in 0.1% TFA. The runthrough and the 5% CH$_3$CN wash are discarded. The cartridge is eluted wit h 2 mL 25% CH$_3$CN in 0.1% TFA followed by 2 mL elution in 50% CH$_3$CN in 0.1% TFA. Both elutions are collected and dried in the speedvac and taken up in 125 μL to 250 μL of 10% isopropanol in water for assaying in the RIA. The 25% CH$_3$CN fraction contains most of the phenol red from the media but no β-amyloid peptide. The 50% CH$_3$CN fraction contains the β-amyloid peptides.

Preparation and HPLC purification of $^{125}$I labeled β-amyloid 1-40: Synthetic β-amyloid 1-40 (10 μg) is labeled with $^{125}$I (lmci) by the Chloramine T method. The reaction is carried out at room temperature. In an eppendorf tube, 10 μL of $^{125}$I (lmci in NAOH solution) is added to 10 μL of β-amyloid 1-40 (lmg/mL in 20% Isopropanol) and 80 μL 0.1M NaPhosphate, pH 7.4 and mixed. The reaction is initiated by adding 30 μL Chloramine-T (lmg/mL, in 0.1M NaPhosphate, pH 7.4) mixing and incubating 1 minute. The reaction is stopped by adding 150 μL NaMetabisulfite (2 mg/mL, 0.1M NaPhosphate, pH 7.4).

The reaction mixture (280 μL) is diluted with equal volume of water and run on a Sepak C18 cartridge to separate the labeled peptide. The Sepak is washed twice in 5% CH$_3$CN (1 mL each) and eluted three times in 50% CH$_3$CN (1 mL each) and washed again twice in 95% CH$_3$CN (1 mL each). Almost all of the labeled peptide elutes in the first 50% CH$_3$CN elution. This elution is stored at −70° C. and purified by HPLC as needed for the RIA.

The labeled peptide is purified by reverse phase HPLC on a C8 cartridge (4.6 mm×3 cm, Brownlee). The column is run in a linear gradient from 5% to 45% CH$_3$CN in 0.1% TFA in 30 minutes at a flow rate of 0.5 ml/min. Fractions (0.5 mL) are collected and counted. The peak fraction containing the labeled peptide is stored at −20° C. and used within 3 days in the RIA.

Radioimmunoassay: The buffers used in the RIA are 1) RIA buffer: 0.1M NaPhosphate, pH 7.4 containing 0.1% BSA and 0.1% Triton-X-100. 2) Sample buffer: 10% Isopropanol in water. 3) Tracer buffer: 0.2M NaPhosphate, pH 7.4 containing 0.1% BSA in 0.1% Triton-X-100. The B-amyloid specific antibodies are used at dilutions where approximately 30% of the labeled peptide is bound in the absence of competing ligand. The dilutions of the antibodies are prepared in RIA buffer. The antibodies used in the RIA include three different sera raised to human β-amyloid 1-40 synthetic peptide (BA#1, BA#2, and 6514). BA#1 is used at final dilution of 1/900, BA#2 at 1/1600 and 6514 at 1/2500. The HPLC purified labeled peptide is diluted in tracer buffer to give between 7000 and 9000 cpm in 50 μL. Total displacement is done in the presence of high concentration (2.5 μM) of β-amyloid 1-40. The β-amyloid 1-40 standards are prepared in sample buffer. The assay volume is 200 μL. Components are added in the following order:

100 μL Ab in RIA buffer

50 μL Unknown sample or standard or TD in sample buffer

50 μL Labeled peptide (7000–9000 cpm in tracer buffer)

The samples are mixed and incubated overnight at 4° C. To separate the bound counts from the free counts, the assay is terminated with polyethylene glycol (PEG). To each assay tube, 50 μL of normal rabbit serum is added, followed by 800 μL of PEG (MW6000–8000, 15.8% in RIA buffer). The samples are incubated for 10 minutes at 4° C. and centrifuged 3200 rpm, 20 minutes (Sorvall, RT600B). The supernatant is aspirated and the pellets are counted in the gamma counter.

Analysis: Results from antibody binding are interpreted based on displacement of the labeled β-amyloid tracer. A positive result is one in which no displacement of tracer is observed, i.e., medium does not contain secreted β-amyloid indicating the compound tested is effective in inhibiting β-amyloid production. A negative result is one in which displacement of tracer for antibody binding is seen and equivalent to untreated control cells.

An enzyme linked immunosandwich assay (ELISA) can also be employed to identify active compounds. Cultured mammalian cells (such as CHO CP-6 or SK-N-MC) producing β-amyloid protein are prepared and treated with compounds as described for Assay #1 except that radiolabelling of cell protein is eliminated. Conditioned media from treated cell cultures is harvested and clarified of cellular debris by low-speed centrifugation. The conditioned media is then assayed in a 96 well ELISA format utilizing -amyloid-specific antibodies. One β-amyloid antibody serves as the capture reagent for the β-amyloid present in the media samples, the second β-amyloid-specific antibody which recognizes a different epitope on the β-amyloid protein serves as a component of the detector complex. The second β-amyloid antibody is conjugated with biotin which can be detected by strept-avidin. A third antibody which is coupled to horseradish peroxidase is used to detect the β-amyloid:antibody;strept-avidin complex. Addition of o-phenylenediamine substrate plus $H_2O_2$ and citrate phosphate pH 5 allows for peroxidase activity which is quantitated by reading the colorimetric change in the mixture at $OD^{490nm}$. Typically, serial three-fold dilutions of each medium sample is made in the 96 well plate in addition to a standard, synthetic β-amyloid 1-40 protein. A positive result is one in which little or no reactivity, i.e., adsorbance at $OD^{490nm}$, is obtained indicated the absence of β-amyloid protein in the medium sample as a result of inhibition by the compound tested. Partially active inhibitors would give some but not equivalent adsorbance at $OD^{490nm}$ to a control medium sample from untreated cells. Precise quantitation can be achieved by comparing sample values to the standard.

IN VIVO ASSAYS

The activity of the compounds of this invention to prevent or reduce the accumulation of β-amyloid plaques can be demonstrated in a transgenic model of β-amyloid plaque accumulation (e.g., transgenic mouse or transgenic rat) and in a dog model using dogs with a natural, genetic predisposition to the formation of β-amyloid plaque. Transgenic mice which overexpress human β-APP (751) or β-APP (770) in neuronal cells and display histopathology associated with Alzheimer's disease are described, for example, in PCT/US91/04447. In such animal models, the reduction of histopathology and/or symptoms associated with β-amyloid plaque formation such as memory loss, can be used to demonstrate the ability of the compounds to treat the therapeutic conditions resulting from β-amyloid plaque formation such as Alzheimer's Disease and the memory impairment associated with Down's syndrome.

Since the histopathology in the transgenic mice is more frequent with increased age of the animal, 2 month old mice would be desirable. The 2 month animals would have minimal pathology which would increase with time in the absence of inhibitory drug. All animals in the experiment would be from a single pure bred pedigree. One group of mice (n=12) would receive vehicle only; a second group (n=12) would receive a low dose of drug; a third group (n=12) a moderate dose; and a fourth group (n=12) a high dose. Dosage would be determined from the above assays taking into account body weight, compound half-life, etc. Ideally, mice would be treated for several months. Delivery of the compound could be by injection, oral route, an implant with timed release, etc., as dictated by the compound profile. Evaluation of treatment would be made using immuno-histochemistry to determine the frequency of β-amyloid immunoreactive deposits in 4 coronal midline sections of brain scored by an investigator blinded from the experimental treatment. Another marker of pathology, Alz50 immunoreactivity, would also be scored for frequency of occurrence using the same number of brain tissue sections from all mice in the study. A positive result of drug action would be the absence or reduced frequency of both pathological markers. A physiological and/or behavioral correlate unique to the β-amyloid transgenic mice can also be used to demonstrate drug action.

Some canine races have been reported to have β-amyloid accumulations (Giaccone et al., *Neuroscience Letters* Vol. 114, pp 178–183 (1990)). Aged non-human primates display β-amyloid pathology, as well as memory impairments (Cork et al., *American Journal of Pathology*, Vol.137, pp 1383–1392 (1990)); Podlisny et al., *American Journal of Pathology*, Vol.138, pp 1423–1425 (1991)). Tests with canines and non-human primates would most likely follow a somewhat different experimental design with drug application time being longer.

Any effective amount of a compound of formula 1, or a mixture of more than one of the compounds of formula 1 may be administered to patient to prevent the abnormal deposition of β-amyloid plaque and to treat a disease or condition associated with the abnormal deposition of β-amyloid plaque such as senile dementia of the Alzheimer's type or Down's Syndrome. The specific dosage for preventing the abnormal deposition of β-amyloid plaque and for treating senile dementia of the Alzheimer's type or Down's Syndrome will depend on factors such as size, type, and age of the patient as well as the severity of the disease state or condition, all of which are factors normally familiar to and considered by the attending diagnostician treating the patient. Generally, the compounds are administered at a dose of from 0.2 to 20 milligrams per kilogram of body weight with a dose of 0.5 to 5 mg/Kg being preferred. The compounds can be administered in single or multiple unit dosages containing 25 mg to 250 mg of a compound of formula 1.

For oral administration, the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose or cornstarch. In another embodiment, the compounds of general formula I can be tableted with conventional tablet bases such as lactose, sucrose and cornstarch, in combination with binders, such as acacia, cornstarch or gelatin, disintegrating agents such as potato starch or alginic acid, and a lubricant such as stearic acid or magnesium stearate.

For parenteral administration, the compounds may be administered as injectable dosages of a solution or suspension of the compound in a physiologically acceptable diluent with a pharmaceutical carrier which can be a sterile liquid such as water, alcohols, oils and other acceptable organic solvents, with or without the addition of a surfactant and other pharmaceutically acceptable adjuvants. Illustrative of oils which can be employed in these preparations are those of petroleum, animal, vegetable, or synthetic origin, for example, peanut oil, soybean oil and mineral oil. In general, water, saline, aqueous dextrose and related sugar solutions, ethanol and glycols such as propylene glycol or polyethylene glycol, or 2-pyrrolidone are preferred liquid carriers, particularly for injectable solutions.

The compounds can be administered in the form of a depot injection or cerebral implant preparation which may be formulated in such a manner as to permit a sustained release of the active ingredient. The active ingredient can be compressed into pellets or small cylinders and implanted subcutaneously, intramuscularly, or intracerebrally as depot injections or implants. Implants may employ inert material such as biodegradable polymers or synthetic silicones, for example Silastic®, a silicone rubber manufactured by the Dow-Corning Corporation.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as a membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,291,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

As is true in many classes of compounds generally suitable for any particular pharmacological activity having a therapeutic end-use application, certain subgeneric groups and certain specific members of the class are preferred because of their overall therapeutic index and their biochemical and pharmacological profile. In this instance the preferred compounds are those wherein $P_4$ is a bond.

Applicants prefer those compounds wherein $X_1$ is H or $CF_2C(=O)W$. $C_{1-6}$ alkylene is preferably $C_{1-3}$ alkylene and more preferably methylene or ethylene and most preferably branched chain ethylene. Arylalkyl is preferably benzyl or phenethyl, and aryl is preferably phenyl. The $K-P_4-P_3-P_2$ moiety is preferably a protecting group (K) and one amino acid, which is preferably one of the residues of valine, alanine or phenylalanine. R is preferably benzyl, isopropyl or substituted benzyl having one substituent.

What is claimed is:

1. A compound of the formula IB or the hydrate, stereoisomer or pharmaceutically acceptable salt thereof:

$$K^a{-}P_4{}^a{-}P_3{}^a{-}P_2{}^a{-}NH{-}CH(R^a){-}(C(={=}O))_n{-}X^a \quad \text{(SEQ ID NO:2)} \quad \text{FORMULA IB}$$

wherein $X^a$ is $CF_2C(={=}O)W^a$, wherein $W^a$ is arylalkyl, $NHCH_2Si(C_{1\text{-}6}\ alkyl)_2(Y^a)$, wherein $Y^a$ is $C_{1\text{-}6}$alkyl, $C_{1\text{-}6}$alkenyl, aryl or arylalkyl;

$n$ is 1;

$R^a$ is $C_{1\text{-}10}$ alkyl or benzyl;

$P_2{}^a$ is a residue of Val, tert-leucine, or Nva;

$P_3{}^a$ and $P_4{}^a$ are each bonds; and $K^a$ is hydrogen, a desamino group, formyl, acetyl, succinyl, benzoyl, t-butyloxycarbonyl, carbobenzyloxy, tosyl, dansyl, isovaleryl, methoxysuccinyl, 1-adamanatanesulphonyl, 1-adamantaneacetyl, 2-carboxybenzoyl, phenylacetyl, t-butylacetyl, bis((1-naphthyl)methyl)acetyl, or $-A^a{-}R_z{}^a$ wherein

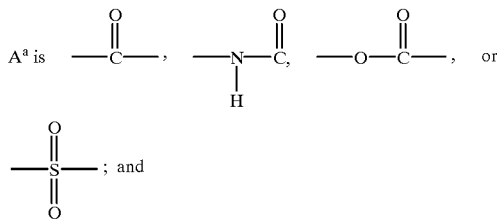

$R_z{}^a$ is an aryl or arylalkyl group in which the aryl group contains 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino, wherein the alkyl group contains 1 to 6 carbons, 5-tetrazolyl, and acylsulfonamido containing from 1 to 15 carbons, provided that when the acylsulfonamido contains an aryl the aryl may be further substituted by a member selected from fluoro, chloro, bromo, iodo and nitro; or

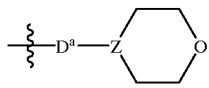

wherein Z is N or CH, and
$D^a$ is a group of the formulae

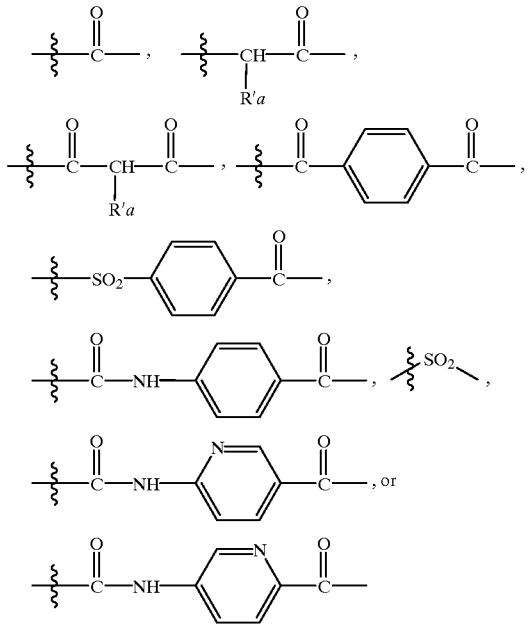

and wherein $R'^a$ is hydrogen or a $C_{1-6}$ alkyl group provided that
when $X^a$ is $CF_2C(=O)$phenethyl then $R^a$ is not benzyl.

2. The compound of claim 1 wherein $K^a$ is carbobenzyloxy.
3. The compound of claim 1 wherein $W^a$ is arylalkyl wherein the alkyl is $C_{1-6}$ and the aryl is phenyl.
4. The compound of claim 1 wherein $Y^a$ is $C_{1-6}$ alkyl.
5. The compound of claim 1 wherein $Y^a$ is aryl wherein the aryl is phenyl.
6. The compound of claim 1 wherein $Y^a$ is arylalkyl wherein the alkyl is $C_{1-6}$ and the aryl is phenyl.
7. The compound of claim 1 wherein $R^a$ is $C_{1-6}$ alkyl.
8. The compound of claim 1 wherein $R^a$ is $C_{1-4}$ alkyl.
9. The compound of claim 1 wherein $W^a$ is arylalkyl, or $NHCH_2Si(C_{1-6}alkyl)_2(Y^a)$, wherein aryl is phenyl and the alkyl is $C_{1-6}$.
10. The compound of claim 1 wherein the compound is 4-(N-Benzyloxycarbonyl-L-tert-leucyl)amino-2,2-difluoro-3-oxo-5-phenyl-N-trimethylsilymethyl pentanamide.
11. The compound of claim 1 wherein the compound is 6-(N-Benzyloxycarbonyl-L-valyl)-amino-4,4-difluoro-1-phenyl-7-methyl-3,5-dioxooctane.
12. A pharmaceutical composition comprising an effective amount of a compound of claim 1 and a pharmaceutically acceptable carrier.
13. 4-(N-Benzyloxycarbonyl-L-norvalyly)amino-2,2-difluoro-3-oxo-5-phenyl-N-benzyl pentanamide.
14. 4-(N-Benzyloxycarbonyl-L-tert-leucyl)amino-2,2-difluoro-3-oxo-5-phenyl-N-benzyl pentanamide.
15. A process of making the compounds of formula IB or the hydrate, stereoisomer, isostere or pharmaceutically acceptable salt thereof:

$$K^a—P_4^a—P_3^a—P_2^a—NH—CH(R^a)—C(=O)—X^a$$
(SEQ ID NO:5)   FORMULA IB wherein
$X^a$ is $CF_2C(=O)W^a$,
wherein $W^a$ is arylalkyl, $NHCH_2Si(C_{1-6}$ alkyl$)_2(Y^a)$,
wherein $Y^a$ is $C_{1-6}$alkyl, $C_{1-6}$alkenyl, aryl or arylalkyl;
$R^a$ is $C_{1-10}$ alkyl or benzyl;
$P_2^a$ is a residue of Val, tert-leucine, or Nva;
$P_3^a$ and $P_4^a$ are each bonds; and
$K^a$ is hydrogen, a desamino group, formyl, acetyl, succinyl, benzoyl, t-butyloxycarbonyl, carbobenzyloxy, tosyl, dansyl, isovaleryl methoxysuccinyl, 1-adamanatanesulphonyl, 1-adamantaneacetyl, 2-carboxybenzoyl, phenylacetyl, t-butylacetyl, bis((1-naphthyl)methyl)acetyl, or $—A^a—R_2^a$ wherein

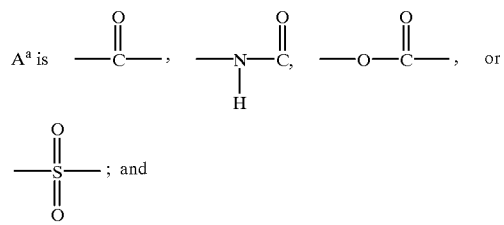

$R_z^a$ is an aryl or arylalkyl group in which the aryl group contains 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino, wherein the alkyl group contains 1 to 6 carbons, 5-tetrazolyl, and acylsulfonamido containing from 1 to 15 carbons, provided that when the acylsulfonamido contains an aryl the aryl may be further substituted by a member selected from fluoro, chloro, bromo, iodo and nitro; or

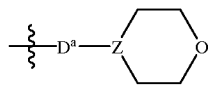

wherein Z is N or CH, and
$D^a$ is a group of the formulae

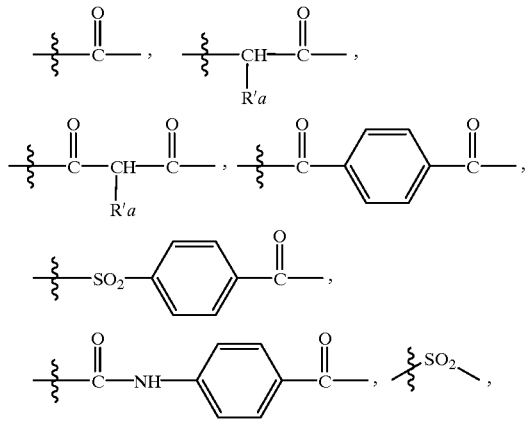

-continued

[structure: -C(=O)-NH-pyridine-C(=O)-, or]

[structure: -C(=O)-NH-pyridine-C(=O)-]

and wherein R'$^a$ is hydrogen or a C$_{1-6}$ alkyl group;
provided that
  when X$^a$ is CF$_2$C(=O)phenethyl then R$^a$ is not benzyl;
comprising the steps of
  coupling K$^a$—P$_4^a$—P$_3^a$—P$_2^a$— as defined herein to H$_2$N—CH(R$^a$)—C(=O)X$^a$ as defined herein, and
optionally obtaining the pharmaceutically acceptable salt thereof,
or alternatively
  coupling K$^a$—P$_4^a$—P$_3^a$—P$_2^a$ — as defined herein to H$_2$N—CH(R$^a$)—CH(OH)X$^a$ as defined herein, and
oxidizing the so-produced compound to obtain K$^a$—P$_4^a$—P$_3^a$—P$_2^a$—NH—CH(R$^a$)—C(=O)—X$^a$
(SEQ ID NO:5)                              FORMULA IB optionally obtaining the pharmaceutically acceptable salt thereof.

16. A method for treating a patient for senile demnentia of the Alzheimer's type by administering to a patient in need thereof a therapeutically effective amount of a compound of formula IB or the hydrate, stereoisomer, isostere or pharmaceutically acceptable salt thereof:

K$^a$—P$_4^a$—P$_3^a$—P$_2^a$—NH—CH(R$^a$)—C(=O)—X$^a$
(SEQ ID NO:5)                              FORMULA IB wherein
  X$^a$ is CF$_2$C(=O)W$^a$,
    wherein W$^a$ is arylalkyl, NHCH$_2$Si(C$_{1-6}$ alkyl)$_2$(Y$^a$),
      wherein Y$^a$ is C$_{1-6}$alkyl, C$_{1-6}$alkenyl, aryl or arylalkyl;
  R$^a$ is C$_{1-10}$ alkyl or benzyl;
  P$_2^a$ is a residue of Val, tert-leucine, or Nva;
  P$_3^a$ and P$_4^a$ are each bonds; and
  K$^a$ is hydrogen, a desamino group, formyl, acetyl, succinyl, benzoyl, t-butyloxycarbonyl, carbobenzyloxy, tosyl, dansyl, isovaleryl, methoxysuccinyl, 1-adamanatanesulphonyl, 1-adamantaneacetyl, 2-carboxybenzoyl, phenylacetyl, t-butylacetyl, bis((1-naphthyl)methyl)acetyl, or —A$^a$—R$_z^a$ wherein A$^a$ is —C(=O)—, —N(H)—C(=O)—, —O—C(=O)—, or

[structure: -S(=O)$_2$-] ; and

R$_z^a$ is an aryl or arylalkyl group in which the aryl group contains 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino, wherein the alkyl group contains 1 to 6 carbons, 5-tetrazolyl, and acylsulfonamido containing from 1 to 15 carbons, provided that when the acylsulfonamido contains an aryl the aryl may be further substituted by a member selected from fluoro, chloro, bromo, iodo and nitro; or

[structure: -D$^a$-Z-morpholine ring with O]

wherein Z is N or CH, and
D$^a$ is a group of the formulae

[structures: -C(=O)-, -CH(R'a)-C(=O)-,
-C(=O)-CH(R'a)-C(=O)-, -C(=O)-phenyl-C(=O)-,
-SO$_2$-phenyl-C(=O)-,
-C(=O)-NH-phenyl-C(=O)-, -SO$_2$-,
-C(=O)-NH-pyridine-C(=O)-, or
-C(=O)-NH-pyridine-C(=O)-]

and wherein R'$^a$ is hydrogen or a C$_{1-6}$ alkyl group;
provided that
  when X$^a$ is CF$_2$C(=O)phenethyl then R$^a$ is not benzyl.

* * * * *

UNITED STATES PATENT AND TRADEMARK OFFICE
CERTIFICATE OF CORRECTION

PATENT NO. : 5,977,074

DATED : Nov. 2, 1999

INVENTOR(S) : Barbara Cordell, et al

It is certified that error appears in the above-identified patent and that said Letters Patent is hereby corrected as shown below:

Column 2, Line 18 reads as "al.," and should read as --et al.,--.

Column 4, Line 34 reads as "1unless" and should read as --1 unless--.

Column 5, Line 49 reads as "Theor preveunds" and should read as --These compounds--.

Column 5, Line 56 reads as "-C($R^a$)" and should read as -- -CH($R^a$)--.

Column 7, Lines 5 to 10 read as "wherein 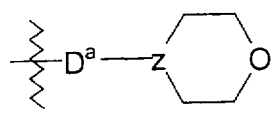 " and should read as 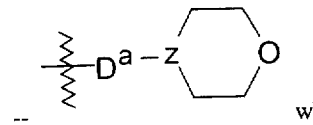 wherein --.

Column 7, Line 50 reads as "$C_{16}$" and should read as --$C_{1-6}$--.

Column 11, Line 43 reads as "insitu" and should read as --*in situ*--.

Column 17, Line 9 reads as "reparing" and should read as --preparing--.

Column 22, Line 56 reads as "knwon" and should read as --known--.

Column 24, Line 15, within the Structure (26) reads as "$Pg_1$" and should read as --$Pg_2$--.

UNITED STATES PATENT AND TRADEMARK OFFICE
CERTIFICATE OF CORRECTION

PATENT NO. : 5,977,074

DATED : Nov. 2, 1999

INVENTOR(S) : Barbara Cordell, et al

It is certified that error appears in the above-identified patent and that said Letters Patent is hereby corrected as shown below:

Column 24, Line 35 reads as

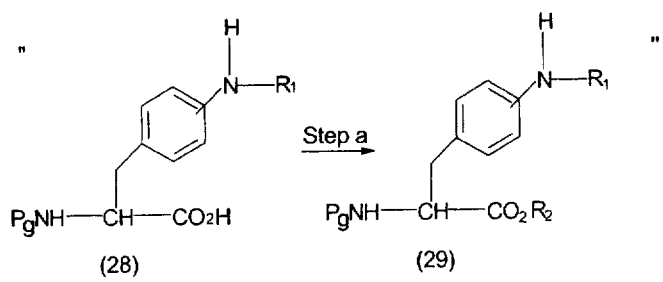

and should read as

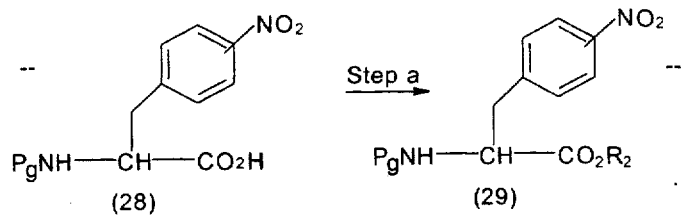

Column 24, Line 50, within structure (31) reads as "$KP_4P_3P_2\text{-}CH\text{-}CO_2R_2$" and should read as --$KP_4P_3P_2NH\text{-}CH\text{-}CO_2R_2$--.

UNITED STATES PATENT AND TRADEMARK OFFICE
CERTIFICATE OF CORRECTION

PATENT NO. : 5,977,074
DATED : Nov. 2, 1999
INVENTOR(S) : Barbara Cordell, et al It is certified that error appears in the above-identified patent and that said Letters Patent is hereby corrected as shown below:

Column 24, Line 60, within Structure (32) reads as "$KP_4P_3P_2$-CH-CHO" and should read as --$KP_4P_3P_2$NH-CH-CHO--.

Column 26, Line 53 reads as "are the coupled to" and should read as --are coupled to--.

Column 31, Line 35 reads as "of one ordinary" and should read as --one of ordinary--.

Column 34, Line 3 reads as "$C_{20}$ $OH_{28}$" and should read as --$C_{20}$ $H_{28}$--.

Column 34, Line 61 reads as "Dimethylhydroxylaminee•HC1" and should read as --Dimethylhydroxylamine•HC1--.

Column 35, Line 41 reads as "Dimethylhydroxylaminee•HC1" and should read as --Dimethylhydroxylamine•HC1--.

Column 36, Line 25 reads as "dimethylmorpholinel" and should read as --dimethylaminopropyl--.

Column 41, Line 55 reads as "benzyloxY" and should read as --benzyloxy--.

Column 43, Line 41 reads as "wis" and should read as --was--.

Column 43, Line 56 reads as "iN" and should read as --1N--.

Column 45, Line 48 reads as "invacuo" and should read as --*in vacuo*--.

Column 46, Line 1 reads as "invacuo" and should read as --*in vacuo*--.

Column 46, Line 20 reads as "-L-valvl-" and should read as -- -L-valyl- --.

Column 48, Line 7 reads as "invacuo" and should read as --*in vacuo*--.

Column 48, line 12 reads as "$[MNH_4]^{30}$" and should read as --$[MNH_4]^+$--.

Column 48, Line 45 reads as "invacuo" and should read as --*in vacuo*--.

UNITED STATES PATENT AND TRADEMARK OFFICE
CERTIFICATE OF CORRECTION

PATENT NO.   : 5,977,074

DATED        : Nov. 2, 1999

INVENTOR(S) : Barbara Cordell, et al

It is certified that error appears in the above-identified patent and that said Letters Patent is hereby corrected as shown below:

Column 48, Line 62 reads as "invacuo" and should read as --*in vacuo*--.

Column 48, Line 65 reads as "[EMH]$^+$" and should read as --[MH]$^+$--.

Column 49, Line 54 reads as "invacuo" and should read as --*in vacuo*--.

Column 49, Line 58 reads as "invacuo" and should read as --*in vacuo*--.

Column 50, Line 17 reads as "invacuo" and should read as --*in vacuo*--.

Column 50, Line 18, reads as "ethylacetate" and should read as --ethyl acetate--.

Column 50, Line 49 reads as "invacuo" and should read as --*in vacuo*--.

Column 50, Line 56 reads as "phenylanine phenylalanine" and should read as --phenylalanine--.

Column 51, Line 1 reads as "inuacuo" and should read as --*in vacuo*--.

Column 51, Line 27 reads as "remtial" and should read as --removal--.

Column 51, Line 28 reads as "invacuo" and should read as --*in vacuo*--.

Column 51, Line 64 reads as "invacuo" and should read as --*in vacuo*--.

Column 53, Line 5 reads as "invacuo" and should read as --*in vacuo*--.

Column 53, Line 14 reads as "]3-3-methyl" and should read as --]-3-methyl--.

Column 53, Line 21 reads as "invacuo" and should read as --*in vacuo*--.

Column 53, Line 41 reads as "invacuo" and should read as --*in vacuo*--.

Column 53, Line 67 reads as "phenylalaninal" and should read as --phenylalanine--.

Column 54, Line 10 reads as "invacuo" and should read as --*in vacuo*--.

UNITED STATES PATENT AND TRADEMARK OFFICE
CERTIFICATE OF CORRECTION

PATENT NO. : 5,977,074
DATED : Nov. 2, 1999
INVENTOR(S) : Barbara Cordell, et al It is certified that error appears in the above-identified patent and that said Letters Patent is hereby corrected as shown below:

Column 54, Lines 41 and 42 read as "crude 30 hydroxamate" and should read as --crude hydroxamate--.

Column 56, Line 64 reads as "Benzyloxycarbonly" and should read as --Benzyloxycarbonyl--.

Column 57, Line 8 reads as "in Situ" and should read as --*in situ*--.

Column 58, Line 23 reads as "invacuo" and should read as --*in vacuo*--.

Column 58 Line 41 reads as "invacuo" and should read as --*in vacuo*--.

Column 58, Line 52 reads as "invacuo" and should read as --*in vacuo*--.

Column 59, Line 1 reads as "iN" and should read as --1N--.

Column 59, Line 3 reads as "invacuo" and should read as --*in vacuo*--.

Column 59, Line 56 reads as "invitro" and should read as --*in vitro*--.

Column 62, Line 16 reads as "wit h" and should read as --with--.

Column 62, Line 26 reads as "(lmci)" and should read as --(lmCi)--.

Column 62, Line 28 reads as "(lmci)" and should read as --(lmCi)--.

Column 63, Line 31 reads as "-amyloid-" and should read as --β-amyloid- --.

Column 71, Line 36 reads as "demnentia" and should read as --dementia--.

Signed and Sealed this

Tenth Day of April, 2001

Attest:

NICHOLAS P. GODICI

Attesting Officer

Acting Director of the United States Patent and Trademark Office